(12) United States Patent
Abou-Khalil et al.

(10) Patent No.: US 9,487,474 B2
(45) Date of Patent: Nov. 8, 2016

(54) IMINO COMPOUNDS AS PROTECTING AGENTS AGAINST ULTRAVIOLET RADIATIONS

(71) Applicant: Elkimia, Inc., Rosemere (CA)

(72) Inventors: Elie Abou-Khalil, Rosemere (CA); Stephane Raeppel, Saint-Lazare (CA); Franck Raeppel, Montreal (CA)

(73) Assignee: Elkimia, Inc., Rosemere, Quebec (CA)

( * ) Notice: Subject to any disclaimer, the term of this patent is extended or adjusted under 35 U.S.C. 154(b) by 0 days.

(21) Appl. No.: 14/405,757

(22) PCT Filed: May 31, 2013

(86) PCT No.: PCT/CA2013/000536
§ 371 (c)(1),
(2) Date: Dec. 4, 2014

(87) PCT Pub. No.: WO2013/181741
PCT Pub. Date: Dec. 12, 2013

(65) Prior Publication Data
US 2015/0152046 A1  Jun. 4, 2015

Related U.S. Application Data

(60) Provisional application No. 61/655,115, filed on Jun. 4, 2012.

(51) Int. Cl.

| | |
|---|---|
| C07D 279/16 | (2006.01) |
| C07D 241/38 | (2006.01) |
| C07C 251/20 | (2006.01) |
| A61K 8/44 | (2006.01) |
| A61K 8/49 | (2006.01) |
| A61Q 17/04 | (2006.01) |
| C07D 309/32 | (2006.01) |
| C07D 241/44 | (2006.01) |
| C07D 471/04 | (2006.01) |
| C07D 491/052 | (2006.01) |
| C07D 265/36 | (2006.01) |
| C07D 498/04 | (2006.01) |
| C07D 513/04 | (2006.01) |
| C07D 211/84 | (2006.01) |
| A61K 8/69 | (2006.01) |
| C08K 3/22 | (2006.01) |
| C08K 3/34 | (2006.01) |
| C08K 5/01 | (2006.01) |
| C08K 5/06 | (2006.01) |
| C08K 5/17 | (2006.01) |
| C08K 5/3432 | (2006.01) |
| C08K 5/5419 | (2006.01) |
| C09D 101/00 | (2006.01) |
| C09D 103/00 | (2006.01) |
| C09D 105/00 | (2006.01) |
| C09D 177/00 | (2006.01) |

(Continued)

(52) U.S. Cl.
CPC .............. *C07C 251/20* (2013.01); *A61K 8/44* (2013.01); *A61K 8/49* (2013.01); *A61K 8/494* (2013.01); *A61K 8/69* (2013.01); *A61Q 17/04* (2013.01); *C07D 211/84* (2013.01); *C07D 241/38* (2013.01); *C07D 241/44* (2013.01); *C07D 265/36* (2013.01); *C07D 279/16* (2013.01); *C07D 309/32* (2013.01); *C07D 471/04* (2013.01); *C07D 491/052* (2013.01); *C07D 498/04* (2013.01); *C07D 513/04* (2013.01); *C08K 3/22* (2013.01); *C08K 3/34* (2013.01); *C08K 3/346* (2013.01); *C08K 5/01* (2013.01); *C08K 5/06* (2013.01); *C08K 5/175* (2013.01); *C08K 5/3432* (2013.01); *C08K 5/5419* (2013.01); *C09D 101/00* (2013.01); *C09D 103/00* (2013.01); *C09D 105/00* (2013.01); *C09D 177/00* (2013.01); *C09D 191/06* (2013.01); *C09J 101/00* (2013.01); *C09J 103/00* (2013.01); *C09J 105/00* (2013.01); *C09J 177/00* (2013.01); *C09J 191/06* (2013.01); *C07C 2101/14* (2013.01); *C07C 2101/16* (2013.01); *C08K 2003/2296* (2013.01)

(58) Field of Classification Search
CPC .......................... C07D 279/16; C07D 241/38
USPC .............................................. 544/49
See application file for complete search history.

(56) References Cited

FOREIGN PATENT DOCUMENTS

AU        B-15291/88        11/1988

OTHER PUBLICATIONS

International Search Report dated Sep. 13, 2013 in related Application No. PCT/CA/2013/000536 filed May 31, 2013 (5 pages).
Kim et al., Facile Synthesis of Cyclic Vinamidinium p-Toluenesulfonates, Bulletin of the Korean Chemical Society, Feb. 20, 2004, vol. 25, No. 2 (2 pages).
Moskowitz et al., Chimie Organique Strucutre et Reactivite, C.R. Acad. Sc. Paris, Dec. 15, 1980 (4 pages).
Ostercamp et al., Rigid Core Vinamidinium Salts and Their N,N'-Rotamers, J. Org., Oct. 15, 2002, Chem, vol. 68, pp. 3099-3105.
CAS Registry No. 19164-90-0, 1984.
CAS Registry No. 19164-91-1, 1984.
CAS Registry No. 19424-76-1, 1984.
CAS Registry No. 5320-85-4, 1984.
CAS Registry No. 5320-86-5, 1984.

(Continued)

*Primary Examiner* — Kahsay Habte
(74) *Attorney, Agent, or Firm* — Dentons US LLP

(57) ABSTRACT

The present invention relates to compounds having the general Formula I: which absorb UV radiations and protect biological materials as well as non-biological materials from damaging exposure to UV radiations. The present invention also relates to formulations and compositions comprising such compounds for use in absorbing UV radiations and in protecting biological materials as well as non-biological materials against UV radiations.

Formula I

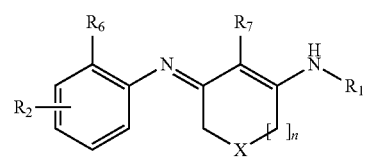

17 Claims, 17 Drawing Sheets

(51) Int. Cl.
*C09D 191/06* (2006.01)
*C09J 101/00* (2006.01)
*C09J 103/00* (2006.01)
*C09J 105/00* (2006.01)
*C09J 177/00* (2006.01)
*C09J 191/06* (2006.01)

(56) References Cited

OTHER PUBLICATIONS

CAS Registry No. 65695-59-2, 1984.
CAS Registry No. 65695-61-6, 1984.
China Office Action dated Aug. 31, 2015 in related Application No. 2013800294263 filed May 31, 2013 in English (7 pages).
China Office Action dated Aug. 31, 2015 in related Application No. 2013800294263 filed May 31, 2013 in Chinese (7 pages).
Europe Office Action dated Sep. 29, 2015 in related Application No. 13801156.4 filed May 31, 2013 (9 pages).
Granik et al., Acetals of Lactams and Acid Amides, Chemistry of Heterocyclic Compounds, Oct. 1, 1977, pp. 1083-1084, Xp055214513, Retrieved From the Internet on Sep. 18, 2015: URL: http://download.springer.com/static/pdf/859/art%3A10.1007%2FBF00480142.pdf?originUrl=http://link.springer.com/article/10.1007/BF00480142&token2=exp=1442579697 acl=/static/pdf/859/art%253A10.1007%252FBF00480142.pdf?originUrl=http%3A%2F%2Fiink.springer.com%2Farticle%2F10.1007%2FBF00480142* hmac=35e436.
Ostercamp et al., Rigid Core Vinamidinium Salts and Their N,N'-Rotamers, The Journal of Organic Chemistry, vol. 68, No. 8, Apr. 1, 2003, pp. 3099-3105, Abstract only (1 page).
Simon et al., Uber Die Umsetzung Von Bromdiacetyl Sowie Alicyclischen 1-Chlor-Dionen-(2.3) Mit Primaren Und Sekundaren Aminen Zu Reduktonen Und Einige Eigenschaften Der Produkte, Chemische Berichte, vol. 98, No. 11, Nov. 1, 1965, pp. 3692-3702, XP055214487.

| FIG. 2 | FIG. 2A |
|---|---|
| | FIG. 2B |
| | FIG. 2C |

UV-TRANSMITTANCE AT EACH WAVELENGTH (nm) FOR COMPOUND IF$_1$

| WL (nm) | Scan 1 | Scan 2 | Scan 3 | Scan 4 | Scan 5 | Scan 6 | Blank |
|---|---|---|---|---|---|---|---|
| 290 | 2.084 | 2.209 | 2.084 | 2.209 | 2.084 | 2.209 | 0.332 |
| 291 | 2.081 | 2.178 | 2.081 | 2.178 | 2.081 | 2.178 | 0.328 |
| 292 | 2.025 | 2.123 | 2.025 | 2.123 | 2.025 | 2.123 | 0.317 |
| 293 | 1.997 | 2.103 | 1.997 | 2.103 | 1.997 | 2.103 | 0.312 |
| 294 | 1.972 | 2.064 | 1.972 | 2.064 | 1.972 | 2.064 | 0.305 |
| 295 | 1.963 | 2.058 | 1.963 | 2.058 | 1.963 | 2.058 | 0.303 |
| 296 | 1.943 | 2.055 | 1.943 | 2.055 | 1.943 | 2.055 | 0.301 |
| 297 | 1.933 | 2.046 | 1.933 | 2.046 | 1.933 | 2.046 | 0.299 |
| 298 | 1.917 | 2.035 | 1.917 | 2.035 | 1.917 | 2.035 | 0.296 |
| 299 | 1.898 | 2.016 | 1.898 | 2.016 | 1.898 | 2.016 | 0.291 |
| 300 | 1.903 | 2.016 | 1.903 | 2.016 | 1.903 | 2.016 | 0.292 |
| 301 | 1.921 | 2.023 | 1.921 | 2.023 | 1.921 | 2.023 | 0.295 |
| 302 | 1.921 | 2.020 | 1.921 | 2.020 | 1.921 | 2.020 | 0.294 |
| 303 | 1.914 | 2.018 | 1.914 | 2.018 | 1.914 | 2.018 | 0.293 |
| 304 | 1.915 | 1.995 | 1.915 | 1.995 | 1.915 | 1.995 | 0.291 |
| 305 | 1.917 | 2.000 | 1.917 | 2.000 | 1.917 | 2.000 | 0.292 |
| 306 | 1.907 | 2.029 | 1.907 | 2.029 | 1.907 | 2.029 | 0.294 |
| 307 | 1.913 | 2.036 | 1.913 | 2.036 | 1.913 | 2.036 | 0.295 |
| 308 | 1.923 | 2.038 | 1.923 | 2.038 | 1.923 | 2.038 | 0.297 |
| 309 | 1.951 | 2.064 | 1.951 | 2.064 | 1.951 | 2.064 | 0.303 |
| 310 | 1.965 | 2.081 | 1.965 | 2.081 | 1.965 | 2.081 | 0.306 |
| 311 | 1.960 | 2.082 | 1.960 | 2.082 | 1.960 | 2.082 | 0.305 |
| 312 | 1.969 | 2.099 | 1.969 | 2.099 | 1.969 | 2.099 | 0.308 |
| 313 | 1.996 | 2.120 | 1.996 | 2.120 | 1.996 | 2.120 | 0.313 |
| 314 | 2.001 | 2.103 | 2.001 | 2.103 | 2.001 | 2.103 | 0.312 |
| 315 | 1.994 | 2.135 | 1.994 | 2.135 | 1.994 | 2.135 | 0.315 |
| 316 | 2.004 | 2.120 | 2.004 | 2.120 | 2.004 | 2.120 | 0.314 |
| 317 | 2.014 | 2.134 | 2.014 | 2.134 | 2.014 | 2.134 | 0.317 |
| 318 | 2.028 | 2.150 | 2.028 | 2.150 | 2.028 | 2.150 | 0.320 |
| 319 | 2.034 | 2.162 | 2.034 | 2.162 | 2.034 | 2.162 | 0.322 |
| 320 | 2.041 | 2.181 | 2.041 | 2.181 | 2.041 | 2.181 | 0.324 |
| 321 | 2.063 | 2.201 | 2.063 | 2.201 | 2.063 | 2.201 | 0.329 |
| 322 | 2.086 | 2.212 | 2.086 | 2.212 | 2.086 | 2.212 | 0.332 |
| 323 | 2.108 | 2.226 | 2.108 | 2.226 | 2.108 | 2.226 | 0.336 |

*FIG. 2A*

| 324 | 2.131 | 2.251 | 2.131 | 2.251 | 2.131 | 2.251 | 0.340 |
|---|---|---|---|---|---|---|---|
| 325 | 2.175 | 2.292 | 2.175 | 2.292 | 2.175 | 2.292 | 0.349 |
| 326 | 2.207 | 2.324 | 2.207 | 2.324 | 2.207 | 2.324 | 0.355 |
| 327 | 2.254 | 2.386 | 2.254 | 2.386 | 2.254 | 2.386 | 0.365 |
| 328 | 2.297 | 2.411 | 2.297 | 2.411 | 2.297 | 2.411 | 0.372 |
| 329 | 2.361 | 2.458 | 2.361 | 2.458 | 2.361 | 2.458 | 0.382 |
| 330 | 2.386 | 2.517 | 2.386 | 2.517 | 2.386 | 2.517 | 0.389 |
| 331 | 2.456 | 2.599 | 2.456 | 2.599 | 2.456 | 2.599 | 0.403 |
| 332 | 2.548 | 2.641 | 2.548 | 2.641 | 2.548 | 2.641 | 0.414 |
| 333 | 2.602 | 2.731 | 2.602 | 2.731 | 2.602 | 2.731 | 0.426 |
| 334 | 2.681 | 2.819 | 2.681 | 2.819 | 2.681 | 2.819 | 0.439 |
| 335 | 2.755 | 2.907 | 2.755 | 2.907 | 2.755 | 2.907 | 0.452 |
| 336 | 2.794 | 2.965 | 2.794 | 2.965 | 2.794 | 2.965 | 0.459 |
| 337 | 2.888 | 3.057 | 2.888 | 3.057 | 2.888 | 3.057 | 0.473 |
| 338 | 2.996 | 3.163 | 2.996 | 3.163 | 2.996 | 3.163 | 0.488 |
| 339 | 3.085 | 3.266 | 3.085 | 3.266 | 3.085 | 3.266 | 0.502 |
| 340 | 3.258 | 3.465 | 3.258 | 3.465 | 3.258 | 3.465 | 0.526 |
| 341 | 3.299 | 3.508 | 3.299 | 3.508 | 3.299 | 3.508 | 0.532 |
| 342 | 3.415 | 3.639 | 3.415 | 3.639 | 3.415 | 3.639 | 0.547 |
| 343 | 3.565 | 3.788 | 3.565 | 3.788 | 3.565 | 3.788 | 0.565 |
| 344 | 3.668 | 3.916 | 3.668 | 3.916 | 3.668 | 3.916 | 0.579 |
| 345 | 3.784 | 4.067 | 3.784 | 4.067 | 3.784 | 4.067 | 0.594 |
| 346 | 3.916 | 4.209 | 3.916 | 4.209 | 3.916 | 4.209 | 0.609 |
| 347 | 4.035 | 4.335 | 4.035 | 4.335 | 4.035 | 4.335 | 0.621 |
| 348 | 4.187 | 4.474 | 4.187 | 4.474 | 4.187 | 4.474 | 0.636 |
| 349 | 4.296 | 4.614 | 4.296 | 4.614 | 4.296 | 4.614 | 0.649 |
| 350 | 4.398 | 4.720 | 4.398 | 4.720 | 4.398 | 4.720 | 0.659 |
| 351 | 4.535 | 4.873 | 4.535 | 4.873 | 4.535 | 4.873 | 0.672 |
| 352 | 4.627 | 4.994 | 4.627 | 4.994 | 4.627 | 4.994 | 0.682 |
| 353 | 4.748 | 5.119 | 4.748 | 5.119 | 4.748 | 5.119 | 0.693 |
| 354 | 4.882 | 5.241 | 4.882 | 5.241 | 4.882 | 5.241 | 0.704 |
| 355 | 4.964 | 5.335 | 4.964 | 5.335 | 4.964 | 5.335 | 0.711 |
| 356 | 5.027 | 5.447 | 5.027 | 5.447 | 5.027 | 5.447 | 0.719 |
| 357 | 5.133 | 5.510 | 5.133 | 5.510 | 5.133 | 5.510 | 0.726 |
| 358 | 5.197 | 5.621 | 5.197 | 5.621 | 5.197 | 5.621 | 0.733 |
| 359 | 5.328 | 5.742 | 5.328 | 5.742 | 5.328 | 5.742 | 0.743 |
| 360 | 5.365 | 5.782 | 5.365 | 5.782 | 5.365 | 5.782 | 0.746 |
| 361 | 5.422 | 5.853 | 5.422 | 5.853 | 5.422 | 5.853 | 0.751 |
| 362 | 5.501 | 5.959 | 5.501 | 5.959 | 5.501 | 5.959 | 0.758 |
| 363 | 5.582 | 5.990 | 5.582 | 5.990 | 5.582 | 5.990 | 0.762 |
| 364 | 5.628 | 6.056 | 5.628 | 6.056 | 5.628 | 6.056 | 0.766 |
| 365 | 5.654 | 6.097 | 5.654 | 6.097 | 5.654 | 6.097 | 0.769 |
| 366 | 5.681 | 6.148 | 5.681 | 6.148 | 5.681 | 6.148 | 0.772 |

*FIG. 2B*

| | | | | | | | |
|---|---|---|---|---|---|---|---|
| 367 | 5.694 | 6.163 | 5.694 | 6.163 | 5.694 | 6.163 | 0.773 |
| 368 | 5.726 | 6.144 | 5.726 | 6.144 | 5.726 | 6.144 | 0.773 |
| 369 | 5.732 | 6.180 | 5.732 | 6.180 | 5.732 | 6.180 | 0.775 |
| 370 | 5.722 | 6.192 | 5.722 | 6.192 | 5.722 | 6.192 | 0.775 |
| 371 | 5.736 | 6.134 | 5.736 | 6.134 | 5.736 | 6.134 | 0.773 |
| 372 | 5.674 | 6.141 | 5.674 | 6.141 | 5.674 | 6.141 | 0.771 |
| 373 | 5.659 | 6.110 | 5.659 | 6.110 | 5.659 | 6.110 | 0.769 |
| 374 | 5.621 | 6.063 | 5.621 | 6.063 | 5.621 | 6.063 | 0.766 |
| 375 | 5.615 | 6.011 | 5.615 | 6.011 | 5.615 | 6.011 | 0.764 |
| 376 | 5.553 | 6.003 | 5.553 | 6.003 | 5.553 | 6.003 | 0.761 |
| 377 | 5.508 | 5.965 | 5.508 | 5.965 | 5.508 | 5.965 | 0.758 |
| 378 | 5.447 | 5.880 | 5.447 | 5.880 | 5.447 | 5.880 | 0.753 |
| 379 | 5.421 | 5.838 | 5.421 | 5.838 | 5.421 | 5.838 | 0.750 |
| 380 | 5.338 | 5.760 | 5.338 | 5.760 | 5.338 | 5.760 | 0.744 |
| 381 | 5.280 | 5.713 | 5.280 | 5.713 | 5.280 | 5.713 | 0.740 |
| 382 | 5.195 | 5.596 | 5.195 | 5.596 | 5.195 | 5.596 | 0.732 |
| 383 | 5.096 | 5.504 | 5.096 | 5.504 | 5.096 | 5.504 | 0.724 |
| 384 | 5.008 | 5.419 | 5.008 | 5.419 | 5.008 | 5.419 | 0.717 |
| 385 | 4.922 | 5.301 | 4.922 | 5.301 | 4.922 | 5.301 | 0.708 |
| 386 | 4.810 | 5.177 | 4.810 | 5.177 | 4.810 | 5.177 | 0.698 |
| 387 | 4.720 | 5.052 | 4.720 | 5.052 | 4.720 | 5.052 | 0.689 |
| 388 | 4.605 | 4.940 | 4.605 | 4.940 | 4.605 | 4.940 | 0.678 |
| 389 | 4.504 | 4.823 | 4.504 | 4.823 | 4.504 | 4.823 | 0.668 |
| 390 | 4.387 | 4.698 | 4.387 | 4.698 | 4.387 | 4.698 | 0.657 |
| 391 | 4.295 | 4.582 | 4.295 | 4.582 | 4.295 | 4.582 | 0.647 |
| 392 | 4.191 | 4.464 | 4.191 | 4.464 | 4.191 | 4.464 | 0.636 |
| 393 | 4.092 | 4.359 | 4.092 | 4.359 | 4.092 | 4.359 | 0.626 |
| 394 | 3.985 | 4.256 | 3.985 | 4.256 | 3.985 | 4.256 | 0.615 |
| 395 | 3.892 | 4.135 | 3.892 | 4.135 | 3.892 | 4.135 | 0.603 |
| 396 | 3.793 | 4.026 | 3.793 | 4.026 | 3.793 | 4.026 | 0.592 |
| 397 | 3.685 | 3.916 | 3.685 | 3.916 | 3.685 | 3.916 | 0.580 |
| 398 | 3.577 | 3.801 | 3.577 | 3.801 | 3.577 | 3.801 | 0.567 |
| 399 | 3.481 | 3.700 | 3.481 | 3.700 | 3.481 | 3.700 | 0.555 |
| 400 | 3.349 | 3.588 | 3.349 | 3.588 | 3.349 | 3.588 | 0.540 |

*FIG. 2C*

| FIG. 3 | FIG. 3A |
| | FIG. 3B |
| | FIG. 3C |

UV-TRANSMITTANCE AT EACH WAVELENGTH (nm) FOR COMPOUND $IA_1$

| WL (nm) | Scan 1 | Scan 2 | Scan 3 | Scan 4 | Scan 5 | Scan 6 | Blank |
|---|---|---|---|---|---|---|---|
| 290 | 3.248 | 3.066 | 3.248 | 3.066 | 3.248 | 3.066 | 0.4991 |
| 291 | 3.137 | 2.967 | 3.137 | 2.967 | 3.137 | 2.967 | 0.4844 |
| 292 | 3.048 | 2.877 | 3.048 | 2.877 | 3.048 | 2.877 | 0.4715 |
| 293 | 2.966 | 2.824 | 2.966 | 2.824 | 2.966 | 2.824 | 0.4615 |
| 294 | 2.862 | 2.745 | 2.862 | 2.745 | 2.862 | 2.745 | 0.4476 |
| 295 | 2.836 | 2.655 | 2.836 | 2.655 | 2.836 | 2.655 | 0.4383 |
| 296 | 2.753 | 2.636 | 2.753 | 2.636 | 2.753 | 2.636 | 0.4304 |
| 297 | 2.708 | 2.550 | 2.708 | 2.550 | 2.708 | 2.550 | 0.4196 |
| 298 | 2.612 | 2.512 | 2.612 | 2.512 | 2.612 | 2.512 | 0.4085 |
| 299 | 2.533 | 2.478 | 2.533 | 2.478 | 2.533 | 2.478 | 0.3989 |
| 300 | 2.530 | 2.406 | 2.530 | 2.406 | 2.530 | 2.406 | 0.3922 |
| 301 | 2.456 | 2.390 | 2.456 | 2.390 | 2.456 | 2.390 | 0.3843 |
| 302 | 2.404 | 2.350 | 2.404 | 2.350 | 2.404 | 2.350 | 0.3760 |
| 303 | 2.374 | 2.301 | 2.374 | 2.301 | 2.374 | 2.301 | 0.3687 |
| 304 | 2.331 | 2.213 | 2.331 | 2.213 | 2.331 | 2.213 | 0.3563 |
| 305 | 2.285 | 2.212 | 2.285 | 2.212 | 2.285 | 2.212 | 0.3519 |
| 306 | 2.279 | 2.196 | 2.279 | 2.196 | 2.279 | 2.196 | 0.3497 |
| 307 | 2.257 | 2.171 | 2.257 | 2.171 | 2.257 | 2.171 | 0.3451 |
| 308 | 2.236 | 2.153 | 2.236 | 2.153 | 2.236 | 2.153 | 0.3412 |
| 309 | 2.235 | 2.140 | 2.235 | 2.140 | 2.235 | 2.140 | 0.3399 |
| 310 | 2.239 | 2.146 | 2.239 | 2.146 | 2.239 | 2.146 | 0.3408 |
| 311 | 2.241 | 2.123 | 2.241 | 2.123 | 2.241 | 2.123 | 0.3387 |
| 312 | 2.237 | 2.159 | 2.237 | 2.159 | 2.237 | 2.159 | 0.3419 |
| 313 | 2.258 | 2.179 | 2.258 | 2.179 | 2.258 | 2.179 | 0.3460 |
| 314 | 2.273 | 2.191 | 2.273 | 2.191 | 2.273 | 2.191 | 0.3487 |
| 315 | 2.313 | 2.229 | 2.313 | 2.229 | 2.313 | 2.229 | 0.3561 |
| 316 | 2.335 | 2.231 | 2.335 | 2.231 | 2.335 | 2.231 | 0.3584 |
| 317 | 2.370 | 2.279 | 2.370 | 2.279 | 2.370 | 2.279 | 0.3662 |
| 318 | 2.412 | 2.309 | 2.412 | 2.309 | 2.412 | 2.309 | 0.3729 |
| 319 | 2.471 | 2.373 | 2.471 | 2.373 | 2.471 | 2.373 | 0.3841 |
| 320 | 2.515 | 2.428 | 2.515 | 2.428 | 2.515 | 2.428 | 0.3929 |
| 321 | 2.598 | 2.497 | 2.598 | 2.497 | 2.598 | 2.497 | 0.4061 |
| 322 | 2.678 | 2.562 | 2.678 | 2.562 | 2.678 | 2.562 | 0.4182 |
| 323 | 2.768 | 2.654 | 2.768 | 2.654 | 2.768 | 2.654 | 0.4330 |

*FIG. 3A*

| | | | | | | | |
|---|---|---|---|---|---|---|---|
| 324 | 2.850 | 2.742 | 2.850 | 2.742 | 2.850 | 2.742 | 0.4464 |
| 325 | 3.004 | 2.858 | 3.004 | 2.858 | 3.004 | 2.858 | 0.4669 |
| 326 | 3.098 | 2.955 | 3.098 | 2.955 | 3.098 | 2.955 | 0.4808 |
| 327 | 3.216 | 3.091 | 3.216 | 3.091 | 3.216 | 3.091 | 0.4987 |
| 328 | 3.376 | 3.202 | 3.376 | 3.202 | 3.376 | 3.202 | 0.5170 |
| 329 | 3.518 | 3.373 | 3.518 | 3.373 | 3.518 | 3.373 | 0.5371 |
| 330 | 3.645 | 3.453 | 3.645 | 3.453 | 3.645 | 3.453 | 0.5500 |
| 331 | 3.847 | 3.657 | 3.847 | 3.657 | 3.847 | 3.657 | 0.5741 |
| 332 | 4.046 | 3.791 | 4.046 | 3.791 | 4.046 | 3.791 | 0.5929 |
| 333 | 4.170 | 3.939 | 4.170 | 3.939 | 4.170 | 3.939 | 0.6078 |
| 334 | 4.391 | 4.110 | 4.391 | 4.110 | 4.391 | 4.110 | 0.6282 |
| 335 | 4.617 | 4.284 | 4.617 | 4.284 | 4.617 | 4.284 | 0.6481 |
| 336 | 4.761 | 4.434 | 4.761 | 4.434 | 4.761 | 4.434 | 0.6622 |
| 337 | 4.975 | 4.594 | 4.975 | 4.594 | 4.975 | 4.594 | 0.6795 |
| 338 | 5.224 | 4.819 | 5.224 | 4.819 | 5.224 | 4.819 | 0.7005 |
| 339 | 5.459 | 5.049 | 5.459 | 5.049 | 5.459 | 5.049 | 0.7201 |
| 340 | 5.795 | 5.337 | 5.795 | 5.337 | 5.795 | 5.337 | 0.7452 |
| 341 | 5.874 | 5.422 | 5.874 | 5.422 | 5.874 | 5.422 | 0.7515 |
| 342 | 6.189 | 5.728 | 6.189 | 5.728 | 6.189 | 5.728 | 0.7748 |
| 343 | 6.521 | 6.001 | 6.521 | 6.001 | 6.521 | 6.001 | 0.7963 |
| 344 | 6.774 | 6.262 | 6.774 | 6.262 | 6.774 | 6.262 | 0.8138 |
| 345 | 7.056 | 6.504 | 7.056 | 6.504 | 7.056 | 6.504 | 0.8309 |
| 346 | 7.439 | 6.743 | 7.439 | 6.743 | 7.439 | 6.743 | 0.8502 |
| 347 | 7.673 | 7.021 | 7.673 | 7.021 | 7.673 | 7.021 | 0.8657 |
| 348 | 7.973 | 7.287 | 7.973 | 7.287 | 7.973 | 7.287 | 0.8821 |
| 349 | 8.344 | 7.558 | 8.344 | 7.558 | 8.344 | 7.558 | 0.8999 |
| 350 | 8.620 | 7.775 | 8.620 | 7.775 | 8.620 | 7.775 | 0.9131 |
| 351 | 8.969 | 8.108 | 8.969 | 8.108 | 8.969 | 8.108 | 0.9308 |
| 352 | 9.258 | 8.317 | 9.258 | 8.317 | 9.258 | 8.317 | 0.9432 |
| 353 | 9.498 | 8.636 | 9.498 | 8.636 | 9.498 | 8.636 | 0.9570 |
| 354 | 9.727 | 8.855 | 9.727 | 8.855 | 9.727 | 8.855 | 0.9676 |
| 355 | 9.992 | 9.047 | 9.992 | 9.047 | 9.992 | 9.047 | 0.9781 |
| 356 | 10.202 | 9.240 | 10.202 | 9.240 | 10.202 | 9.240 | 0.9872 |
| 357 | 10.468 | 9.460 | 10.468 | 9.460 | 10.468 | 9.460 | 0.9979 |
| 358 | 10.655 | 9.681 | 10.655 | 9.681 | 10.655 | 9.681 | 1.0067 |
| 359 | 10.859 | 9.880 | 10.859 | 9.880 | 10.859 | 9.880 | 1.0153 |
| 360 | 11.068 | 10.036 | 11.068 | 10.036 | 11.068 | 10.036 | 1.0228 |
| 361 | 11.255 | 10.193 | 11.255 | 10.193 | 11.255 | 10.193 | 1.0298 |
| 362 | 11.490 | 10.314 | 11.490 | 10.314 | 11.490 | 10.314 | 1.0369 |
| 363 | 11.735 | 10.532 | 11.735 | 10.532 | 11.735 | 10.532 | 1.0460 |
| 364 | 11.775 | 10.728 | 11.775 | 10.728 | 11.775 | 10.728 | 1.0507 |
| 365 | 12.033 | 10.834 | 12.033 | 10.834 | 12.033 | 10.834 | 1.0576 |
| 366 | 12.177 | 10.938 | 12.177 | 10.938 | 12.177 | 10.938 | 1.0622 |

*FIG. 3B*

| | | | | | | | |
|---|---|---|---|---|---|---|---|
| 367 | 12.192 | 10.880 | 12.192 | 10.880 | 12.192 | 10.880 | 1.0614 |
| 368 | 12.225 | 11.005 | 12.225 | 11.005 | 12.225 | 11.005 | 1.0644 |
| 369 | 12.431 | 11.124 | 12.431 | 11.124 | 12.431 | 11.124 | 1.0704 |
| 370 | 12.416 | 11.171 | 12.416 | 11.171 | 12.416 | 11.171 | 1.0710 |
| 371 | 12.354 | 10.997 | 12.354 | 10.997 | 12.354 | 10.997 | 1.0665 |
| 372 | 12.274 | 11.019 | 12.274 | 11.019 | 12.274 | 11.019 | 1.0655 |
| 373 | 12.220 | 10.994 | 12.220 | 10.994 | 12.220 | 10.994 | 1.0641 |
| 374 | 12.165 | 10.950 | 12.165 | 10.950 | 12.165 | 10.950 | 1.0623 |
| 375 | 12.128 | 10.855 | 12.128 | 10.855 | 12.128 | 10.855 | 1.0597 |
| 376 | 12.024 | 10.848 | 12.024 | 10.848 | 12.024 | 10.848 | 1.0577 |
| 377 | 11.872 | 10.722 | 11.872 | 10.722 | 11.872 | 10.722 | 1.0524 |
| 378 | 11.753 | 10.668 | 11.753 | 10.668 | 11.753 | 10.668 | 1.0491 |
| 379 | 11.613 | 10.548 | 11.613 | 10.548 | 11.613 | 10.548 | 1.0441 |
| 380 | 11.504 | 10.403 | 11.504 | 10.403 | 11.504 | 10.403 | 1.0390 |
| 381 | 11.366 | 10.282 | 11.366 | 10.282 | 11.366 | 10.282 | 1.0339 |
| 382 | 11.142 | 10.105 | 11.142 | 10.105 | 11.142 | 10.105 | 1.0257 |
| 383 | 10.932 | 9.893 | 10.932 | 9.893 | 10.932 | 9.893 | 1.0170 |
| 384 | 10.714 | 9.690 | 10.714 | 9.690 | 10.714 | 9.690 | 1.0081 |
| 385 | 10.544 | 9.526 | 10.544 | 9.526 | 10.544 | 9.526 | 1.0010 |
| 386 | 10.285 | 9.339 | 10.285 | 9.339 | 10.285 | 9.339 | 0.9913 |
| 387 | 10.035 | 9.096 | 10.035 | 9.096 | 10.035 | 9.096 | 0.9802 |
| 388 | 9.821 | 8.882 | 9.821 | 8.882 | 9.821 | 8.882 | 0.9703 |
| 389 | 9.518 | 8.653 | 9.518 | 8.653 | 9.518 | 8.653 | 0.9578 |
| 390 | 9.270 | 8.436 | 9.270 | 8.436 | 9.270 | 8.436 | 0.9466 |
| 391 | 9.026 | 8.207 | 9.026 | 8.207 | 9.026 | 8.207 | 0.9348 |
| 392 | 8.761 | 7.957 | 8.761 | 7.957 | 8.761 | 7.957 | 0.9217 |
| 393 | 8.520 | 7.788 | 8.520 | 7.788 | 8.520 | 7.788 | 0.9109 |
| 394 | 8.259 | 7.584 | 8.259 | 7.584 | 8.259 | 7.584 | 0.8984 |
| 395 | 8.021 | 7.356 | 8.021 | 7.356 | 8.021 | 7.356 | 0.8854 |
| 396 | 7.786 | 7.102 | 7.786 | 7.102 | 7.786 | 7.102 | 0.8713 |
| 397 | 7.506 | 6.900 | 7.506 | 6.900 | 7.506 | 6.900 | 0.8571 |
| 398 | 7.251 | 6.687 | 7.251 | 6.687 | 7.251 | 6.687 | 0.8428 |
| 399 | 7.007 | 6.462 | 7.007 | 6.462 | 7.007 | 6.462 | 0.8279 |
| 400 | 6.768 | 6.223 | 6.768 | 6.223 | 6.768 | 6.223 | 0.8122 |

*FIG. 3C*

| | FIG. 4A |
|---|---|
| FIG. 4 | FIG. 4B |
| | FIG. 4C |

UV-TRANSMITTANCE AT EACH WAVELENGTH (nm) FOR COMPOUND IA$_2$

| WL (nm) | Scan 1 | Scan 2 | Scan 3 | Scan 4 | Scan 5 | Scan 6 | Blank |
|---|---|---|---|---|---|---|---|
| 290 | 5.814 | 5.694 | 5.814 | 5.694 | 5.814 | 5.694 | 0.7599 |
| 291 | 5.671 | 5.563 | 5.671 | 5.563 | 5.671 | 5.563 | 0.7495 |
| 292 | 5.750 | 5.653 | 5.750 | 5.653 | 5.750 | 5.653 | 0.7560 |
| 293 | 5.699 | 5.640 | 5.699 | 5.640 | 5.699 | 5.640 | 0.7535 |
| 294 | 5.607 | 5.574 | 5.607 | 5.574 | 5.607 | 5.574 | 0.7474 |
| 295 | 5.561 | 5.451 | 5.561 | 5.451 | 5.561 | 5.451 | 0.7408 |
| 296 | 5.575 | 5.436 | 5.575 | 5.436 | 5.575 | 5.436 | 0.7408 |
| 297 | 5.543 | 5.579 | 5.543 | 5.579 | 5.543 | 5.579 | 0.7451 |
| 298 | 5.547 | 5.483 | 5.547 | 5.483 | 5.547 | 5.483 | 0.7415 |
| 299 | 5.442 | 5.484 | 5.442 | 5.484 | 5.442 | 5.484 | 0.7374 |
| 300 | 5.406 | 5.307 | 5.406 | 5.307 | 5.406 | 5.307 | 0.7289 |
| 301 | 5.376 | 5.339 | 5.376 | 5.339 | 5.376 | 5.339 | 0.7290 |
| 302 | 5.315 | 5.251 | 5.315 | 5.251 | 5.315 | 5.251 | 0.7229 |
| 303 | 5.344 | 5.286 | 5.344 | 5.286 | 5.344 | 5.286 | 0.7255 |
| 304 | 5.309 | 5.232 | 5.309 | 5.232 | 5.309 | 5.232 | 0.7218 |
| 305 | 5.163 | 5.147 | 5.163 | 5.147 | 5.163 | 5.147 | 0.7122 |
| 306 | 5.209 | 5.229 | 5.209 | 5.229 | 5.209 | 5.229 | 0.7176 |
| 307 | 5.129 | 5.131 | 5.129 | 5.131 | 5.129 | 5.131 | 0.7101 |
| 308 | 5.116 | 5.063 | 5.116 | 5.063 | 5.116 | 5.063 | 0.7067 |
| 309 | 5.095 | 5.006 | 5.095 | 5.006 | 5.095 | 5.006 | 0.7033 |
| 310 | 5.004 | 4.891 | 5.004 | 4.891 | 5.004 | 4.891 | 0.6944 |
| 311 | 4.990 | 4.923 | 4.990 | 4.923 | 4.990 | 4.923 | 0.6951 |
| 312 | 4.886 | 4.809 | 4.886 | 4.809 | 4.886 | 4.809 | 0.6855 |
| 313 | 4.861 | 4.811 | 4.861 | 4.811 | 4.861 | 4.811 | 0.6845 |
| 314 | 4.851 | 4.802 | 4.851 | 4.802 | 4.851 | 4.802 | 0.6836 |
| 315 | 4.781 | 4.744 | 4.781 | 4.744 | 4.781 | 4.744 | 0.6778 |
| 316 | 4.701 | 4.631 | 4.701 | 4.631 | 4.701 | 4.631 | 0.6690 |
| 317 | 4.648 | 4.604 | 4.648 | 4.604 | 4.648 | 4.604 | 0.6652 |
| 318 | 4.542 | 4.554 | 4.542 | 4.554 | 4.542 | 4.554 | 0.6578 |
| 319 | 4.471 | 4.413 | 4.471 | 4.413 | 4.471 | 4.413 | 0.6476 |
| 320 | 4.437 | 4.401 | 4.437 | 4.401 | 4.437 | 4.401 | 0.6453 |
| 321 | 4.317 | 4.344 | 4.317 | 4.344 | 4.317 | 4.344 | 0.6365 |
| 322 | 4.354 | 4.321 | 4.354 | 4.321 | 4.354 | 4.321 | 0.6373 |
| 323 | 4.261 | 4.184 | 4.261 | 4.184 | 4.261 | 4.184 | 0.6255 |

*FIG. 4A*

| | | | | | | | |
|---|---|---|---|---|---|---|---|
| 324 | 4.152 | 4.167 | 4.152 | 4.167 | 4.152 | 4.167 | 0.6190 |
| 325 | 4.161 | 4.046 | 4.161 | 4.046 | 4.161 | 4.046 | 0.6131 |
| 326 | 4.120 | 4.054 | 4.120 | 4.054 | 4.120 | 4.054 | 0.6114 |
| 327 | 4.058 | 3.996 | 4.058 | 3.996 | 4.058 | 3.996 | 0.6049 |
| 328 | 4.065 | 4.025 | 4.065 | 4.025 | 4.065 | 4.025 | 0.6069 |
| 329 | 4.049 | 4.016 | 4.049 | 4.016 | 4.049 | 4.016 | 0.6056 |
| 330 | 3.992 | 3.970 | 3.992 | 3.970 | 3.992 | 3.970 | 0.6000 |
| 331 | 3.972 | 3.909 | 3.972 | 3.909 | 3.972 | 3.909 | 0.5956 |
| 332 | 4.091 | 4.005 | 4.091 | 4.005 | 4.091 | 4.005 | 0.6072 |
| 333 | 4.105 | 4.018 | 4.105 | 4.018 | 4.105 | 4.018 | 0.6087 |
| 334 | 4.112 | 4.083 | 4.112 | 4.083 | 4.112 | 4.083 | 0.6125 |
| 335 | 4.201 | 4.107 | 4.201 | 4.107 | 4.201 | 4.107 | 0.6185 |
| 336 | 4.143 | 4.155 | 4.143 | 4.155 | 4.143 | 4.155 | 0.6179 |
| 337 | 4.323 | 4.244 | 4.323 | 4.244 | 4.323 | 4.244 | 0.6318 |
| 338 | 4.414 | 4.327 | 4.414 | 4.327 | 4.414 | 4.327 | 0.6405 |
| 339 | 4.450 | 4.398 | 4.450 | 4.398 | 4.450 | 4.398 | 0.6458 |
| 340 | 4.606 | 4.577 | 4.606 | 4.577 | 4.606 | 4.577 | 0.6619 |
| 341 | 4.773 | 4.716 | 4.773 | 4.716 | 4.773 | 4.716 | 0.6762 |
| 342 | 4.956 | 4.909 | 4.956 | 4.909 | 4.956 | 4.909 | 0.6931 |
| 343 | 5.077 | 5.066 | 5.077 | 5.066 | 5.077 | 5.066 | 0.7051 |
| 344 | 5.272 | 5.235 | 5.272 | 5.235 | 5.272 | 5.235 | 0.7204 |
| 345 | 5.497 | 5.402 | 5.497 | 5.402 | 5.497 | 5.402 | 0.7363 |
| 346 | 5.724 | 5.681 | 5.724 | 5.681 | 5.724 | 5.681 | 0.7560 |
| 347 | 5.984 | 5.910 | 5.984 | 5.910 | 5.984 | 5.910 | 0.7743 |
| 348 | 6.274 | 6.192 | 6.274 | 6.192 | 6.274 | 6.192 | 0.7947 |
| 349 | 6.546 | 6.462 | 6.546 | 6.462 | 6.546 | 6.462 | 0.8132 |
| 350 | 6.871 | 6.806 | 6.871 | 6.806 | 6.871 | 6.806 | 0.8350 |
| 351 | 7.224 | 7.170 | 7.224 | 7.170 | 7.224 | 7.170 | 0.8571 |
| 352 | 7.471 | 7.451 | 7.471 | 7.451 | 7.471 | 7.451 | 0.8728 |
| 353 | 7.913 | 7.891 | 7.913 | 7.891 | 7.913 | 7.891 | 0.8977 |
| 354 | 8.281 | 8.264 | 8.281 | 8.264 | 8.281 | 8.264 | 0.9176 |
| 355 | 8.572 | 8.525 | 8.572 | 8.525 | 8.572 | 8.525 | 0.9319 |
| 356 | 8.998 | 8.953 | 8.998 | 8.953 | 8.998 | 8.953 | 0.9531 |
| 357 | 9.428 | 9.426 | 9.428 | 9.426 | 9.428 | 9.426 | 0.9744 |
| 358 | 9.856 | 9.789 | 9.856 | 9.789 | 9.856 | 9.789 | 0.9922 |
| 359 | 10.467 | 10.282 | 10.467 | 10.282 | 10.467 | 10.282 | 1.0160 |
| 360 | 10.940 | 10.687 | 10.940 | 10.687 | 10.940 | 10.687 | 1.0339 |
| 361 | 11.390 | 11.214 | 11.390 | 11.214 | 11.390 | 11.214 | 1.0531 |
| 362 | 12.043 | 11.807 | 12.043 | 11.807 | 12.043 | 11.807 | 1.0764 |
| 363 | 12.516 | 12.319 | 12.516 | 12.319 | 12.516 | 12.319 | 1.0940 |
| 364 | 13.034 | 12.953 | 13.034 | 12.953 | 13.034 | 12.953 | 1.1137 |
| 365 | 13.561 | 13.461 | 13.561 | 13.461 | 13.561 | 13.461 | 1.1307 |
| 366 | 14.274 | 14.115 | 14.274 | 14.115 | 14.274 | 14.115 | 1.1521 |

*FIG. 4B*

| | | | | | | | |
|---|---|---|---|---|---|---|---|
| 367 | 14.887 | 14.743 | 14.887 | 14.743 | 14.887 | 14.743 | 1.1707 |
| 368 | 15.406 | 15.349 | 15.406 | 15.349 | 15.406 | 15.349 | 1.1869 |
| 369 | 15.972 | 15.887 | 15.972 | 15.887 | 15.972 | 15.887 | 1.2022 |
| 370 | 16.847 | 16.846 | 16.847 | 16.846 | 16.847 | 16.846 | 1.2265 |
| 371 | 17.369 | 17.169 | 17.369 | 17.169 | 17.369 | 17.169 | 1.2373 |
| 372 | 18.092 | 17.702 | 18.092 | 17.702 | 18.092 | 17.702 | 1.2528 |
| 373 | 18.622 | 18.210 | 18.622 | 18.210 | 18.622 | 18.210 | 1.2652 |
| 374 | 19.156 | 18.967 | 19.156 | 18.967 | 19.156 | 18.967 | 1.2802 |
| 375 | 19.941 | 19.628 | 19.941 | 19.628 | 19.941 | 19.628 | 1.2963 |
| 376 | 20.389 | 20.095 | 20.389 | 20.095 | 20.389 | 20.095 | 1.3062 |
| 377 | 20.990 | 20.537 | 20.990 | 20.537 | 20.990 | 20.537 | 1.3173 |
| 378 | 21.520 | 21.030 | 21.520 | 21.030 | 21.520 | 21.030 | 1.3278 |
| 379 | 22.065 | 21.668 | 22.065 | 21.668 | 22.065 | 21.668 | 1.3398 |
| 380 | 22.619 | 22.232 | 22.619 | 22.232 | 22.619 | 22.232 | 1.3507 |
| 381 | 23.213 | 22.635 | 23.213 | 22.635 | 23.213 | 22.635 | 1.3602 |
| 382 | 23.642 | 23.034 | 23.642 | 23.034 | 23.642 | 23.034 | 1.3680 |
| 383 | 24.238 | 23.382 | 24.238 | 23.382 | 24.238 | 23.382 | 1.3767 |
| 384 | 24.649 | 23.866 | 24.649 | 23.866 | 24.649 | 23.866 | 1.3848 |
| 385 | 24.919 | 24.200 | 24.919 | 24.200 | 24.919 | 24.200 | 1.3902 |
| 386 | 25.321 | 24.608 | 25.321 | 24.608 | 25.321 | 24.608 | 1.3973 |
| 387 | 25.696 | 25.044 | 25.696 | 25.044 | 25.696 | 25.044 | 1.4043 |
| 388 | 25.997 | 25.255 | 25.997 | 25.255 | 25.997 | 25.255 | 1.4086 |
| 389 | 26.304 | 25.600 | 26.304 | 25.600 | 26.304 | 25.600 | 1.4141 |
| 390 | 26.551 | 25.995 | 26.551 | 25.995 | 26.551 | 25.995 | 1.4195 |
| 391 | 26.897 | 26.192 | 26.897 | 26.192 | 26.897 | 26.192 | 1.4239 |
| 392 | 27.153 | 26.321 | 27.153 | 26.321 | 27.153 | 26.321 | 1.4271 |
| 393 | 27.609 | 26.728 | 27.609 | 26.728 | 27.609 | 26.728 | 1.4340 |
| 394 | 27.627 | 26.834 | 27.627 | 26.834 | 27.627 | 26.834 | 1.4350 |
| 395 | 27.955 | 27.323 | 27.955 | 27.323 | 27.955 | 27.323 | 1.4415 |
| 396 | 28.158 | 27.266 | 28.158 | 27.266 | 28.158 | 27.266 | 1.4426 |
| 397 | 28.252 | 27.396 | 28.252 | 27.396 | 28.252 | 27.396 | 1.4444 |
| 398 | 28.363 | 27.484 | 28.363 | 27.484 | 28.363 | 27.484 | 1.4459 |
| 399 | 28.455 | 27.502 | 28.455 | 27.502 | 28.455 | 27.502 | 1.4468 |
| 400 | 28.481 | 27.783 | 28.481 | 27.783 | 28.481 | 27.783 | 1.4492 |

*FIG. 4C*

| | FIG. 5A |
|---|---|
| FIG. 5 | FIG. 5B |
| | FIG. 5C |

UV-TRANSMITTANCE AT EACH WAVELENGTH (nm) FOR COMPOUND IE$_4$

| WL (nm) | Scan 1 | Scan 2 | Scan 3 | Scan 4 | Scan 5 | Scan 6 | Blank |
|---|---|---|---|---|---|---|---|
| 290 | 6.334 | 6.019 | 6.334 | 6.019 | 6.334 | 6.019 | 0.7906 |
| 291 | 6.095 | 5.686 | 6.095 | 5.686 | 6.095 | 5.686 | 0.7699 |
| 292 | 5.887 | 5.588 | 5.887 | 5.588 | 5.887 | 5.588 | 0.7586 |
| 293 | 5.664 | 5.375 | 5.664 | 5.375 | 5.664 | 5.375 | 0.7418 |
| 294 | 5.401 | 5.127 | 5.401 | 5.127 | 5.401 | 5.127 | 0.7211 |
| 295 | 5.147 | 4.932 | 5.147 | 4.932 | 5.147 | 4.932 | 0.7023 |
| 296 | 5.068 | 4.789 | 5.068 | 4.789 | 5.068 | 4.789 | 0.6926 |
| 297 | 4.964 | 4.677 | 4.964 | 4.677 | 4.964 | 4.677 | 0.6829 |
| 298 | 4.887 | 4.594 | 4.887 | 4.594 | 4.887 | 4.594 | 0.6756 |
| 299 | 4.759 | 4.488 | 4.759 | 4.488 | 4.759 | 4.488 | 0.6648 |
| 300 | 4.547 | 4.265 | 4.547 | 4.265 | 4.547 | 4.265 | 0.6438 |
| 301 | 4.549 | 4.291 | 4.549 | 4.291 | 4.549 | 4.291 | 0.6452 |
| 302 | 4.403 | 4.151 | 4.403 | 4.151 | 4.403 | 4.151 | 0.6310 |
| 303 | 4.379 | 4.138 | 4.379 | 4.138 | 4.379 | 4.138 | 0.6291 |
| 304 | 4.369 | 4.069 | 4.369 | 4.069 | 4.369 | 4.069 | 0.6250 |
| 305 | 4.287 | 4.011 | 4.287 | 4.011 | 4.287 | 4.011 | 0.6177 |
| 306 | 4.340 | 4.068 | 4.340 | 4.068 | 4.340 | 4.068 | 0.6234 |
| 307 | 4.296 | 4.032 | 4.296 | 4.032 | 4.296 | 4.032 | 0.6193 |
| 308 | 4.283 | 4.036 | 4.283 | 4.036 | 4.283 | 4.036 | 0.6189 |
| 309 | 4.292 | 4.071 | 4.292 | 4.071 | 4.292 | 4.071 | 0.6212 |
| 310 | 4.287 | 4.043 | 4.287 | 4.043 | 4.287 | 4.043 | 0.6194 |
| 311 | 4.336 | 4.105 | 4.336 | 4.105 | 4.336 | 4.105 | 0.6252 |
| 312 | 4.400 | 4.101 | 4.400 | 4.101 | 4.400 | 4.101 | 0.6282 |
| 313 | 4.425 | 4.225 | 4.425 | 4.225 | 4.425 | 4.225 | 0.6359 |
| 314 | 4.530 | 4.300 | 4.530 | 4.300 | 4.530 | 4.300 | 0.6448 |
| 315 | 4.585 | 4.338 | 4.585 | 4.338 | 4.585 | 4.338 | 0.6493 |
| 316 | 4.618 | 4.388 | 4.618 | 4.388 | 4.618 | 4.388 | 0.6533 |
| 317 | 4.669 | 4.403 | 4.669 | 4.403 | 4.669 | 4.403 | 0.6565 |
| 318 | 4.756 | 4.474 | 4.756 | 4.474 | 4.756 | 4.474 | 0.6640 |
| 319 | 4.820 | 4.509 | 4.820 | 4.509 | 4.820 | 4.509 | 0.6685 |
| 320 | 4.902 | 4.620 | 4.902 | 4.620 | 4.902 | 4.620 | 0.6775 |
| 321 | 5.023 | 4.656 | 5.023 | 4.656 | 5.023 | 4.656 | 0.6845 |
| 322 | 5.089 | 4.826 | 5.089 | 4.826 | 5.089 | 4.826 | 0.6951 |
| 323 | 5.130 | 4.836 | 5.130 | 4.836 | 5.130 | 4.8366 | 0.6973 |

*FIG. 5A*

| 324 | 5.334 | 4.989 | 5.334 | 4.989 | 5.334 | 4.989 | 0.7125 |
|---|---|---|---|---|---|---|---|
| 325 | 5.380 | 5.046 | 5.380 | 5.046 | 5.380 | 5.046 | 0.7168 |
| 326 | 5.401 | 5.226 | 5.401 | 5.226 | 5.401 | 5.226 | 0.7253 |
| 327 | 5.545 | 5.321 | 5.545 | 5.321 | 5.545 | 5.321 | 0.7350 |
| 328 | 5.730 | 5.414 | 5.730 | 5.414 | 5.730 | 5.414 | 0.7458 |
| 329 | 5.897 | 5.480 | 5.897 | 5.480 | 5.897 | 5.480 | 0.7547 |
| 330 | 5.994 | 5.563 | 5.994 | 5.563 | 5.994 | 5.563 | 0.7615 |
| 331 | 5.988 | 5.519 | 5.988 | 5.519 | 5.988 | 5.519 | 0.7596 |
| 332 | 6.172 | 5.797 | 6.172 | 5.797 | 6.172 | 5.797 | 0.7768 |
| 333 | 6.257 | 5.850 | 6.257 | 5.850 | 6.257 | 5.850 | 0.7818 |
| 334 | 6.380 | 6.171 | 6.380 | 6.171 | 6.380 | 6.171 | 0.7976 |
| 335 | 6.528 | 6.175 | 6.528 | 6.175 | 6.528 | 6.175 | 0.8027 |
| 336 | 6.565 | 6.046 | 6.565 | 6.046 | 6.565 | 6.046 | 0.7993 |
| 337 | 6.705 | 6.252 | 6.705 | 6.252 | 6.705 | 6.252 | 0.8112 |
| 338 | 6.890 | 6.457 | 6.890 | 6.457 | 6.890 | 6.457 | 0.8241 |
| 339 | 6.867 | 6.476 | 6.867 | 6.476 | 6.867 | 6.476 | 0.8240 |
| 340 | 7.114 | 6.677 | 7.114 | 6.677 | 7.114 | 6.677 | 0.8383 |
| 341 | 7.338 | 6.940 | 7.338 | 6.940 | 7.338 | 6.940 | 0.8535 |
| 342 | 7.499 | 7.077 | 7.499 | 7.077 | 7.499 | 7.077 | 0.8625 |
| 343 | 7.574 | 7.181 | 7.574 | 7.181 | 7.574 | 7.181 | 0.8677 |
| 344 | 7.687 | 7.286 | 7.687 | 7.286 | 7.687 | 7.286 | 0.8741 |
| 345 | 7.900 | 7.477 | 7.900 | 7.477 | 7.900 | 7.477 | 0.8857 |
| 346 | 8.086 | 7.612 | 8.086 | 7.612 | 8.086 | 7.612 | 0.8946 |
| 347 | 8.109 | 7.669 | 8.109 | 7.669 | 8.109 | 7.669 | 0.8969 |
| 348 | 8.348 | 7.882 | 8.348 | 7.882 | 8.348 | 7.882 | 0.9091 |
| 349 | 8.501 | 7.981 | 8.501 | 7.981 | 8.501 | 7.981 | 0.9158 |
| 350 | 8.599 | 8.151 | 8.599 | 8.151 | 8.599 | 8.151 | 0.9228 |
| 351 | 8.809 | 8.288 | 8.809 | 8.288 | 8.809 | 8.288 | 0.9317 |
| 352 | 8.840 | 8.359 | 8.840 | 8.359 | 8.840 | 8.359 | 0.9343 |
| 353 | 9.023 | 8.522 | 9.023 | 8.522 | 9.023 | 8.522 | 0.9429 |
| 354 | 9.146 | 8.630 | 9.146 | 8.630 | 9.146 | 8.630 | 0.9486 |
| 355 | 9.166 | 8.676 | 9.166 | 8.676 | 9.166 | 8.676 | 0.9502 |
| 356 | 9.341 | 8.769 | 9.341 | 8.769 | 9.341 | 8.769 | 0.9567 |
| 357 | 9.541 | 8.913 | 9.541 | 8.913 | 9.541 | 8.913 | 0.9648 |
| 358 | 9.586 | 9.091 | 9.586 | 9.091 | 9.586 | 9.091 | 0.9701 |
| 359 | 9.655 | 9.159 | 9.655 | 9.159 | 9.655 | 9.159 | 0.9733 |
| 360 | 9.836 | 9.270 | 9.836 | 9.270 | 9.836 | 9.270 | 0.9799 |
| 361 | 9.872 | 9.300 | 9.872 | 9.300 | 9.872 | 9.300 | 0.9814 |
| 362 | 10.070 | 9.416 | 10.070 | 9.416 | 10.070 | 9.416 | 0.9884 |
| 363 | 10.059 | 9.519 | 10.059 | 9.519 | 10.059 | 9.519 | 0.9906 |
| 364 | 10.181 | 9.546 | 10.181 | 9.546 | 10.181 | 9.546 | 0.9938 |
| 365 | 10.262 | 9.661 | 10.262 | 9.661 | 10.262 | 9.661 | 0.9981 |
| 366 | 10.309 | 9.725 | 10.309 | 9.725 | 10.309 | 9.725 | 1.0005 |

*FIG. 5B*

| 367 | 10.316 | 9.775 | 10.316 | 9.775 | 10.316 | 9.775 | 1.0018 |
| 368 | 10.464 | 9.935 | 10.464 | 9.935 | 10.464 | 9.935 | 1.0084 |
| 369 | 10.514 | 9.898 | 10.514 | 9.898 | 10.514 | 9.898 | 1.0087 |
| 370 | 10.547 | 10.014 | 10.547 | 10.014 | 10.547 | 10.014 | 1.0119 |
| 371 | 10.610 | 9.925 | 10.610 | 9.925 | 10.610 | 9.925 | 1.0112 |
| 372 | 10.628 | 9.991 | 10.628 | 9.991 | 10.628 | 9.991 | 1.0130 |
| 373 | 10.609 | 9.975 | 10.609 | 9.975 | 10.609 | 9.975 | 1.0123 |
| 374 | 10.601 | 10.044 | 10.601 | 10.044 | 10.601 | 10.044 | 1.0136 |
| 375 | 10.654 | 10.046 | 10.654 | 10.046 | 10.654 | 10.046 | 1.0147 |
| 376 | 10.694 | 10.076 | 10.694 | 10.076 | 10.694 | 10.076 | 1.0162 |
| 377 | 10.675 | 10.035 | 10.675 | 10.035 | 10.675 | 10.035 | 1.0149 |
| 378 | 10.659 | 10.039 | 10.659 | 10.039 | 10.659 | 10.039 | 1.0147 |
| 379 | 10.690 | 9.997 | 10.690 | 9.997 | 10.690 | 9.997 | 1.0144 |
| 380 | 10.657 | 10.036 | 10.657 | 10.036 | 10.657 | 10.036 | 1.0146 |
| 381 | 10.594 | 10.021 | 10.594 | 10.021 | 10.594 | 10.021 | 1.0130 |
| 382 | 10.570 | 9.967 | 10.570 | 9.967 | 10.570 | 9.967 | 1.0113 |
| 383 | 10.527 | 9.939 | 10.527 | 9.939 | 10.527 | 9.939 | 1.0098 |
| 384 | 10.482 | 9.879 | 10.482 | 9.879 | 10.482 | 9.879 | 1.0076 |
| 385 | 10.429 | 9.830 | 10.429 | 9.830 | 10.429 | 9.830 | 1.0054 |
| 386 | 10.385 | 9.811 | 10.385 | 9.811 | 10.385 | 9.811 | 1.0041 |
| 387 | 10.326 | 9.747 | 10.326 | 9.747 | 10.326 | 9.747 | 1.0014 |
| 388 | 10.311 | 9.705 | 10.311 | 9.705 | 10.311 | 9.705 | 1.0002 |
| 389 | 10.227 | 9.650 | 10.227 | 9.650 | 10.227 | 9.650 | 0.9972 |
| 390 | 10.128 | 9.572 | 10.128 | 9.572 | 10.128 | 9.572 | 0.9932 |
| 391 | 10.050 | 9.521 | 10.050 | 9.521 | 10.050 | 9.521 | 0.9904 |
| 392 | 10.002 | 9.478 | 10.002 | 9.478 | 10.002 | 9.478 | 0.9884 |
| 393 | 9.940 | 9.407 | 9.940 | 9.407 | 9.940 | 9.407 | 0.9854 |
| 394 | 9.875 | 9.332 | 9.875 | 9.332 | 9.875 | 9.332 | 0.9822 |
| 395 | 9.822 | 9.306 | 9.822 | 9.306 | 9.822 | 9.306 | 0.9805 |
| 396 | 9.749 | 9.229 | 9.749 | 9.229 | 9.749 | 9.229 | 0.9771 |
| 397 | 9.650 | 9.144 | 9.650 | 9.144 | 9.650 | 9.144 | 0.9728 |
| 398 | 9.551 | 9.064 | 9.551 | 9.064 | 9.551 | 9.064 | 0.9687 |
| 399 | 9.478 | 8.972 | 9.478 | 8.972 | 9.478 | 8.972 | 0.9648 |
| 400 | 9.385 | 8.901 | 9.385 | 8.901 | 9.385 | 8.901 | 0.9609 |

*FIG. 5C*

| FIG. 6 | FIG. 6A |
|        | FIG. 6B |
|        | FIG. 6C |

UV-TRANSMITTANCE AT EACH WAVELENGTH (nm) FOR COMPOUND IE$_1$

| WL (nm) | Scan 1 | Scan 2 | Scan 3 | Scan 4 | Scan 5 | Scan 6 | Blank |
|---|---|---|---|---|---|---|---|
| 290 | 6.060 | 6.406 | 6.060 | 6.406 | 6.060 | 6.406 | 0.7945 |
| 291 | 5.741 | 5.984 | 5.741 | 5.984 | 5.741 | 5.984 | 0.7680 |
| 292 | 5.550 | 5.690 | 5.550 | 5.690 | 5.550 | 5.690 | 0.7497 |
| 293 | 5.232 | 5.484 | 5.232 | 5.484 | 5.232 | 5.484 | 0.7289 |
| 294 | 4.918 | 5.187 | 4.918 | 5.187 | 4.918 | 5.187 | 0.7034 |
| 295 | 4.726 | 4.874 | 4.726 | 4.874 | 4.726 | 4.874 | 0.6812 |
| 296 | 4.489 | 4.640 | 4.489 | 4.640 | 4.489 | 4.640 | 0.6593 |
| 297 | 4.375 | 4.498 | 4.375 | 4.498 | 4.375 | 4.498 | 0.6470 |
| 298 | 4.152 | 4.297 | 4.152 | 4.297 | 4.152 | 4.297 | 0.6257 |
| 299 | 3.935 | 4.094 | 3.935 | 4.094 | 3.935 | 4.094 | 0.6036 |
| 300 | 3.751 | 3.889 | 3.751 | 3.889 | 3.751 | 3.889 | 0.5820 |
| 301 | 3.656 | 3.822 | 3.656 | 3.822 | 3.656 | 3.822 | 0.5726 |
| 302 | 3.499 | 3.619 | 3.499 | 3.619 | 3.499 | 3.619 | 0.5512 |
| 303 | 3.433 | 3.558 | 3.433 | 3.558 | 3.433 | 3.558 | 0.5434 |
| 304 | 3.303 | 3.386 | 3.303 | 3.386 | 3.303 | 3.386 | 0.5243 |
| 305 | 3.160 | 3.262 | 3.160 | 3.262 | 3.160 | 3.262 | 0.5065 |
| 306 | 3.137 | 3.220 | 3.137 | 3.220 | 3.137 | 3.220 | 0.5022 |
| 307 | 3.053 | 3.153 | 3.053 | 3.153 | 3.053 | 3.153 | 0.4917 |
| 308 | 3.001 | 3.095 | 3.001 | 3.095 | 3.001 | 3.095 | 0.4840 |
| 309 | 2.966 | 3.043 | 2.966 | 3.043 | 2.966 | 3.043 | 0.4777 |
| 310 | 2.902 | 2.984 | 2.902 | 2.984 | 2.902 | 2.984 | 0.4688 |
| 311 | 2.930 | 3.012 | 2.930 | 3.012 | 2.930 | 3.012 | 0.4728 |
| 312 | 2.927 | 2.960 | 2.927 | 2.960 | 2.927 | 2.960 | 0.4688 |
| 313 | 2.872 | 2.986 | 2.872 | 2.986 | 2.872 | 2.986 | 0.4666 |
| 314 | 2.937 | 3.001 | 2.937 | 3.001 | 2.937 | 3.001 | 0.4726 |
| 315 | 2.953 | 3.028 | 2.953 | 3.028 | 2.953 | 3.028 | 0.4757 |
| 316 | 2.970 | 3.016 | 2.970 | 3.016 | 2.970 | 3.016 | 0.4761 |
| 317 | 2.963 | 3.060 | 2.963 | 3.060 | 2.963 | 3.060 | 0.4788 |
| 318 | 3.045 | 3.106 | 3.045 | 3.106 | 3.045 | 3.106 | 0.4879 |
| 319 | 3.038 | 3.147 | 3.038 | 3.147 | 3.038 | 3.147 | 0.4902 |
| 320 | 3.111 | 3.199 | 3.111 | 3.199 | 3.111 | 3.199 | 0.4990 |
| 321 | 3.161 | 3.250 | 3.161 | 3.250 | 3.161 | 3.250 | 0.5058 |
| 322 | 3.278 | 3.382 | 3.278 | 3.382 | 3.278 | 3.382 | 0.5224 |
| 323 | 3.295 | 3.415 | 3.295 | 3.415 | 3.295 | 3.415 | 0.5256 |

*FIG. 6A*

| 324 | 3.461 | 3.537 | 3.461 | 3.537 | 3.461 | 3.537 | 0.5439 |
| 325 | 3.551 | 3.654 | 3.551 | 3.654 | 3.551 | 3.654 | 0.5565 |
| 326 | 3.688 | 3.828 | 3.688 | 3.828 | 3.688 | 3.828 | 0.5749 |
| 327 | 3.776 | 3.918 | 3.776 | 3.918 | 3.776 | 3.918 | 0.5850 |
| 328 | 3.956 | 4.098 | 3.956 | 4.098 | 3.956 | 4.098 | 0.6049 |
| 329 | 4.173 | 4.320 | 4.173 | 4.320 | 4.173 | 4.320 | 0.6280 |
| 330 | 4.274 | 4.447 | 4.274 | 4.447 | 4.274 | 4.447 | 0.6395 |
| 331 | 4.442 | 4.590 | 4.442 | 4.590 | 4.442 | 4.590 | 0.6547 |
| 332 | 4.717 | 4.876 | 4.717 | 4.876 | 4.717 | 4.876 | 0.6808 |
| 333 | 4.993 | 5.179 | 4.993 | 5.179 | 4.993 | 5.179 | 0.7063 |
| 334 | 5.142 | 5.352 | 5.142 | 5.352 | 5.142 | 5.352 | 0.7198 |
| 335 | 5.496 | 5.676 | 5.496 | 5.676 | 5.496 | 5.676 | 0.7470 |
| 336 | 5.681 | 5.817 | 5.681 | 5.817 | 5.681 | 5.817 | 0.7596 |
| 337 | 6.021 | 6.254 | 6.021 | 6.254 | 6.021 | 6.254 | 0.7879 |
| 338 | 6.403 | 6.562 | 6.403 | 6.562 | 6.403 | 6.562 | 0.8117 |
| 339 | 6.660 | 6.837 | 6.660 | 6.837 | 6.660 | 6.837 | 0.8292 |
| 340 | 7.015 | 7.413 | 7.015 | 7.413 | 7.015 | 7.413 | 0.8580 |
| 341 | 7.467 | 7.816 | 7.467 | 7.816 | 7.467 | 7.816 | 0.8831 |
| 342 | 8.040 | 8.362 | 8.040 | 8.362 | 8.040 | 8.362 | 0.9138 |
| 343 | 8.403 | 8.758 | 8.403 | 8.758 | 8.403 | 8.758 | 0.9334 |
| 344 | 8.944 | 9.242 | 8.944 | 9.242 | 8.944 | 9.242 | 0.9586 |
| 345 | 9.403 | 9.881 | 9.403 | 9.881 | 9.403 | 9.881 | 0.9841 |
| 346 | 10.046 | 10.450 | 10.046 | 10.450 | 10.046 | 10.450 | 1.0106 |
| 347 | 10.556 | 10.943 | 10.556 | 10.943 | 10.556 | 10.943 | 1.0313 |
| 348 | 11.095 | 11.626 | 11.095 | 11.626 | 11.095 | 11.626 | 1.0553 |
| 349 | 11.747 | 12.225 | 11.747 | 12.225 | 11.747 | 12.225 | 1.0786 |
| 350 | 12.281 | 12.935 | 12.281 | 12.935 | 12.281 | 12.935 | 1.1005 |
| 351 | 12.983 | 13.631 | 12.983 | 13.631 | 12.983 | 13.631 | 1.1239 |
| 352 | 13.487 | 14.090 | 13.487 | 14.090 | 13.487 | 14.090 | 1.1394 |
| 353 | 14.164 | 14.852 | 14.164 | 14.852 | 14.164 | 14.852 | 1.1615 |
| 354 | 14.773 | 15.406 | 14.773 | 15.406 | 14.773 | 15.406 | 1.1786 |
| 355 | 15.180 | 15.938 | 15.180 | 15.938 | 15.180 | 15.938 | 1.1919 |
| 356 | 15.873 | 16.695 | 15.873 | 16.695 | 15.873 | 16.695 | 1.2116 |
| 357 | 16.530 | 17.381 | 16.530 | 17.381 | 16.530 | 17.381 | 1.2292 |
| 358 | 17.005 | 17.767 | 17.005 | 17.767 | 17.005 | 17.767 | 1.2401 |
| 359 | 17.718 | 18.572 | 17.718 | 18.572 | 17.718 | 18.572 | 1.2586 |
| 360 | 18.274 | 19.038 | 18.274 | 19.038 | 18.274 | 19.038 | 1.2707 |
| 361 | 18.786 | 19.517 | 18.786 | 19.517 | 18.786 | 19.517 | 1.2821 |
| 362 | 19.315 | 20.375 | 19.315 | 20.375 | 19.315 | 20.375 | 1.2975 |
| 363 | 19.929 | 20.916 | 19.929 | 20.916 | 19.929 | 20.916 | 1.3100 |
| 364 | 20.417 | 21.106 | 20.417 | 21.106 | 20.417 | 21.106 | 1.3172 |
| 365 | 20.634 | 21.826 | 20.634 | 21.826 | 20.634 | 21.826 | 1.3268 |
| 366 | 21.279 | 22.265 | 21.279 | 22.265 | 21.279 | 22.265 | 1.3378 |

*FIG. 6B*

| | | | | | | | |
|---|---|---|---|---|---|---|---|
| 367 | 21.632 | 22.762 | 21.632 | 22.762 | 21.632 | 22.762 | 1.3461 |
| 368 | 21.942 | 22.904 | 21.942 | 22.904 | 21.942 | 22.904 | 1.3506 |
| 369 | 22.479 | 23.390 | 22.479 | 23.390 | 22.479 | 23.390 | 1.3604 |
| 370 | 22.832 | 24.155 | 22.832 | 24.155 | 22.832 | 24.155 | 1.3708 |
| 371 | 22.802 | 23.876 | 22.802 | 23.876 | 22.802 | 23.876 | 1.3680 |
| 372 | 22.958 | 24.196 | 22.958 | 24.196 | 22.958 | 24.196 | 1.3723 |
| 373 | 23.130 | 24.389 | 23.130 | 24.389 | 23.130 | 24.389 | 1.3757 |
| 374 | 23.331 | 24.460 | 23.331 | 24.460 | 23.331 | 24.460 | 1.3782 |
| 375 | 23.635 | 24.634 | 23.635 | 24.634 | 23.635 | 24.634 | 1.3825 |
| 376 | 23.461 | 24.857 | 23.461 | 24.857 | 23.461 | 24.857 | 1.3829 |
| 377 | 23.547 | 24.658 | 23.547 | 24.658 | 23.547 | 24.658 | 1.3819 |
| 378 | 23.579 | 24.974 | 23.579 | 24.974 | 23.579 | 24.974 | 1.3850 |
| 379 | 23.614 | 24.852 | 23.614 | 24.852 | 23.614 | 24.852 | 1.3843 |
| 380 | 23.801 | 24.880 | 23.801 | 24.880 | 23.801 | 24.880 | 1.3862 |
| 381 | 23.377 | 24.503 | 23.377 | 24.503 | 23.377 | 24.503 | 1.3790 |
| 382 | 23.193 | 24.415 | 23.193 | 24.415 | 23.193 | 24.415 | 1.3765 |
| 383 | 23.146 | 24.229 | 23.146 | 24.229 | 23.146 | 24.229 | 1.3744 |
| 384 | 22.855 | 23.788 | 22.855 | 23.788 | 22.855 | 23.788 | 1.3677 |
| 385 | 22.435 | 23.521 | 22.435 | 23.521 | 22.435 | 23.521 | 1.3612 |
| 386 | 22.129 | 23.241 | 22.129 | 23.241 | 22.129 | 23.241 | 1.3556 |
| 387 | 21.832 | 22.763 | 21.832 | 22.763 | 21.832 | 22.763 | 1.3482 |
| 388 | 21.346 | 22.406 | 21.346 | 22.406 | 21.346 | 22.406 | 1.3398 |
| 389 | 20.874 | 21.951 | 20.874 | 21.951 | 20.874 | 21.951 | 1.3305 |
| 390 | 20.546 | 21.445 | 20.546 | 21.445 | 20.546 | 21.445 | 1.3220 |
| 391 | 20.006 | 20.969 | 20.006 | 20.969 | 20.006 | 20.969 | 1.3114 |
| 392 | 19.486 | 20.488 | 19.486 | 20.488 | 19.486 | 20.488 | 1.3006 |
| 393 | 19.095 | 19.960 | 19.095 | 19.960 | 19.095 | 19.960 | 1.2905 |
| 394 | 18.524 | 19.501 | 18.524 | 19.501 | 18.524 | 19.501 | 1.2789 |
| 395 | 18.138 | 19.054 | 18.138 | 19.054 | 18.138 | 19.054 | 1.2693 |
| 396 | 17.704 | 18.475 | 17.704 | 18.475 | 17.704 | 18.475 | 1.2573 |
| 397 | 17.042 | 17.905 | 17.042 | 17.905 | 17.042 | 17.905 | 1.2423 |
| 398 | 16.492 | 17.283 | 16.492 | 17.283 | 16.492 | 17.283 | 1.2275 |
| 399 | 16.011 | 16.649 | 16.011 | 16.649 | 16.011 | 16.649 | 1.2129 |
| 400 | 15.443 | 16.084 | 15.443 | 16.084 | 15.443 | 16.084 | 1.1976 |

*FIG. 6C*

IMINO COMPOUNDS AS PROTECTING AGENTS AGAINST ULTRAVIOLET RADIATIONS

CROSS-REFERENCE TO RELATED APPLICATIONS

The present application claims the benefit of priority to PCT International Application No. PCT/CA13/0536 filed May 31, 2013, which claims the benefit of priority to U.S. provisional patent application No. 61/655,115, filed Jun. 4, 2012; each of which is incorporated herein by reference in its entirety.

I. RELATED TECHNOLOGICAL FIELD

The present invention relates to compounds that absorb ultraviolet radiations and that protect biological materials as well as non-biological materials from damaging exposure to ultraviolet radiations. The present invention also relates to formulations and compositions comprising such compounds for use in absorbing ultraviolet radiations and in protecting biological materials as well as non-biological materials against ultraviolet radiations. The present invention also relates to methods for protecting biological materials as well as non-biological materials from damaging exposure to ultraviolet radiations.

II. BACKGROUND

Commercially available ultraviolet blocking agents typically include compounds such as para-aminobenzoic acid derivatives, benzotriazoles, benzophenones, methoxycinnamates and salicylates. Mycosporine-like amino acids (MAAs) have also been identified as ultraviolet-absorbing agents. MAAs are small molecules of about 400 Da produced by organisms that live in environments with high volumes of sunlight, typically marine environments[1]. The structures of over 30 MAAs have been resolved and they contain a central cyclohexenone or cyclohexenimine ring as well as a wide variety of substitutions. The ring structure is thought to absorb ultraviolet light and accommodate free radicals[2]. MAAs absorb ultraviolet light, typically between 310 nm and 360 nm. It is this light absorbing property that allows MAAs to protect cells from harmful ultraviolet radiation. Biosynthetic pathways of specific MAAs depend on the specific MAA and the organism that is producing it. These biosynthetic pathways often share common enzymes and intermediates with other major biosynthetic pathways.

Useful ultraviolet absorbing agents such as the ones mentioned above must meet various criteria including stability, acceptable permanence, efficacy, compatibility with the media with which they are to be mixed or be incorporated into, non-toxicity and not harmful to the surface onto which they are to be applied. These criteria limit the choice of ultraviolet protecting agents available to be used in various applications. Therefore, there remains a need in the art for additional agents that meet these criteria, that absorb ultraviolet radiations and that protect biological and non-biological materials against the harmful damages caused by ultraviolet radiations and that are easy to prepare.

III. SUMMARY

According to one aspect, the present invention relates to a compound having the Formula I:

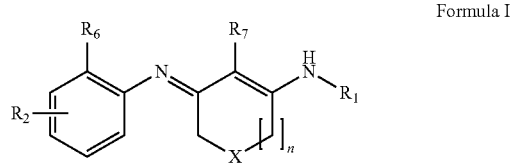

Formula I or an acceptable salt thereof; wherein $R_1$ is unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; arylalkyl; carboxyl; heteroaryl; heteroarylalkyl; phenyl; benzyl; hydroxyl; carboxylic acid; ester; sulfonyl; sulfhydryl; sulfide; sulfonyl; sulfino; phosphino; phosphono; phosphate; amine; halo; or carboxamide; $R_2$ is hydrogen, halo, unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; hydroxyl; halo; phenyl; benzyl; carboxylic acid or ester groups; $R_6$ and $R_7$ are each independently hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; halo group; phosphono group; ester group; carboxylic acid group; phenyl group; alkyl fatty acid chain or polyether; X is carbon; halo; nitrogen; oxygen; sulfur; —$CH_2$; phenyl group; cycloakyl group; amino group or spirocyclic alkanes; and n is an integer, wherein the integer is 1, 2, 3 or 4.

According to another aspect, the present invention relates to a UV-absorbing composition comprising: the compound as defined herein; one or more UV-blocking agent; and one or more suitable additives.

According to another aspect, the present invention relates to the use of the compound as defined herein, in the preparation of a composition for protecting a biological material against UV radiation and/or in the preparation of a composition for protecting a non-biological material against UV radiation.

According to another aspect, the present invention relates to a method for protecting a surface of a biological material and/or a non-biological material against UV radiation, comprising applying to the surface the composition as defined herein.

According to another aspect, the present invention relates to a compound having the formula:

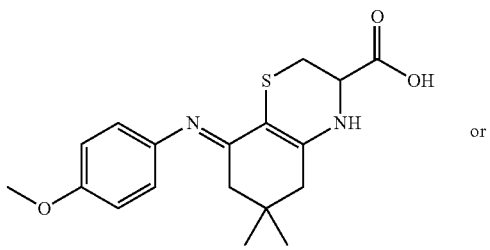

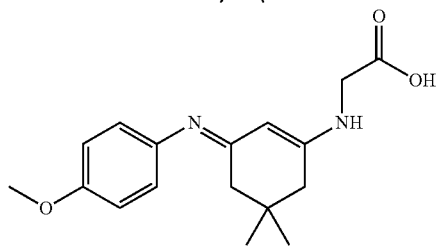

for use in protecting textiles against UV radiations.

According to another aspect, the present invention relates to a compound having the formula:

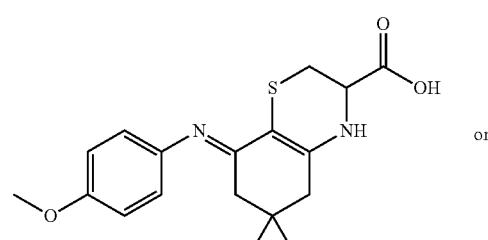

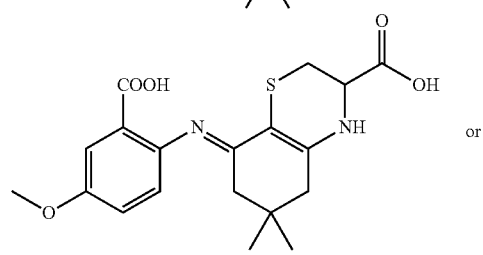

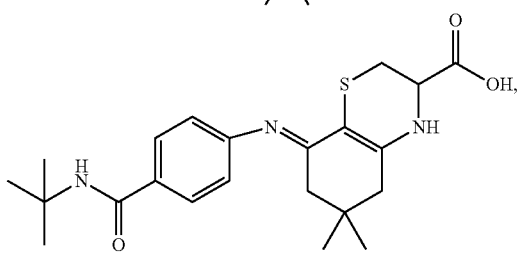

for use in preparation of compositions for protecting against UV radiations.

IV. BRIEF DESCRIPTION OF THE FIGURES

FIG. 2 is a table showing the UV-transmittance at the indicated wavelength for compound $IF_1$.

FIG. 3 is a table showing the UV-transmittance at the indicated wavelength for compound $IA_1$.

FIG. 4 is a table showing the UV-transmittance at the indicated wavelength for compound $IA_2$.

FIG. 5 is a table showing the UV-transmittance at the indicated wavelength for compound $IE_4$.

FIG. 6 is a table showing the UV-transmittance at the indicated wavelength for compound $IE_1$.

V. DESCRIPTION

A) Definitions

Figure 1:
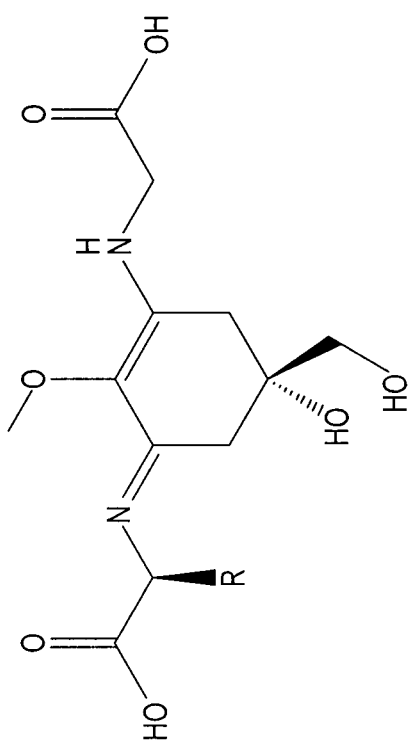
FIG. 1 is a schematic representation of the general structure of mycosporine molecules.

The terms "comprising" and "including", as used herein, unless otherwise indicated, are used in their open, non-limiting sense.

As used herein, the terms "compound" and "compound(s) of the invention" are used interchangeably to refer to any compounds, including acceptable salts, hydrates or solvates thereof, disclosed herein specifically or generically. In one embodiment, the compounds of the invention are compounds of formula I or variants of formula I and pharmaceutically acceptable salts, hydrates or solvates thereof.

The expression "biological materials", as used herein, unless otherwise indicated, is intended to include humans, animals and plants and includes for example: cells, hair, skin, as well as other human and animal tissues. The expression "non-biological materials", as used herein, unless otherwise indicated, is intended to include all things that do not fall into the definition of "biological materials".

The expression "solar radiation", as used herein, unless otherwise indicated, is intended to include the total frequency spectrum of electromagnetic radiation given off by the sun, including radio waves, x-rays, infrared, visible, and ultraviolet ("UV").

The terms "ultraviolet" and "UV", as used herein, unless otherwise indicated, are intended to mean ultraviolet or ultraviolet light. UV is electromagnetic radiation with a wavelength shorter than that of visible light, but longer than X-rays, in the range of about 10 nm to about 400 nm, and energies from about 3 eV to about 124 eV (the abbreviation "eV", herein refers to electron volts). Ultraviolet A (UVA) refers to UV radiation in the spectrum of between 320-400 nm, it is also referred to as "longer" rays. The UVA waveband is further divided into UVA I (340-400 nm) and UVA II (320-340 nm). UVA are the principal cause of long term skin damage due to sun and may also contribute to sunburn. Ultraviolet B (UVB) refers to radiation in the spectrum of 290-320 nm, it is also referred to as "shorter" rays. UVB rays are the principal cause of sunburn due to sun exposure.

The term "imine" or "imino", as used herein, unless otherwise indicated, includes a functional group or chemical compound containing a carbon-nitrogen double bond. The expression "imino compound", as used herein, unless otherwise indicated, refers to a compound that includes an "imine" or an "imino" group as defined herein.

The term "hydroxyl", as used herein, unless otherwise indicated, includes —OH.

The terms "halogen" and "halo", as used herein, unless otherwise indicated, include a chlorine, chloro, Cl; fluorine, fluoro, F; bromine, bromo, Br; or iodine, iodo, I.

The term "aryl", as used herein, unless otherwise indicated, include a carbocyclic aromatic group. Examples of aryl groups include, but are not limited to, phenyl, benzyl, naphthyl and anthracenyl.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group.

The term "alkyl", as used herein, unless otherwise indicated, includes saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl.

The term "carboxyl", as used herein, unless otherwise indicated, includes a functional group consisting of a carbon atom double bonded to an oxygen atom and single bonded to a hydroxyl group (—COOH).

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "acyl", as used herein, unless otherwise indicated, includes a functional group derived from an aliphatic carboxylic acid, by removal of the hydroxyl (—OH) group.

The term "alkoxyl", as used herein, unless otherwise indicated, includes O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl and —O—$(CH_2)_2$-cyclodecyl.

The term "cycloalkyl", as used herein, unless otherwise indicated, includes a non-aromatic, saturated or partially saturated, monocyclic or fused, spiro or unfused bicyclic or tricyclic hydrocarbon referred to herein containing a total of from 3 to 10 carbon atoms, preferably 3 to 8 ring carbon atoms. Examples of cycloalkyls include, but are not limited to, $C_3$-$C_8$ cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

The term "cycloalky" also includes -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl and —$CH_2$-cyclooctyl.

The term "heterocyclic", as used herein, unless otherwise indicated, includes an aromatic or non-aromatic cycloalkyl in which one to four of the ring carbon atoms are independently replaced with a heteroatom from the group consisting of O, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl and tetrazolyl. Heterocycles can be substituted or unsubstituted. Heterocycles can also be bonded at any ring atom (i.e., at any carbon atom or heteroatom of the heterocyclic ring).

The term "cyano", as used herein, unless otherwise indicated, includes a —CN group.

The term "alcohol", as used herein, unless otherwise indicated, includes a compound in which the hydroxyl functional group (—OH) is bound to a carbon atom. In particular, this carbon center should be saturated, having single bonds to three other atoms.

The term "solvate" is intended to mean a solvate form of a specified compound that retains the effectiveness of such compound. Examples of solvates include compounds of the invention in combination with, for example: water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

The term "mycosporine", as used herein, is a general term for compounds that exhibit the general structure shown in FIG. 1. Mycosporines have a central ring structure with various amino groups modifying this ring structure (including for example, a central cyclohexenone or cyclohexenimine ring and a wide variety of substitutions). Mycosporine-like amino acids ("MAAs") represent a relatively broad class of water-soluble substituted cyclohexenes that are linked to amino acids and imino alcohols and have absorption maxima between about 310 and about 360 nm[3-6]. In some marine organisms MAAs act as photo-protective UV filters and/or as antioxidants. In vitro studies have demonstrated the elevated photostability of MAAs as well as the release of heat to the medium as a result of the relaxation pathway of photo-excited molecules. The results of these studies provide strong evidence that MAAs also function as UV filters and/or antioxidants in vitro[7]. The term mycosporine in this application includes both a single species of mycosporine compound and a mixture of several mycosporines. All of the compounds commonly referred to as mycosporine are included within the scope of the invention. Typical MAAs include, but are not limited to: mycosporine-glycine, mycosporine-taurine, palythine, asterina-330, palythinol, palythene, porphyra-334, mycosporine-glycine:valine, shinorine and MAA 357.

B) Compounds of the Invention

MAAs from marine organisms are imine derivatives of mycosporines which contain an amino-cyclohexenimine ring linked to an amino acid, amino alcohol or amino group[8]. We have proposed that certain groups of chemical and structural derivative compounds of MAAs may be readily synthetically prepared and may demonstrate solar radiation-absorbing characteristics, UV-protection properties as well as anti-oxidants properties. Such as for MAAs, these compounds potentially share the mechanism of action of absorbing light, more particularly of absorbing UV radiations; more particularly of absorbing UVA and/or UVB radiations. Also, such as some MAAs, these compounds potentially share the anti-oxidant properties. We have obtained compounds that comprise at least one imino group. These compounds are capable electron delocalization and of UV radiations absorption. Particularly, we have obtained compounds that have UV-absorbing (such as UVA-absorbing and/or UVB-absorbing properties) and/or antioxidant properties.

Accordingly, in one embodiment, the present invention relates to compounds of the general Formula I:

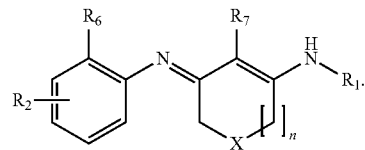

Formula I

Compounds having general Formula I can absorb UV radiation through their ring structure. It should therefore be the UV absorbing property that allows the compounds defined herein to protect from UV radiations. In some implementations of this embodiment, the compounds of Formula I can accommodate free radicals through their ring structure (e.g., electron delocalization capacity). In some other implementations, the compounds of Formula I can protect from oxidative damage.

In some implementations of this embodiment, the compounds of general Formula I may comprise more than one imino group.

The compounds of the present invention are therefore potentially useful in absorbing UV radiations and in blocking UV radiations from penetrating the surface of biological as well as non-biological materials. These compounds are also potentially useful in inhibiting or reducing the effects of UV in biological and non-biological materials. Some of the effects of UV radiations that may be useful to inhibit or to reduce are the harmful effects of UV radiations. On biological materials such as humans and animals, some harmful effects of UV radiations include, but are not limited to: sunburn, skin diseases, aggravation of skin diseases, damage to the eyes, indirect DNA damage, melanoma and cancer. On non-biological materials such as on articles of manufacture, some harmful effects of UV radiations include, but are not limited to: degradation of polymers, degradation of pigments, degradation of color, color fastness, degradation of dyes, weakening of structure, drying, etc.

In another implementation of this embodiment, there is provided compounds of the general Formula I:

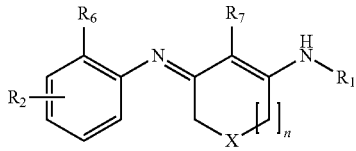

Formula I or an acceptable or suitable salt or solvate thereof; wherein:

$R_1$ is unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; arylalkyl; carboxyl; heteroaryl; heteroarylalkyl; phenyl; benzyl; hydroxyl; carboxylic acid; ester; sulfinyl; sulfhydryl; sulfide; sulfonyl; sulfino; phosphino; phosphono; phosphate; amine; halo; or carboxamide. In some implementations, $R_1$ may form a heterocycle with other elements of the compound and/or other ring elements of the compound. In some of these implementations, $R_1$ may, for example, form a heterocycle with $R_7$. The resulting heterocycle may be unsubstituted or may comprise one or more substituents. As a result of this heterocyclization, $R_7$ is replaced by Y as defined below.

$R_6$ and $R_7$ are each independently hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; halo group; phosphono group; ester group; carboxylic acid group; phenyl group; alkyl fatty acid chain or polyether.

$R_2$ is hydrogen; halo; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; hydroxyl; halo; phenyl; benzyl; carboxylic acid or ester groups. In some implementations, the double bond of the aromatic ring structure as depicted in Formula I may be replaced by two $R_2$ groups as schematized in the variant of Formula I here below:

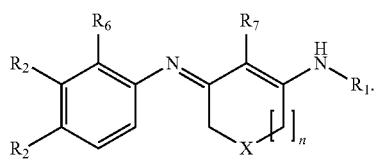

Variant of Formula I

X is carbon; halo; nitrogen; oxygen; sulfur; —CH$_2$; phenyl; cycloakyl; amino or spirocyclic alkanes. In some implementations, X may have one or more substituents.

n is an integer, wherein the integer is 1, 2, 3 or 4.

A person skilled in the art will appreciate that several structural variations in general Formula I may be considered without departing from the present invention.

In some implementations of the present embodiment, examples of compounds having the general Formula I include, but are not limited to, compounds having the sub-general Formula IA, IB, IC, ID, IE or IF as discussed below.

The sub-general structure of compounds of Formula IA is depicted here below:

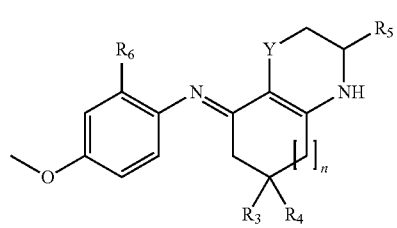

Formula IA wherein:

$R_3$ and $R_4$ are each independently hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; hydroxyl group; phosphono group; ester group; carboxylic acid group; or a phenyl group.

$R_5$ is unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; hydroxyl; a phosphono group; an ester group; a carboxylic acid group; or a phenyl group.

$R_6$ is hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; hydroxyl; sulfo group; halo group; phosphono group; ester group; carboxylic acid group; phenyl group; alkyl fatty acid chain or polyether.

Y is carbon; oxygen; sulfur; —CH$_2$; phenyl group; amine group; or spirocyclic alkanes.

n is an integer, wherein the integer is 1, 2, 3 or 4.

A person skilled in the art will appreciate that several structural variations in general Formula IA may be considered without departing from the present invention. In some implementations of this embodiment, compounds having sub-general Formula IA, include, but are not limited to:

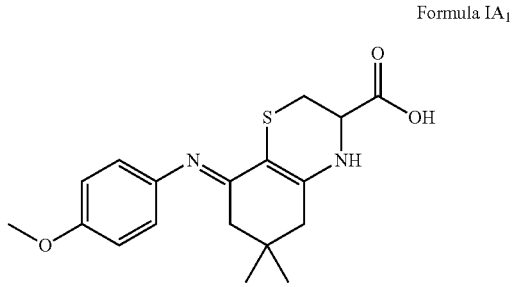

Formula IA$_1$ (R,E)-8-(4-methoxyphenylimino)-6,6-dimethyl-3,4,5,6,7,8-hexahydro-2H-benzo[b][1,4]thiazine-3-carboxylic Formula IA₂

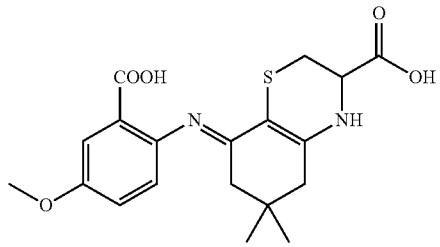

(R,E)-8-(2-carboxy-4-methoxyphenylimino)-6,6-dimethyl-3,4,5,6,7,8-hexahydro-2H-benzo[b][1,4]thiazine-3-carboxylic acid Formula IA₃

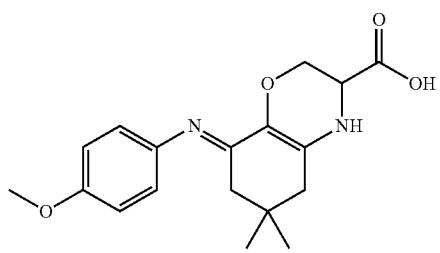

(R,E)-8-(4-methoxyphenylimino)-6,6-dimethyl-3,4,5,6,7,8-hexahydro-2H-benzo[b][1,4]oxazine-3-carboxylic acid Formula IA₄

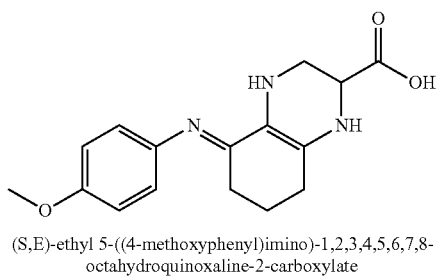

(E)-5-(4-methoxyphenylimino)-7,7-dimethyl-1,2,3,4,5,6,7,8-octahydroquinoxaline-2-carboxylic acid Formula IA₅

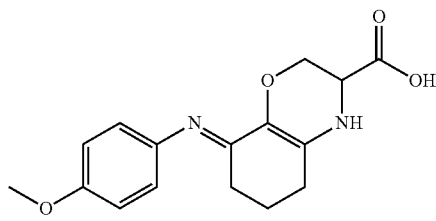

(S,E)-ethyl 8-((4-methoxyphenyl)imino)-3,4,5,6,7,8-hexahydro-2H-benzo[b][1,4]oxazine-3-carboxylate Formula IA₆

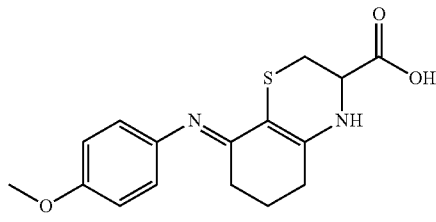

(R,E)-ethyl 8-((4-methoxyphenyl)imino)-3,4,5,6,7,8-hexahydro-2H-benzo[b][1,4]thiazine-3-carboxylate Formula IA₇

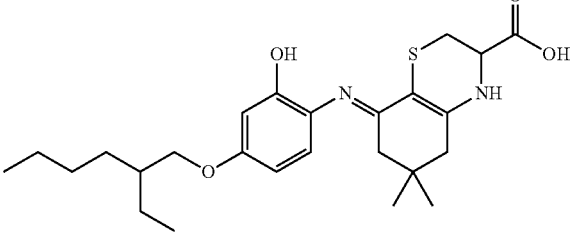

(S,E)-ethyl 5-((4-methoxyphenyl)imino)-1,2,3,4,5,6,7,8-octahydroquinoxaline-2-carboxylate Formula IA₈

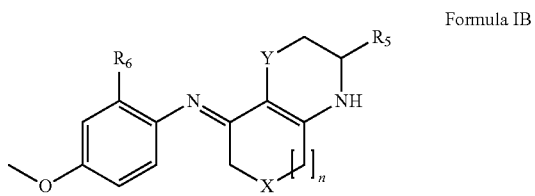

(R,E)-8-(4-(2-ethylhexyloxy)-2-hydroxyphenylimino)-6,6-dimethyl-3,4,5,6,7,8-hexahydro-2H-benzo[b][1,4]thiazine-3-carboxylic acid The sub-general structure of compounds of Formula IB is depicted here below:

Formula IB wherein:

$R_5$ is unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; a phosphono group; an ester group; a carboxylic acid group; hydroxyl; or a phenyl group.

$R_6$ is hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; halo group; phosphono group; ester group; carboxylic acid group; phenyl group; alkyl fatty acid chain or polyether.

Y is carbon; oxygen; sulfur; —CH₂; phenyl group; amine group; or spirocyclic alkanes.

X is oxygen; sulfur; aryl; phenyl group; spirocyclic alkanes; or amino group.

n is an integer, wherein the integer is 1, 2, 3 or 4.

A person skilled in the art will appreciate that several structural variations in general Formula IB may be considered without departing from the present invention. Examples of compounds having sub-general Formula IB include, but are not limited to:

Formula IB₁

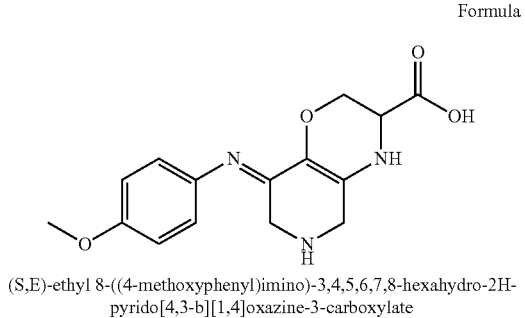

(S,E)-ethyl 8-((4-methoxyphenyl)imino)-3,4,5,6,7,8-hexahydro-2H-pyrido[4,3-b][1,4]oxazine-3-carboxylate Formula IB₂

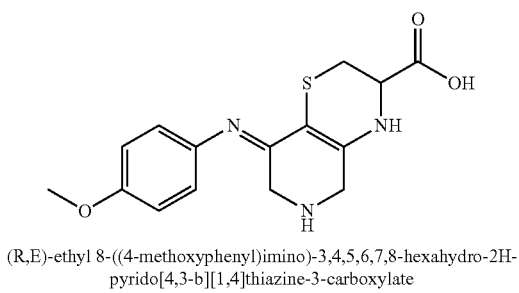

(R,E)-ethyl 8-((4-methoxyphenyl)imino)-3,4,5,6,7,8-hexahydro-2H-pyrido[4,3-b][1,4]thiazine-3-carboxylate Formula IB₃

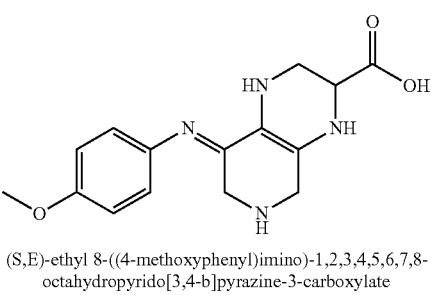

(S,E)-ethyl 8-((4-methoxyphenyl)imino)-1,2,3,4,5,6,7,8-octahydropyrido[3,4-b]pyrazine-3-carboxylate Formula IB₄

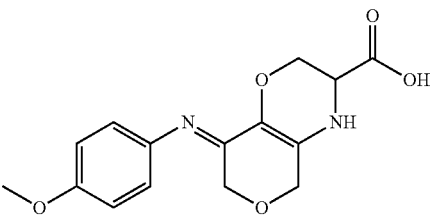

(S,E)-ethyl 8-((4-methoxyphenyl)imino)-2,3,4,5,6,7,8-hexahydropyrano[4,3-b][1,4]oxazine-3-carboxylate Formula IB₅

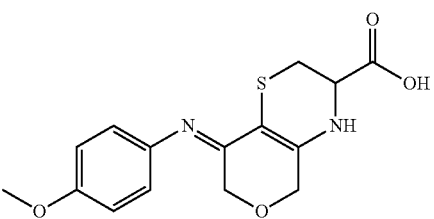

(R)-ethyl 8-((4-methoxyphenyl)imino)-2,3,4,5,6,7,8-hexahydropyrano[4,3-b][1,4]thiazine-3-carboxylate Formula IB₆

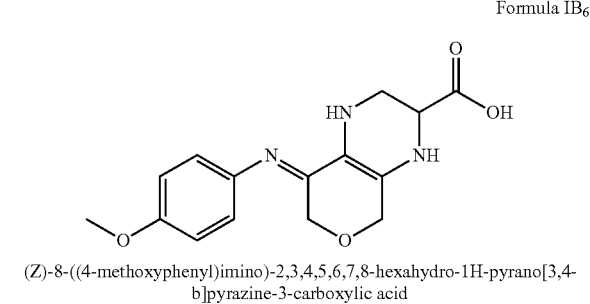

(Z)-8-((4-methoxyphenyl)imino)-2,3,4,5,6,7,8-hexahydro-1H-pyrano[3,4-b]pyrazine-3-carboxylic acid The sub-general structure of compounds of Formula IC is depicted here below:

Formula IC

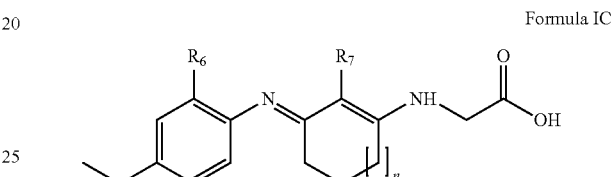

wherein:

$R_6$ and $R_7$ are hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; halo group; phosphono group; ester group; carboxylic acid group; phenyl group; hydroxyl; alkyl fatty acid chain or polyether.

X is oxygen; sulfur; aryl; phenyl group; spirocyclic alkanes; or amino group.

n is an integer, wherein the integer is selected from 1, 2, 3 or 4.

A person skilled in the art will appreciate that several structural variations in general Formula IC may be considered without departing from the present invention. Examples of compounds having sub-general Formula IC include, but are not limited to:

Formula IC₁

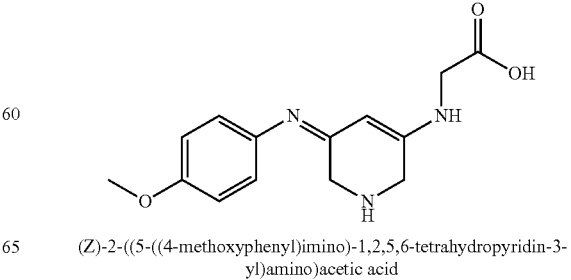

(Z)-2-((5-((4-methoxyphenyl)imino)-1,2,5,6-tetrahydropyridin-3-yl)amino)acetic acid Formula IC₂

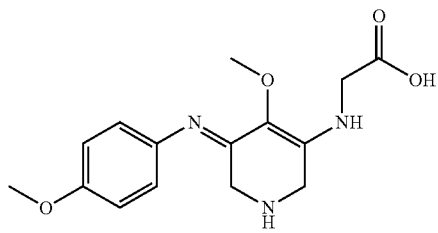

(E)-2-((4-methoxy-5-((4-methoxyphenyl)imino)-1,2,5,6-tetrahydropyridin-3-yl)amino)acetic acid Formula IC₃

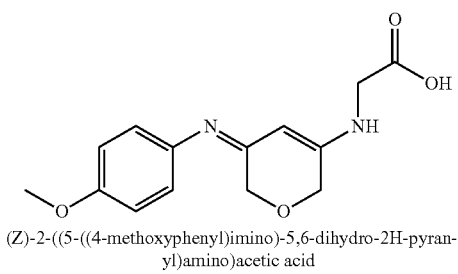

(Z)-2-((5-((4-methoxyphenyl)imino)-5,6-dihydro-2H-pyran-3-yl)amino)acetic acid

Formula IC₄

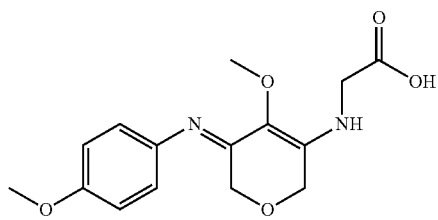

(E)-2-((4-methoxy-5-((4-methoxyphenyl)imino)-5,6-dihydro-2H-pyran-3-yl)amino)acetic acid The sub-general structure of compounds of Formula ID is depicted here below:

Formula ID

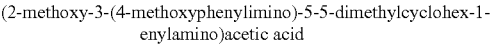

wherein:

$R_3$ and $R_4$ are each independently hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; phosphono group; ester group; hydroxyl; carboxylic acid group; or a phenyl group.

$R_6$ and $R_7$ are hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; halo group; phosphono group; ester group; carboxylic acid group; phenyl group; alkyl fatty acid chain or polyether.

n is an integer, wherein the integer is 1, 2, 3 or 4.

A person skilled in the art will appreciate that several structural variations in general Formula ID may be considered without departing from the present invention. Examples of compounds having Formula ID include:

Formula ID₁

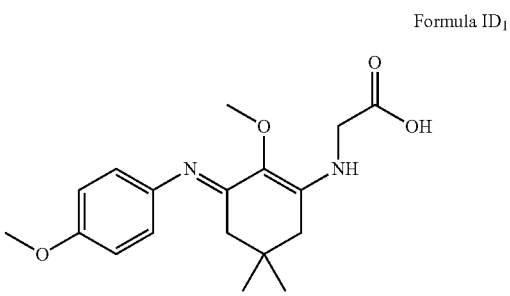

(E)-2-(2-methoxy-3-(4-methoxyphenylimino)-5-5-dimethylcyclohex-1-enylamino)acetic acid Formula ID₂

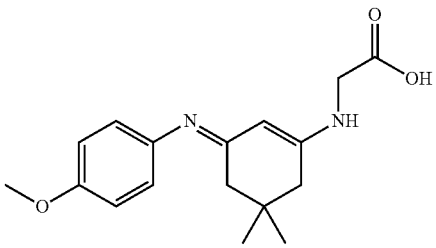

(E)-2-(3-(4-methoxyphenylimino)-5,5-dimethylcyclohex-1-enylamino)acetic acid

Formula ID₃

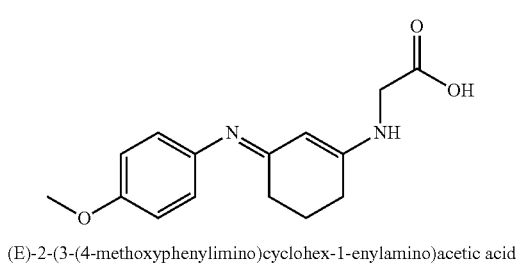

(E)-2-(3-(4-methoxyphenylimino)cyclohex-1-enylamino)acetic acid

Formula ID₄

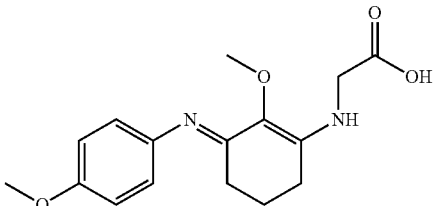

(E)-2-(2-methoxy-3-(4-methoxyphenylimino)cyclohex-1-enylamino)acetic acid

The sub-general structure of compounds of Formula IE is depicted here below:

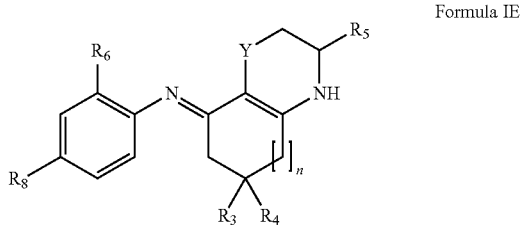

Formula IE wherein:

R₃ and R₄ are each independently hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; phosphono group; hydroxyl; ester group; carboxylic acid group; or a phenyl group.

R₅ is unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; a phosphono group; hydroxyl; an ester group; a carboxylic acid group; or a phenyl group.

R₆ is hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; hydroxyl; halo group; phosphono group; ester group; carboxylic acid group; phenyl group; alkyl fatty acid chain or polyether.

R₈ is hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; halo group; phosphono group; ester group; carboxylic acid group; phenyl group; amine group; alkyl fatty acid chain or polyether.

Y is carbon; oxygen; sulfur; —CH₂; phenyl group; amine group; or spirocyclic alkanes.

n is an integer, wherein the integer is 1, 2, 3 or 4.

A person skilled in the art will appreciate that several structural variations in general Formula IE may be considered without departing from the present invention. In some implementations of this embodiment, examples of compounds having sub-general Formula IE, include, but are not limited to:

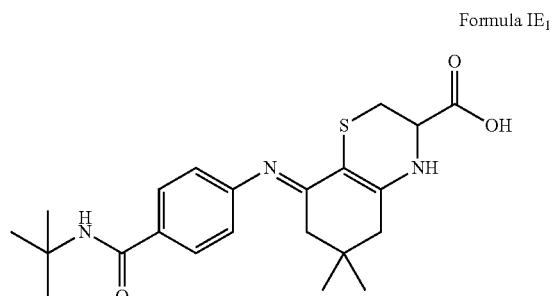

Formula IE₁

(R,E)-8-(4-(tert-butylcarbamoyl)phenylimino)-6,6-dimethyl-3,4,5,6,7,8-hexahydro-2H-benzo[b][1,4]thiazine-3-carboxylic acid

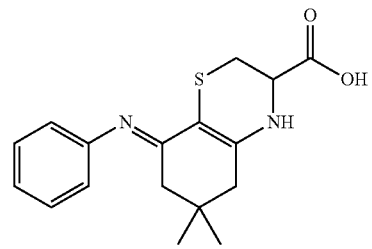

Formula IE₂

(R,E)-8-(phenylimino)-6,6-dimethyl-3,4,5,6,7,8-hexahydro-2H-benzo[b][1,4]thiazine-3-carboxylic acid

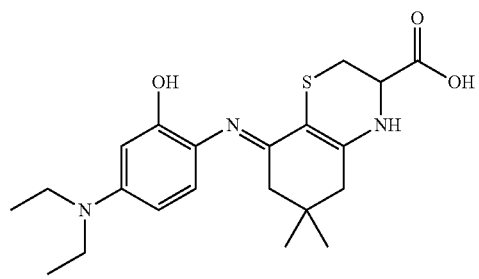

Formula IE₃

(R,E)-8-(4-(diethylamino)-2-hydrophenylimino)-6,6-dimethyl-3,4,5,6,7,8-hexahydro-2H-benzo[b][1,4]thiazine-3-carboxylic acid

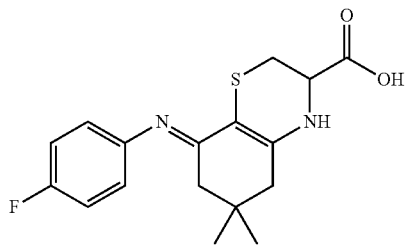

Formula IE₄

(R,E)-8-(fluorophenylimino)-6,6-dimethyl-3,4,5,6,7,8-hexahydro-2H-benzo[b][1,4]thiazine-3-carboxylic acid The sub-general structure of compounds of Formula IF is depicted here below:

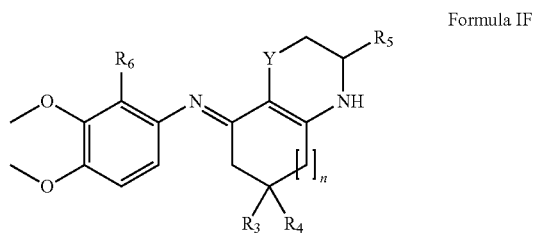

Formula IF wherein:

R₃ and R₄ are each independently hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; sulfo group; phosphono group; hydroxyl; ester group; carboxylic acid group; or a phenyl group.

R₅ is unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; hydroxyl; sulfo group; a phosphono group; an ester group; a carboxylic acid group; or a phenyl group.

R₆ is hydrogen; unsubstituted or substituted alkyl; unsubstituted or substituted alkenes; unsubstituted or substituted alkynes; unsubstituted or substituted aryl; unsubstituted or substituted heterocycle; unsubstituted or substituted cycloalkyl; unsubstituted and substituted alkoxy; alkanoyl; alkynyl; hydroxyl; sulfo group; hydroxyl; halo group; phosphono group; ester group; carboxylic acid group; phenyl group; alkyl fatty acid chain or polyether.

Y is carbon; oxygen; sulfur; —CH₂; phenyl group; amine group; or spirocyclic alkanes.

n is an integer, wherein the integer 1, 2, 3 or 4.

A person skilled in the art will appreciate that several structural variations in general Formula IF may be considered without departing from the present invention.

In some implementations of this embodiment, examples of compounds having sub-general Formula IF, include, but are not limited to:

Formula IF₁

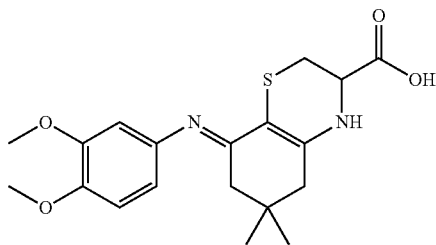

(R,E)-8-(3,4-dimethoxyphenylimino)-6,6-dimethyl-3,4,5,6,7,8-hexahydro-2H-benzo[b][1,4]thiazine-3-carboxylic acid When the groups described herein are said to be "unsubstituted or substituted" when substituted, they may be substituted with any desired substituent or substituents that do not adversely affect the desired activity of the compound. Examples of preferred substituents are those found in the exemplary compounds and embodiments disclosed herein, as well as halogen; alkyl; alkenyl; alkynyl; hydroxyl; alkoxyl; amino; nitro; thiol; thioether; imine; cyano; amido; phosphonato; phosphine; carboxyl; thiocarbonyl; sulfonyl; sulfonamide; ketone; aldehyde; ester; acetyl; acetoxy; carbamoyl; oxygen (═O); haloalkyl (e.g., trifluoromethyl); substituted aminoacyl and aminoalkyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; amyl-lower alkyl; —CO₂CH₃; —CONH₂; —OCH₂CONH₂; —NH₂; —SO₂NH₂; —OCHF₂; —CF₃; —OCF₃; and such moieties may also be optionally substituted by a fused-ring structure or bridge, for example —OCH₂O— or —O-lower alkyl-O—. These substituents may optionally be further substituted with a substituent selected from such groups. In one embodiment, when a lower alkyl group (e.g., methylene) is substituted, it is substituted with the side chain of a naturally occurring amino acid.

Other compounds of general Formula I include, but are not limited to, compounds having the following structures:

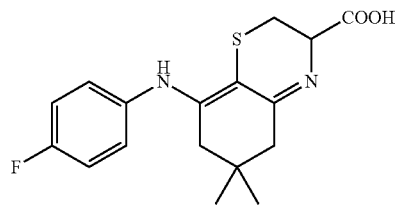

(R,E)-8-((4-fluorophenyl)imino)-6,6-dimethyl-3,4,5,6,7,8-hexahydro-2H-benzo[b][1,4]thiazine-3-carboxylic acid

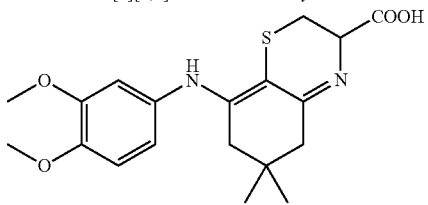

(R,E)-8-((3,4-dimethoxyphenyl)imino)-6,6-dimethyl-3,4,5,6,7,8-hexahydro-2H-benzo[b][1,4]thiazine-3-carboxylic acid

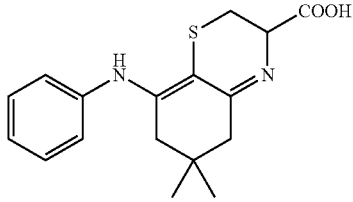

(R,E)-6,6-dimethyl-8-(phenylimino)-3,4,5,6,7,8-hexahydro-2H-benzo[b][1,4]thiazine-3-carboxylic acid

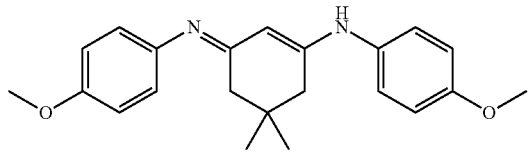

(E)-4-methoxy-N-(3-((4-methoxyphenyl)amino)-5,5-dimethylcyclohex-2-en-1-ylindene)aniline

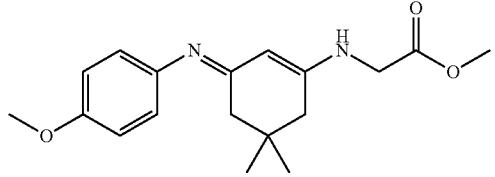

(E)-methyl 2-((3-((4-methoxyphenyl)imino)-5,5-dimethylcyclohex-1-en-1-yl)amino)acetate In a further embodiment of the present invention, there are provided methods and processes for the preparation of the compounds defined herein. The compounds of the present invention can be made using conventional organic syntheses. A person skilled in the art will appreciate that several variations in the methods and processes for preparing the compounds defined herein may be considered without departing from the present invention.

In one implementation of this embodiment, the compounds of general Formula I, may generally be derived via a diketone, more specifically, via a cyclic diketone, even more specifically, via an halogenated cyclic diketone. For example, the compound of sub-general Formula I may generally be derived via a cyclic diketone such as, but not limited to, cyclohexanedione (e.g., 5,5-dimethyl-cyclohexane-1,3-dione; 1,3-cyclohexanedione; 5-phenyl-1,3-cyclohexadione), cycloheptadione (e.g., 1,3-cycloheptadione), cyclopentadione (e.g., 1,3-cyclopentadione) or indadione (e.g., 1,3-indandione).

For example, the compound of Formula IA₁ may be prepared from 5,5-dimethyl-cyclohexane-1,3-dione. The preparation of the compound of Formula IA, from 5,5-dimethyl-cyclohexane-1,3-dione may be carried out by halogenation of 5,5-dimethyl-cyclohexane-1,3-dione in the presence of a suitable solvent to yield an halogenated 5,5-dimethyl-cyclohexane-1,3-dione. The halogenated 5,5-dimethyl-cyclohexane-1,3-dione may then be reacted with an ethyl ester to yield a benzothiazine intermediate compound. The benzothiazine intermediate compound may then be reacted with a methoxyalinine compound to yield the compound of Formula IA₁.

According to another implementation of this embodiment, preparation of the compound of Formula IA₁ from 5,5-dimethyl-cyclohexane-1,3-dione may be carried out as set out in the below synthetic scheme, wherein 5,5-dimethyl-cyclohexane-1,3-dione (1) is brominated in the presence of dichloromethane (DCM) to yield 2-bromo-5,5-dimethyl-cyclohexane-1,3-dione (2). The 2-bromo-5,5-dimethyl-cyclohexane-1,3-dione (2) is then reacted with L-cysteine ethyl ester HCl and pyridine to yield (R)-ethyl 6,6-dimethyl-8-oxo-3,4,5,6,7,8-hexahydro-2H-benzo[b][1,4]thiazine-3-carboxylate (3) which is then reacted with malonyl chloride in the presence of DCM and dimethylformamide (DMF) to yield an intermediate compound which is then reacted with p-anisidine to yield the compound of Formula IA₁ (4).

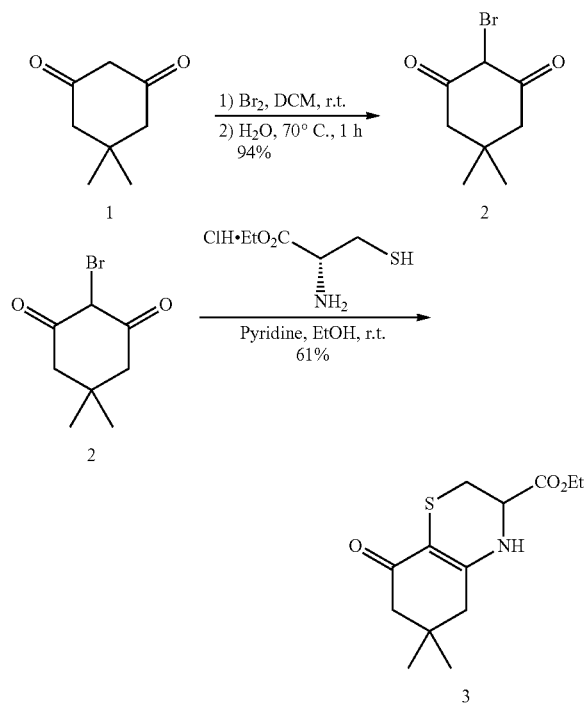

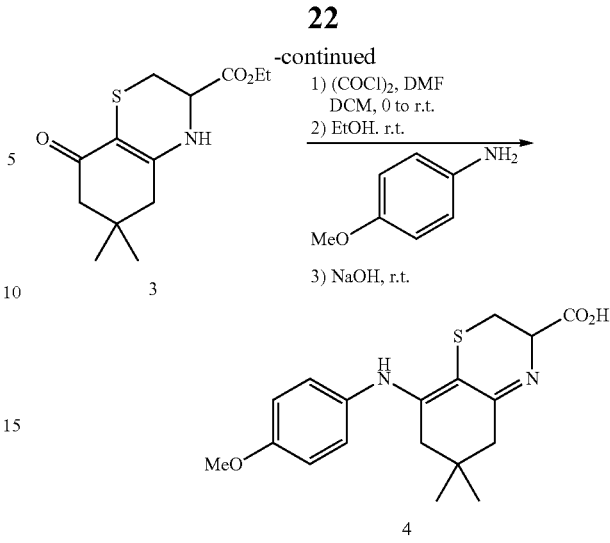

Once synthesized, the compounds of the invention can be isolated from chemical precursors or other chemicals using standard purification techniques such as, for example, chromatography (e.g., flash column chromatography and HPLC), asymmetric methods of synthesis, recrystallization and differential solubility. As used herein, the term "isolated" in the context of a compound such as, e.g., a compound of the invention, refers to a compound that is substantially free of chemical precursors, other chemicals when chemically synthesized or other isomers. In a specific embodiment, the compound is 60%, 65%, 70%, 75%, 80%, 85%, 90%, 91%, 92%, 93%, 94%, 95%, 96%, 97%, 98% or 99% free of other, different compounds (e.g., other isomers). Preferably, compounds of the invention are isolated.

Various compounds of the invention contain one or more chiral centers, and can exist as racemic mixtures of enantiomers, mixtures of diastereomers or enantiomerically or optically pure compounds. For example, mixtures comprising equal or unequal amounts of the enantiomers of a particular compound of the invention may be used in methods and compositions of the invention. It should also be noted the compounds of the invention include E and Z isomers, or a mixture thereof, and cis and trans isomers or a mixture thereof. In certain embodiments, the compounds of the invention are isolated as either the E or Z isomer. In other embodiments, the compounds of the invention are a mixture of the E and Z isomers.

As used herein and unless otherwise indicated, the term "stereomerically pure" means a composition that comprises one stereoisomer of a compound and is substantially free of other stereoisomers of that compound or one geometric isomer (e.g., about a double bond) that is substantially free of the other geometric isomer. For example, a stereomerically pure compound of the invention having one chiral center, or a composition thereof, will be substantially free of the opposite enantiomer of the compound. A stereomerically pure compound of the invention having two chiral centers, or a composition thereof, will be substantially free of other diastereomers of the compound. A stereomerically pure compound of the invention having a double bond capable of E/Z isomerism, or a composition thereof, will be substantially free of one of the E/Z isomers. A typical stereomerically pure compound comprises greater than about 80% by weight of one stereoisomer or E/Z isomer of the compound and less than about 20% by weight of other stereoisomers or E/Z isomer of the compound, more preferably greater than about 90% by weight of one stereoisomer or E/Z isomer of the compound and less than about 10% by weight of the other stereoisomers or E/Z isomer of the compound, even more preferably greater than about 95% by weight of one stereoisomer or E/Z isomer of the compound and less than about 5% by weight of the other stereoisomers or E/Z isomer of the compound, and most preferably greater than about 97% by weight of one stereoisomer or E/Z isomer of the compound and less than about 3% by weight of the other stereoisomers or E/Z isomer of the compound. As used herein and unless otherwise indicated, the term "stereomerically enriched" means a compound of the invention, or a composition thereof, that comprises greater than about 60% by weight of one stereoisomer or E/Z isomer of a compound of the invention, preferably greater than about 70% by weight, more preferably greater than about 80% by weight of one stereoisomer or E/Z isomer of a compound of the invention. As used herein and unless otherwise indicated, the term "enantiomerically pure" means a stereomerically pure compound of the invention having one chiral center, or a composition thereof. Similarly, the term "stereomerically enriched" means a stereomerically enriched compound of the invention having one chiral center, or a composition thereof.

It should be noted that if the stereochemistry of a structure or a portion of a structure is not indicated with, for example, bold or dashed lines, the structure or portion of the structure is to be interpreted as encompassing all stereoisomers of it.

In other embodiments, the present invention provides methods and techniques for determining the UV-absorbing capacity of the compounds as defined herein. The UV-absorbing properties of the compounds defined herein can be determined by spectrophotometer according to techniques and methods well known in the art. For example, ultraviolet-visible spectroscopy or ultraviolet-visible spectrophotometry (UV-Vis or UV/Vis) may be used to calculate the wavelength of maximal absorption ($\lambda_{max}$) of the compound.

A person skilled in the art will appreciate that the spectral characteristics of the compounds of the invention including the value of their extinction coefficient (c) and the value of their $\lambda_{max}$ are influenced by the structural elements of the compounds, for example, by the nature of the functional groups/substituents present on the compounds. The more efficient is the electron delocalization in a compound of the invention, the higher its extinction coefficient should be.

The photosensitivity of the compounds defined herein may be indicative of the compound's efficacy in absorbing UV radiations. The photosensitivity of a compound may be determined using an SPF analyser (such as for example, but not limited to, Optometrix, SPF 290). Mathematically, the SPF is calculated from measured data as:

$$SPF = \frac{\int A(\lambda) E(\lambda) d\lambda}{\int A(\lambda) E(\lambda) / MPF(\lambda) d\lambda}$$

Where $E(\lambda)$ is the solar irradiance spectrum, $A(\lambda)$ the erythemal action spectrum and $MPF(\lambda)$ the monochromatic protection factor, all functions of the wavelength. The MPF is roughly the inverse of the transmittance at a given wavelength. In order to calculate the SPF value for a compound of the invention, the compound may be dissolved in a suitable solvent (such as, for example, in methanol or ethanol) at an appropriate concentration (such as, for example, from between about $1.10^{-5}$ to about $5.10^{-5}$ M), placed in a quartz cell and irradiated using a metal halide lamp ($I_{UVB}$=0.4 to 8.0 mW/cm). For conversion to the solar spectrum (CIE D65 standard daylight, standardized to $I_{UVB}$=0.127 mW/cm$^2$), the integral over the products of the wavelength-resolved lamp intensity and the corresponding absorption values of the compound between 290 and 400 nm is calculated and divided by the integral over the products of the D65 light intensities and the corresponding absorption values of the compound in the range between 290 and 400 nm. That factor is multiplied by the half-life value for degradation under irradiation with the metal halide lamp in order to obtain the corresponding half-life value under solar irradiation. The half-life value for photo-degradation under lamp irradiation is determined by UV spectroscopic measurement of the extinction at the wavelength of maximum absorbance and subsequent exponential fit. The half-life values for photo-degradation in D65 light are obtained using this method.

Determination or measurement of other physical properties of the compounds defined herein may be used in assessing a compound's efficacy in absorbing UV radiations, such as, but not limited to, melting point determination, optical activity, IR spectroscopy, MS spectroscopy, NMR spectroscopy, and measurement of water resistance. These and other techniques as well as the way of carrying them out are well known in the art.

C) Formulations and Compositions

The compounds of the invention may be used to absorb UV radiations. The compounds of the invention may also provide protection to biological and non-biological materials against damaging effects of UV radiations, in particular against the damaging effects of UVA or UVB or both radiations. These formulations and compositions comprise the compounds of general Formula I as defined herein.

The compounds of the invention may be formulated in combination with other compounds in order to obtain formulations and/or compositions with the desired characteristics. Such other compounds may include a wide range of ingredients and compounds that are not UV absorbers/filters/blockers per se but that help to control characteristics of the composition itself such as film thickness, opacity, rub resistance, water proofing and uniformity. Alternatively, such other compounds may also include a wide range of ingredients that act as UV absorbers/filters/blockers, such as compounds that are UVA absorbers/filters/blockers and compounds that are UVB absorbers/filters/blockers.

According to one embodiment, the compounds of the invention may be incorporated into formulations and/or compositions in an amount of from about 1% to about 99% of the weight of the formulations and/or the compositions. The other compounds may be incorporated into formulations and/or compositions in an amount of from about 99% to about 1% of the weight of the formulations and/or the compositions. In a preferred implementation, the compounds of the invention are incorporated in the formulations and/or compositions in an amount that varies between about 0.2% and about 30% of the weight of formulation and/or the compositions. Suitable masses and concentrations for the compounds defined herein as well as masses and concentrations for the other components incorporated into the formulations and/or compositions depend on the nature of the formulations and/or compositions and on the biological and/or non-biological materials for which they are intended to be used. Such elements will be appreciated by those skilled in the art using techniques known in the art.

One potentially useful application of the compounds defined herein is their incorporation into compositions and/or formulation for protecting biological materials from UV radiations. Such compositions and/or formulations may be sunscreen compositions and may be formulated according to techniques well known in the art, in particular techniques for preparation of oil-in-water or water-in-oil emulsions. In addition, the compounds of the invention may be formulated into carriers such as, water, water-based liquids, lotions, dispersions, oils, oil-based solutions, powder, gels, emulsions, dispersions or mixtures thereof. The appropriate amount of carrier can readily be determined by those skilled in the art according to, for example, a desired sun protection factor (SPF) to achieve. The specific amount of compounds defined herein needed to obtain a desired sun protection factor (SPF) can be determined by techniques well known in the art. Sunscreen should provide a minimum protection against UVA and/or UVB rays. An increased sun protection factor (i.e., mainly UVB protection) should include an increase in the UVA protection as well. In some implementations, the protection against UVA and UVB radiation should be related.

The UV absorbance of a sunscreen product can be determined in vitro over the entire UV spectrum (290 nm-400 nm) using substrate spectrophotometry. For example, a uniform amount and thickness of sunscreen is applied to a slide and exposed to UV light; the absorbance of that UV radiation is measured according to techniques well known in the art. The UV absorbance curve obtained demonstrates the amplitude and breadth of protection provided (from 290 nm-400 nm) across the UV spectrum. The "amplitude" of the absorbance curve reflects the degree of protection. The higher the amplitude of the curve, the greater the absorbance and the more protection provided at that wavelength. Within the UVB portion of the spectrum (290 nm-320 nm) this amplitude correlates with the SPF. The greater the "breadth" of the curve, the more protection provided against longer wave UV radiation. In other words, the greater the "breadth" of the curve, the broader the spectrum of sun protection provided. Mathematical integration of the measured spectral absorbance from 290 nm to 400 nm is performed to calculate the area beneath the curve. The "Critical Wavelength" ($\lambda c$) is the wavelength below which 90% of the area under the absorbance curve resides. A SPF value of 2 generally absorbs 50% UVB, a SPF value of 15 generally absorbs 93.3% UVB, SPF 30 absorbs 96.7% UVB and SPF 50 absorbs 98% UVB.

In the preparation of a sunscreen composition, the compounds defined herein may be used in combination with other UV-absorbing agents known in the art, such as, but not limited to, UV-blocking agents hydrophilic or lipophilic organic UV-A and/or UV-B sunscreen agents. Examples of other UV-absorbing agents which may be included in the formulations and/or compositions of the present invention include, but are not limited to: aminobenzoic acid; padimate O; phenylbenzimidazole sulfonic acid; cinoxate, dioxybenzone; oxybenzone; homosalate; menthyl anthranilate, octocrylene; octyl methoxycinnamate; octyl salicylate; sulisobenzone; trolamine salicylate; avobenzone; ecamsule; titanium dioxide; 4-methylbenzylidene camphor; tinosorb M; tinosorb S; neo heliopan AP; mexoryl XL; benzophenone-9; uvinul T 150; uvinul A Plus; uasorb HEB; parsol SLX and isopentenyl-4-methoxycinnamate; 4-dimethylaminobenzoic acid 2-ethylhexyl ester; salicylic acid derivatives, for example salicylic acid 2-ethylhexyl ester; benzophenone derivatives, for example 2-hydroxy-4-methoxybenzophenone and its 5-sulfonic acid derivative; dibenzoylmethane derivatives, for example 1-(4-tert-butylphenyl)-3-(4-methoxyphenyl)-propane-1,3-dione; diphenylacrylates, for example 2-ethylhexyl-2-cyano-3,3-diphenylacrylate, and 3-(benzofuranyl)-2-cyanoacrylate; 3-imidazol-4-ylacrylic acid and esters; benzofuran derivatives, such as 2-(p-aminophenyl)benzofuran derivatives; polymeric UV absorbers, such as benzylidene malonate derivatives; cinnamic acid derivatives, for example the 4-methoxycinnamic acid 2-ethylhexyl ester and isoamyl ester or cinnamic acid derivatives; camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2,2,1]heptane-1-methane-sulfonic acid) and salts, 3-(4'-sulfo)benzylidene-bornan-2-one and salts; camphorbenzalkonium methosulfate; hydroxyphenyl-triazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2"-methylpropenyloxy)-2-hydroxy]-phenyl}-6-(4-methoxyphenyl)-1,3,5-triazine; 2,4-bis{[4-(1',1',1',3',5',5', 5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol; trianilino-s-triazine derivatives, for example 2,4,6-trianiline-(p-carbo-2'-ethyl-1'-oxy)-1,3,5-triazine;
2-phenylbenzimidazole-5-sulfonic acid and salts thereof; menthyl-o-aminobenzoates; physical sunscreens coated or not coated, such as titanium dioxide, zinc oxide, iron oxides, mica, MnO, $Fe_2O_3$, $Ce_2O_3$, $Al_2O_3$, $ZrO_2$ (surface coatings: polymethylmethacrylate, methicone (methylhydrogenpolysiloxane), dimethicone, isopropyl titanium triisostearate, metal soaps such as magnesium stearate, perfluoroalcohol phosphate as $C_{9-15}$ fluoroalcohol phosphate).

Examples of UVA-absorbing agents include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX) and methyl anthranilate.

Examples of UVB-blocking agents include, but are note limited to, 4-Aminobenzoic acid (PABA), cinoxate, ethylhexyl triazone (Uvinul T 150), homosalate, 4-Methylbenzylidene camphor (Parsol 5000), octyl methoxycinnamate (octinoxate), octyl salicylate (Octisalate), padimate O (Escalol 507), phenylbenzimidazole sulfonic acid (Ensulizole), polysilicone-15 (Parsol SLX) and trolamine salicylate.

Examples of agents that block both UVA and UVB include, but are not limited to, bemotrizinol (Tinosorb S), Bbenzophenones 1-12, ioxybenzone, drometrizole trisiloxane (Mexoryl XL), iscotrizinol (Uvasorb HEB), octocrylene, oxybenzone (Eusolex 4360), sulisobenzone, hybrid (chemical/physical): bisoctrizole (Tinosorb M), titanium dioxide and zinc oxide.

In addition, the sunscreen compositions may also include adjuvants and additives such as preservatives, organic solvents, browning agents, antioxidants, stabilizers, emollients, silicones, alpha-hydroxy acids, demulcents, anti-foaming agents, moisturizing agents, vitamins, fragrances, ionic or nonionic thickeners, surfactants, fillers, thickeners, sequestrants, polymers, propellants, alkalinizing or acidifying agents, opacifiers, fatty compounds (e.g., oil, wax, alcohols, esters, fatty acids), colorants, or mixtures thereof or any other ingredient that may be used for the production of sunscreen compositions.

The sunscreen compositions of the present invention may be in the form of an aqueous solution, emulsions (oil in water or water in oil), a hydro alcoholic vehicle, a stick, an ointment, a gel, an aerosol (foams, sprays propellant pumps or the like).

In another embodiment of the present invention, the compounds defined herein may be formulated in cosmetics and/or personal care products. The compounds may be incorporated into cosmetic and/or personal care products formulations or compositions in an amount of from about 0.2% to about 30% of the weight of the formulation or the composition, more preferably from about 1% to about 15% of the weight of the formulation or the composition.

The compounds of the present invention may be included into formulations used in the preparation of cosmetic products such as make-ups, for example in cream make-up, eye-care preparations, eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers. These products are formulated according to known methods in the art.

The compounds of the present invention may also be formulated into personal care products such as in skin-washing and cleansing preparations in the form of tablet-form or liquid soaps, detergents or washing pastes, bath preparations, e.g. liquid (foam baths, milks, shower preparations) or solid bath preparations, e.g. bath cubes and bath salts; skin-care preparations, e.g. skin emulsions, multi-emulsions or skin oils; cosmetic personal care preparations, e.g. facial make-up in the form of day creams or powder creams, face powder (loose or pressed), foot-care preparations, e.g. foot baths, foot powders, foot creams or foot balsams, special deodorants and antiperspirants or callus-removing preparations; light-protective preparations, such as sun milks, lotions, creams or oils, pre-tanning preparations or after-sun preparations; skin-tanning preparations, e.g. self-tanning creams; depigmenting preparations, e.g. preparations for bleaching the skin or skin-lightening preparations; insect-repellents, e.g. insect-repellent oils, lotions, sprays or sticks; deodorants, such as deodorant sprays, pump-action sprays, deodorant gels, sticks or roll-ons; antiperspirants, e.g. antiperspirant sticks, creams or roll-ons; preparations for cleansing and caring for blemished skin, e.g. synthetic detergents (solid or liquid), peeling or scrub preparations or peeling masks; hair-removal preparations in chemical form (depilation), e.g. hair-removing powders, liquid hair-removing preparations, cream- or paste-form hair-removing preparations, hair-removing preparations in gel form or aerosol foams; shaving preparations, e.g. shaving soap, foaming shaving creams, non-foaming shaving creams, foams and gels, preshave preparations for dry shaving, aftershaves or aftershave lotions; fragrance preparations, e.g. fragrances, perfume oils or perfume creams; cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile. These products are formulated according to known methods in the art.

The compounds as defined herein may also be incorporated into formulation that may be used to protect hair (from humans or animals) against photochemical damage in order to prevent changes of color shades, discoloration or damage of a mechanical nature.

In addition to the compounds defined herein, the cosmetic formulation may comprise various adjuvants used in this type of composition, such as surface-active agents, thickeners, polymers, softeners, preservatives, foam stabilizers, electrolytes, organic solvents, silicone derivatives, antigrease agents, dyes and/or pigments which color the composition itself or the hair, or other ingredients customarily used for hair care.

The compounds of the present invention may also be included into pharmaceutical formulations and/or compositions. These formulations and/or compositions are prepared according to known methods in the art.

Ointments, pastes, creams and gels comprising the compounds of the invention may include one or more carriers, such as, but not limited to, animal and vegetable fats, waxes, paraffins, starch, tragacanth, cellulose derivatives, polyethylene glycols, silicones, bentonites, silica, talc and zinc oxide or mixtures of these substances. Powders and sprays may include carriers, such as, but mot limited to, lactose, talc, silica, aluminum hydroxide, calcium silicate and polyamide powder or mixtures of these substances, propellants, such as, but not limited to chlorofluorocarbons, propane/butane or dimethyl ether. Solutions and emulsions can include carriers, such as, but not limited to, solvents, solubility promoters and emulsifiers, e.g. water, ethanol, isopropanol, ethyl carbonate, ethyl acetate, benzyl alcohol, benzyl benzoate, propylene glycol, 1,3-butylglycol, oils, in particular cotton seed oil, peanut oil, wheatgerm oil, olive oil, castor oil and sesame oil, glycerol fatty acid ester, polyethylene glycols and fatty acid esters of sorbitan or mixtures of these substances. Soaps can include carriers, such as, but not limited to, alkali metal salts of fatty acids, salts of fatty acid mono esters, fatty acid protein hydrolysates, isethionates, lanolin, fatty alcohol, vegetable oils, plant extracts, glycerol, sugars or mixtures of these substances. Face and body oils can include carrier substances such as, but not limited to, synthetic oils, such as fatty acid esters, fatty alcohols, silicone oils, natural oils, such as vegetable oils and oily plant extracts, paraffin oils, lanolin oils or mixtures of these substances.

The compounds of the invention may also be formulated for topical administration. The term "topical" as used herein includes any route of administration that enables the compounds to line the skin or mucosal tissues.

The formulations and the compositions of the present invention also offer protection against ageing processes of the skin and against oxidative stress, against damage caused by free radicals, as are produced, for example, by solar irradiation, heat or other influences.

The compounds of the invention as well as the formulations and the compositions of the invention may be used in the preparation and manufacture of medicaments for the prevention of damages to skin, such as, but not limited to, sunburn and sun-caused erythrema.

The cosmetic or pharmaceutical formulations and/or compositions according to the invention may also comprise one or one more additional compounds such as but not limited to: alcohols, poly-alcohols, fatty alcohols, esters of fatty acids, natural or synthetic triglycerides including glyceryl esters and derivatives, pearlescent waxes, hydrocarbon oils, siliconces or siloxanes, fluorinated or perfluorinated oils, emulsifiers, surfactants, polymers, deodorizing active ingredients, antioxidants, hydrotropic agents, preservatives and bacteria-inhibiting agents, perfumes, colorants, preservatives, bactericides and bacteriostatic agents, perfumes, dyes, pigments, thickening agents, moisturizing agents, humectants, fats, oils, waxes, polymers, electrolytes, organic solvents, silicon derivatives, emollients, emulsifiers or emulsifying surfactants, surfactants, dispersing agents, antioxidants, anti-irritants and anti-inflammatory agents.

Examples of emulsifiers that may be included in the formulations and/or compositions of the present invention include, but are not limited to, cocoyl glucoside, cocoyl glucoside/cetearyl alcohol, cocoyl ethyl glucoside, disodium coco-glucoside citrate, lauryl glucoside, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, butylated PVP, cetyl alcohol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate, butylated PVP, cetyl alcohol, sodium acrylate/sodium acryloyldimethyltaurate copolymer, diethylhexyl napthalate, sodium stearoyl glutamate such as EUMULGIN®SG, sodium N-stearoyl L-glutamate, dioctyldodecyl stearoyl glutamate, TEA-cocoyl glutamate, TEA-lauryl glutamate, TEA-stearoyl glutamate, aluminum stearoyl glutamate, monosodium glutamate, disodium glutamate and any mixtures thereof.

In other embodiments, the present invention provides for methods of preventing and/or treating biological materials from harmful solar effects. In particular, the invention provides a method for preventing harmful solar effects on a subject such as a human. Examples of harmful solar effects include but are not limited to, sunburn, inflammation, melanoma, malignant melanoma, DNA damage, eye damages, erythema and local or systemic immuno-suppression.

In one implementation of this embodiment, the method is for preventing the harmful effects of UV radiations on a subject such as a human; include the steps of applying a formulation and/or a composition comprising one or more of the compounds of the invention onto the skin of the human subject. The method may also be used to protect skin of animal subjects.

The term "treatment" of a subject, as used herein, unless otherwise indicated, refers to both therapeutic treatments as well as to prophylactic and preventative measures. Those in need of treatment include those already with the disease or disorder or condition as well as those in which the disease, disorder or condition is to be prevented. The subjects in need of treatment are also those in which the disorder, disease or condition has occurred and left after-effects or scars. Treatment also refers to administering a therapeutic substance effective to improve or ameliorate symptoms associated with a disease, a disorder or a condition to lessen the severity of or cure the disease, disorder or condition, or to prevent the disease, disorder or condition from occurring.

In another embodiment of the present invention, non-biological materials, such as, but not limited to, articles of manufacture, may be impregnated with or may be covered with a formulations and/or compositions comprising the compounds defined herein. Examples of such non-biological materials include, but are not limited to, windows and other glass, plexi-glass, transparent polymer, plastic or similar products, car windshields, solar panels, eye glasses, sporting goods, textiles and fabrics. The techniques and method for impregnating and/or coating the formulations and/or compositions of the invention on articles of manufacture are known in the art.

In another embodiment of the present invention, the compounds defined herein, may be incorporated into compositions that are suitable for application on the surface of non-biological materials, such as articles of manufacture. Such compositions include, but are not limited to: coatings, paints, sealants, adhesives, dyes, compositions for application onto fabrics, compositions for application onto textiles or fibers, varnishes, stains, coloring compositions, flame retardant coating compositions, adhesives, lacquers and similar coatings. Such compositions comprising the compounds of the invention prevent premature photodamage and photobleaching to surface of these articles of manufacture. Such compositions of this invention may be prepared by mixing (or mechanically agitating) the compounds defined herein and any additional optional components, to form a homogenous mixture. This may be accomplished by any convenient mixing method known in the art exemplified by a spatula, mechanical stirrers, in-line mixing systems containing baffles and/or blades, powered in-line mixers, homogenizers, a drum roller, a three-roll mill, a sigma blade mixer, a bread dough mixer, and a two roll mill.

In some implementations of this embodiment, the compounds of the invention may be applied to textiles or fabrics in order to protect these textiles or fabrics from exposure to UV radiations causing ageing of the textiles or fabrics and/or weakening of its structure and strength. Compositions comprising the compounds of the invention may be applied onto the textiles or the fabrics. Alternatively or in complement, the textiles or fabrics may be immersed partly or totally into a solution comprising the compounds of the invention as well as other components such as discussed herein. The textiles or fabrics that have been applied with the compounds of the invention are herein referred to as "treated textiles" and "treated fabrics". Resistance of the treated textiles or treated fabrics to exposure to UV radiations may be assessed by determining such properties of the treated textiles and treated fabrics as, but not limited to, color fastness and/or breaking strength by the strip method following UV exposure. The techniques for determining these properties of a treated textile or a treated fabric are well known in the art.

The invention also includes a method of reducing degradation of chemicals that are sensitive to UV light comprising applying a formulation and/or a composition of the invention to the chemical. The chemical is a herbicide, a pesticide, an auxin, a gibberellin, abscisic acid, a cytokinin, derivative of a carotenoid, a polyphenolic compound, a mycosporine amino acid and or a derivative of any of the foregoing (mixtures or pure preparations).

In another embodiment, the compounds of the present invention may be incorporated into a substrate which constitutes the base formulation for the manufacture of a non-biological material. For example, the compounds of the present invention may be incorporated into a substrate which constitutes the base formulation of liquid coatings or powder coatings, or the base resin of an article to be fabricated using conventional plastic compounding, molding or extrusion processes. The substrates into which the compounds of the present invention may be incorporated include a wide variety of resin and plastic materials, for example, polyolefins, polyvinylaromatics, acrylics, polycarbonates, polyesters, polyamides, polyimides, polyarylates, polysulfones, polybutenes, polypropenes, epoxies, and polyvinylhalide resins and generally any resin known to be susceptible to degradation being exposed to ultraviolet light radiation. Naturally, the choice of compound of the present invention to be incorporated into such substrate must be made such that, at the temperatures for processing the paints, coatings, finishes or thermoplastic articles, the compounds of the present invention do not undergo substantial degradation or cross reaction with any other ingredients of the formulation. Representative, but non-limiting, examples of specific polymeric resin materials include polyolefin resins such as polyethylene and polypropylene and the like; polyvinylaromatic resins such as polystyrene and copolymers and terpolymers therefor, such as poly(styrene-acrylonitrite) and poly(styrene-butadieneacrylonitrile) and the like; acrylic resins such as poly(acrylic acid), poly(methacrylic acid), poly(methyl acrylate), poly(methyl methacrylate) and the like; polycarbonate resins such as those obtained either by the phosgenation of dihydroxy aliphatic and aromatic monomers such as ethylene glycol, propylene glycol, bisphenol A (i.e., 4,4'-isopropylidene diphenol) and the like, or by the base catalyzed transesterification of bisphenol A with diphenylcarbonate to produce bisphenol A polycarbonate; polyester resins such as poly(ethylene terephthalate), poly(butylene terephthalate) and the like; polyamide resins such as nylon-6, nylon-6,6 and the like; epoxy resins such as poly(epichlorohydrin/bisphenol A) and the like, and esters thereof such as the epoxy resin esters prepared by the esterification of poly(epichlorohydrin/bisphenol A) with a fatty acid, rosin acid, tall oil acid or mixtures thereof; and phenolic resins such as those prepared by reaction of formaldehyde with phenol, resorcinol, cresol, xylenol, p-tert-butylphenol and the like.

In other embodiments, the present invention provides methods and techniques for assaying the formulations and/or compositions of the invention for protection against solar radiations. Such methods and techniques include, but are not limited to, measurement of the $\lambda_{max}$, measurement of the SPF, assessment of the compound stability, measurement of water resistance, and measurement of photo-sensitivity of the formulation and/or composition.

D) Examples

The embodiments of the present invention are now illustrated by, but in no way limited to, the following examples.

Example 1

Synthetic scheme for preparation of 2-Bromo-5,5-dimethyl-1,3-cyclohexandione Intermediate

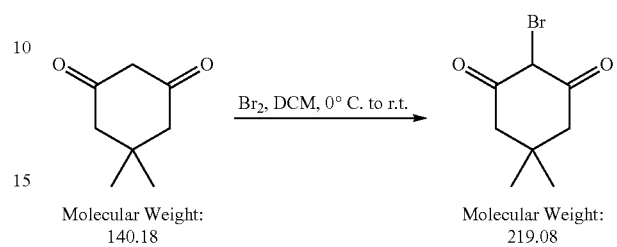

Molecular Weight: 140.18

Molecular Weight: 219.08

In a 250 mL round bottom flask was added a solution of bromine (28.5 g, 178.3 mmol) in dichloromethane (DCM) (20 mL) over 30 min to a suspension of dimedone (25 g, 178.3 mmol) in DCM (200 mL) at 0° C. The suspension became a solution after 5 min and a suspension after 10 min., it was then stirred at RT for 18 h. The suspension was then filtered, washed with DCM (50 mL) and Hex (2×150 mL), then dried under vacuum for 2 h. The solid was suspended in water (500 ml) and heated at 80° C. for 1 h, cooled to RT, filtered, washed with water (2×100 mL) then dried under vacuum for 2 h and on vacuum oven at 60° C. for 20 h.

Example 2

Synthetic Scheme for Preparation of (R)-6,6-dimethyl-8-oxo-3,4,5,6,7,8-hexahydro-2H-benzo[b][1,4]thiazine-3-carboxylic acid Intermediate

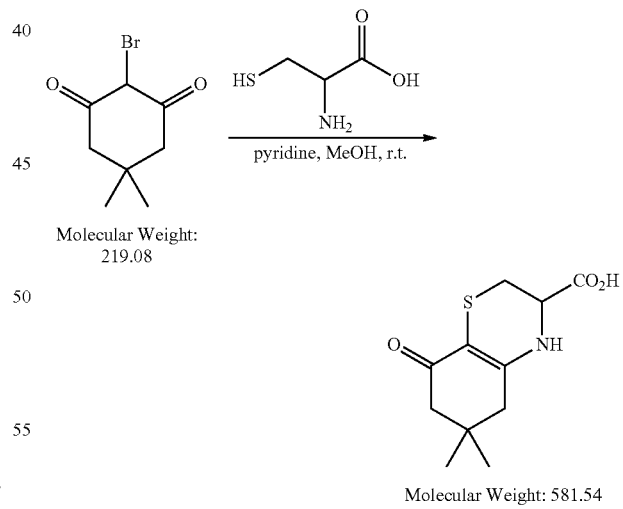

Molecular Weight: 219.08

Molecular Weight: 581.54

In a 100 mL round bottom flask was added L-cysteine (1.21 g, 10.04 mmol) to a solution of 2-bromo-5,5-dimethyl-cyclohexane-1,3-dione (2 g, 9.13 mmol) and pyridine (1.47 mL, 18.25 mmol) in MeOH (30 mL). The suspension was stirred at RT for 18 h then concentrated. MeOH (20 mL) was added to obtain slush, then filtered and washed with MeOH (2×5 mL). The filtrate which contained the product was concentrated. The concentrated filtrate was azotroped with EA (2×25 mL). EA (20 mL) was added and triturated for 30 min, then filtered, washed with EA (2×15 mL) and dried under vacuum for 1 h.

Example 3

Synthetic scheme for the preparation of 2-bromocyclohexane-1,3-dione Intermediate

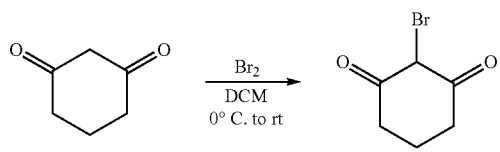

To a suspension of cyclohexane-1,3-dione (25 g, 0.216 mol) in DCM (70 ml) at 0° C. (ice bath) and under air atmosphere was slowly added a solution of bromine (34.6 g, 0.216 mol) in DCM (20 ml) over a period of 30 min. The temperature was allowed to increase to RT and 50 ml of DCM were added to create a reaction mixture that is pasty. The reaction mixture was stirred at RT for 4 hrs and the solid was collected by filtration, rinsed successively with DCM (50 ml) and hexanes (3×200 ml), and air dried. The solid was suspended in water (500 ml) and the suspension was stirred and heated at 80° C. for 1 h, then RT overnight. The solid was collected by filtration, rinsed with water (1000 ml), air dried and dried under high vacuum at 55° C. for one day to afford the desired compound (30.53 g, 0.160 mol, 74% yield). Characterization: $^1$H RMN (400 MHz, CDCl$_3$): δ (ppm)=2.62 (t, J=6.5 Hz, 4H), 2.62 (quint, J=6.5 Hz, 2H). MS (m/z): 190.9-192.9 [M+H]$^+$.

Example 4

Synthetic Scheme for the Preparation of Methyl 2-((3-oxocyclohex-1-en-1-yl)amino)acetate Intermediate

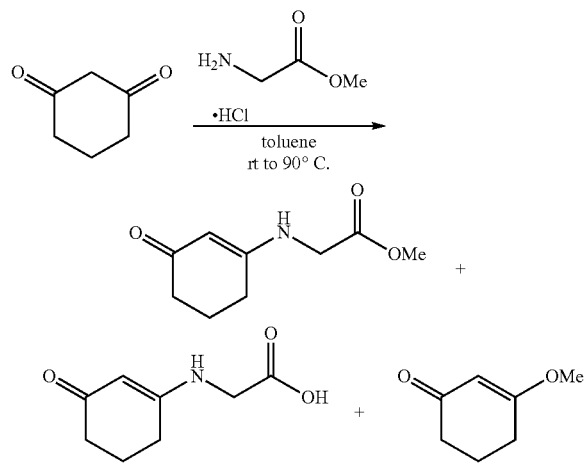

A stirred suspension of cyclohexane-1,3-dione (5 g, 43.25 mmol) and methyl glycine ester hydrochloride (7.42 g, 58.51 mmol) in toluene (100 ml) under nitrogen atmosphere was heated at 90° C. for 5 h, then RT. The liquid phase (mainly 3-methoxycyclohex-2-enone by MS) was removed by decantation, the sticky residue (mainly methyl 2-(3-oxocyclohex-1-enylamino)-acetate by MS) was dissolved in water and the pH was adjusted to 7-8 by addition of a saturated aqueous solution of sodium bicarbonate and extracted with DCM (×7). The combined organic layer (DCM) was dried over anhydrous magnesium sulfate, filtered and concentrated. The crude residue was purified by Biotage (Snap 100 g cartridge, eluted with MeOH/DCM: 1/99 to 10/90 over 30 CV, wavelength collection at 254 nm). The desired fractions were combined, concentrated and dried under high vacuum to afford the desired product. Characterization: $^1$H RMN (400 MHz, DMSO-d$_6$): δ (ppm)= 7.36-7.20 (m, 1H), 4.67 (s, 1H), 3.87 (d, J=5.9 Hz, 2H), 3.66 (s, 3H), 2.35 (t, J=6.2 Hz, 2H), 2.07 (t, J=6.5 Hz, 2H), 1.79 (quint, J=6.2 Hz, 2H), MS (m/z): 183.96 [M+H]$^+$.

Example 5

Synthetic Scheme for the Preparation of (R)-8-oxo-3,4,5,6,7,8-hexahydro-2H-benzo[b][1,4]thiazine-3-carboxylic acid Intermediate

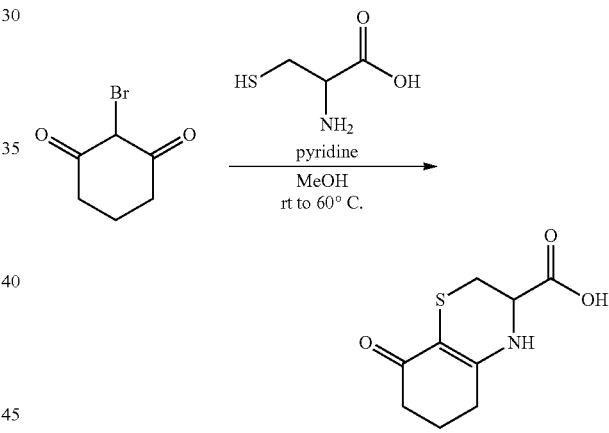

Pyridine was slowly added (847 l, 10.47 mmol) to a stirred suspension of 2-bromocyclohexane-1,3-dione (1 g, 5.24 mmol) and L-cysteine (698 mg, 5.76 mmol) in anhydrous MeOH (20 ml) at RT and under nitrogen atmosphere. The reaction mixture was heated at 60° C. for 1 h (complete conversion by MS), then stirred at RT overnight, concentrated, diluted with water, and shaken and sonicated for a while. The solid (A) was collected by filtration, rinsed with water, air dried and dried under high vacuum. The solid (A) (177 mg) was soluble in TFA. The mother liquid was concentrated, and triturated and sonicated in a minimum of MeOH. The solid (B) was collected by filtration, rinsed with MeOH, air dried and dried under high vacuum to afford the desired compound (580 mg, 2.71 mmol, 51% yield) as an ivory solid. Characterization: $^1$H RMN (400 MHz, DMSO-d$_6$): (ppm)=13.15-12.80 (m, 1H), 7.57 (d, J=4.3 Hz, 1H), 4.38 (q, J=4.0 Hz, 1H), 2.99 (dd, J=12.9, 4.3 Hz, 1H), 2.80 (dd, J=12.9, 3.3 Hz, 1H), 2.45 (t, J=6.2 Hz, 2H), 2.25-2.17 (m, 2H), 1.87-1.76 (m, 2H). MS (m/z): 213.9 [M+H]⁺.

Example 6

Synthetic Scheme for the Preparation of methyl 8-oxo-3,4,5,6,7,8-hexahydro-2H-benzo[b][1,4]oxazine-3-carboxylate Intermediate

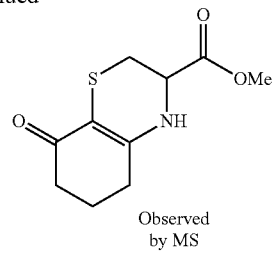

To a stirred suspension of sodium hydride (1.466 g, 36.645 mmol, in mineral oil) in anhydrous THF (30 ml) at 0° C. and under nitrogen atmosphere was added portionwise serine methyl ester hydrochloride (1.792 g, 11.52 mmol) over 10 min. After 10 min, a suspension of 2-bromocyclohexane-1,3-dione (2 g, 10.47 mmol) in anhydrous THF (20 ml) was added. The temperature was allowed to warm-up to RT over 3 hrs, then anhydrous DMF (10 ml) was added 2 hrs afterwards. The reaction mixture was stirred at RT overnight, quenched by addition of water, 1N HCl (pH~1), and partitioned with AcOEt. After separation, the organic layer was successively washed with water (×3) and brine, dried over anhydrous magnesium sulfate, filtered, and concentrated to afford the unreacted starting material contaminated with the mineral oil. Characterization: ¹H RMN (400 MHz, DMSO-d₆): δ(ppm)=MS (m/z): [M+H]⁺

Example 7

Synthetic Scheme for the Preparation of (R)-methyl 8-oxo-3,4,5,6,7,8-hexahydro-2H-benzo[b][1,4]thiazine-3-carboxylate and (3R)-methyl 8-oxo-3,4,5,6,7,8-hexahydro-2H-benzo[b][1,4]thiazine-3-carboxylate 1-oxide and 2-bromo-3-methoxycyclohex-2-enone Intermediates

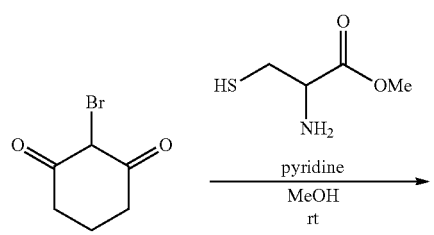

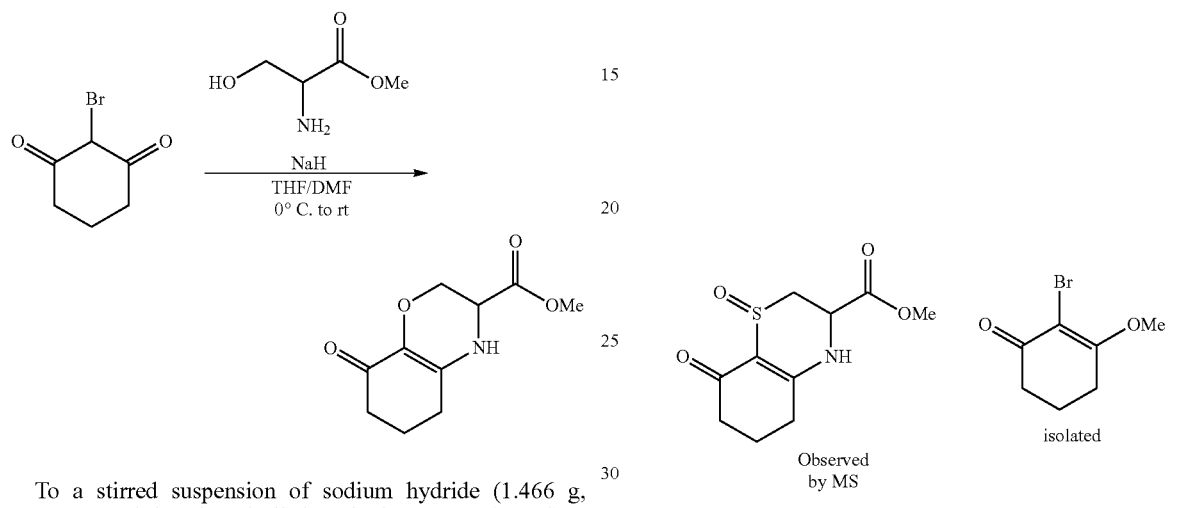

A solution of 2-bromocyclohexane-1,3-dione (3 g, 15.71 mmol) and L-cysteine (3.07 g, 17.89 mmol) in anhydrous MeOH (50 ml) was stirred at RT for 1 h (complete transformation into 2-bromo-3-methoxycyclohex-2-enone by MS), then was slowly added pyridine (2.54 ml, 31.41 mmol). The reaction mixture was stirred at RT overnight (reaction not complete by MS, formation of the desired MW+oxidation). 500 mg of L-cysteine methyl ester hydrochloride were added and the reaction mixture was stirred at RT overnight (more oxidation by MS). The reaction mixture was concentrated, diluted with water and shaken and sonicated for a while. The solid A was collected by filtration, rinsed with water, air dried (mainly pyridine and 2-bromo-3-methoxycyclohex-2-enone by MS). The mother liquid was basified with a saturated aqueous solution of sodium bicarbonate (pH~9), and extracted with AcOEt. The organic layer was successively washed with NaHCO₃ sat, NH₄Cl sat, water and brine, dried over anhydrous magnesium sulfate, filtered, and concentrated. The crude residue was purified by Biotage (SiliaFlash 80 g cartridge, eluted with MeOH/DCM: 0/100 to 05/95 over 30 CV). The desired fractions were combined, concentrated and dried under high vacuum to afford 2-bromo-3-methoxycyclohex-2-enone (682 mg, 3.33 mmol, 21% yield). Characterization: ¹H RMN (400 MHz, DMSO-d₆): δ (ppm)=3.93 (s, 3H), 2.80 (t, J=6.2 Hz, 2H), 2.44-2.37 (m, 2H), 1.96-1.87 (m, 2H). MS (m/z): 204.8-206.8 [M+H]⁺.

Example 8

Synthetic Scheme for the Preparation of 3-((4-methoxyphenyl)amino)-5,5-dimethylcyclohex-2-enone and (E)-4-methoxy-N-(3-((4-methoxyphenyl)amino)-5,5-dimethylcyclohex-2-en-1-ylidene)aniline Intermediates

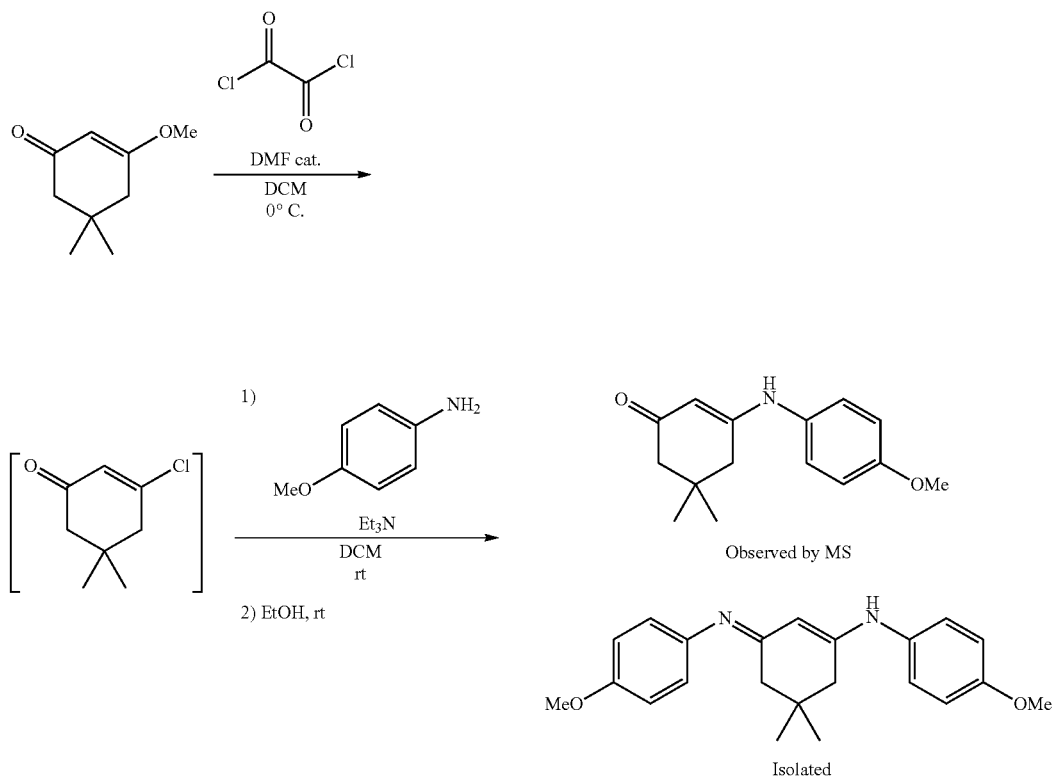

To a stirred solution of 3-methoxy-5,5-dimethylcyclohex-2-enone (1 g, 4.73 mmol) in anhydrous DCM (30 ml) at 0° C. and under nitrogen atmosphere were slowly added oxalyl chloride (601 µl, 7.10 mmol) and anhydrous DMF (3 drops). After 50 min (conversion almost complete by TLC), more oxalyl chloride was added (50 µl). After 20 min, the reaction mixture was concentrated, dissolved in anhydrous DCM (30 min), cooled-down to 0° C., and 4-methoxyaniline (612 mg, 4.97 mmol) and trietylamine (1.98 ml, 14.20 mmol) were added, respectively. The reaction mixture was stirred at RT overnight, concentrated, diluted in ethanol (20 ml), and stirred again overnight. The solid was collected by filtration, rinsed with ethanol and air dried [3-(4-methoxyphenylamino)-5,5-dimethylcyclohex-2-enone was present in the mother liquid by MS]. The crude residue was purified by Biotage (Snap 25 g cartridge, eluted with MeOH/DCM: 5/95 to 20/80 over 30 CV). The desired fractions were combined, concentrated, triturated in a minimum of DCM, filtered, rinsed with DCM, air-dried and dried under high vacuum to afford (E)-N,N'-(5,5-dimethylcyclohex-1-ene-1-yl-3-ylidene)bis(4-methoxyaniline) (198 mg, 0.51 mmol, 7.9% yield, HCl salt). Characterization: $^1$H RMN (400 MHz, DMSO-$d_6$): δ (ppm)=11.40-10.65 (m, 2H), AB system ($δ_A$=7.19, $δ_B$=7.01, $J_{AB}$=8.2 Hz, 8H), 5.90-5.44 (m, 1H), 3.76 (s, 6H), 2.60 (bs, 4H), 1.08 (bs, 6H). MS (m/z): 351.15 [M+H]$^+$ HPLC: >97% UV: $λ_{max}$ ~345 nm (MeOH/water).

Example 9

Synthetic Scheme for the Preparation of methyl 2-((3-oxocyclohex-1-en-1-yl)amino)acetate Intermediates

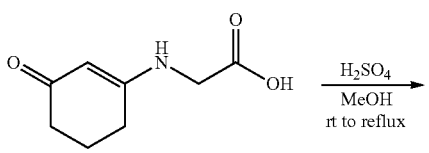

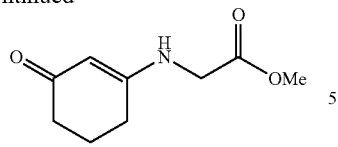

To a stirred suspension of 2-((3-oxocyclohex-1-en-1-yl)amino)acetic acid (1.51 g, 8.93 mmol) in MeOH (30 ml) under nitrogen atmosphere was added concentrated sulfuric acid (0.523 ml, 9.82 mmol). The reaction mixture became a solution, and after 30 min it was heated under reflux for 4 h, then RT. The reaction mixture was concentrated, neutralized with a saturated aqueous solution of sodium bicarbonate (pH 8-9) and partitioned with AcOEt. After separation, the organic layer was successively washed with NaHCO₃ sat (×2), water and brine. The aqueous layer was extracted with dichloromethane (×6) and the combined organic layer was dried over anhydrous magnesium sulfate, filtered and concentrated. The crude residue was purified by Biotage (Snap 50 g cartridge, eluted with MeOH/DCM: 0/100 to 03/97 over 15 CV, then 3/97 to 10/90 over 20 CV). The desired fractions were combined, concentrated and dried under high vacuum to afford the desired product (260 mg, 0.142 mmol). Characterization: $^1$H RMN (400 MHz, DMSO-$d_6$): δ (ppm)= 7.28 (bt, J=5.9 Hz, 1H), 4.66 (s, 1H), 3.87 (d, J=5.9 Hz, 2H), 3.66 (s, 3H), 2.35 (t, J=6.1 Hz, 2H), 2.07 (t, J=6.5 Hz, 2H), 1.79 (quint, J=6.4 Hz, 2H), MS (m/z): 183.9 [M+H]$^+$.

Example 10

Synthetic Scheme for the Preparation of ethyl 2-(benzyl(2-oxopropyl)amino)acetate Intermediates

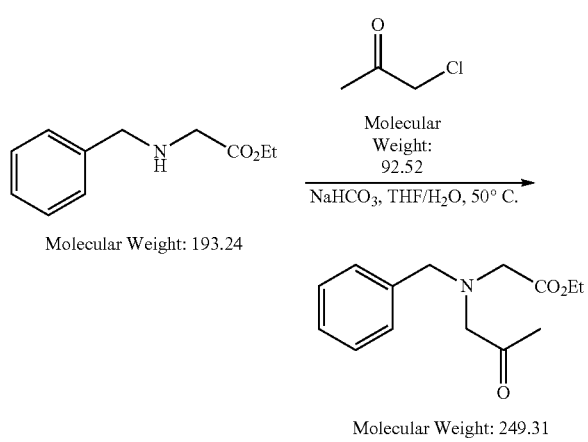

In a 500 mL round bottom flask was added chloroacetone (12.97 mL, 163 mmol) to a suspension of N-benzylglycine ethyl ester (30 g, 155 mmol) and NaHCO₃ (14.34 g, 170 mmol) in THF (333 mL)/water (21 mL) at 50° C. The suspension was heated at 50° C. for 4H. Chloroacetone (0.5 eq, 0.65 ml) and NaHCO3 (1.1 eq, 1.43 g) were added and the solution was heated at 50° C. for 18 h and then concentrated. EA (100 mL) and water (100 mL) were added and the layers were, separated. An extraction was performed with EA (2×50 mL), water (50 mL), brine (50 mL), then dried over Na₂SO₄ and concentrated. 1H NMR showed ratio of SM/product of 1/1.

Example 11

Synthetic Scheme for the Preparation of (E)-2-((3-((4-methoxyphenyl)imino)cyclohex-1-en-1-yl)amino)acetic acid Intermediates

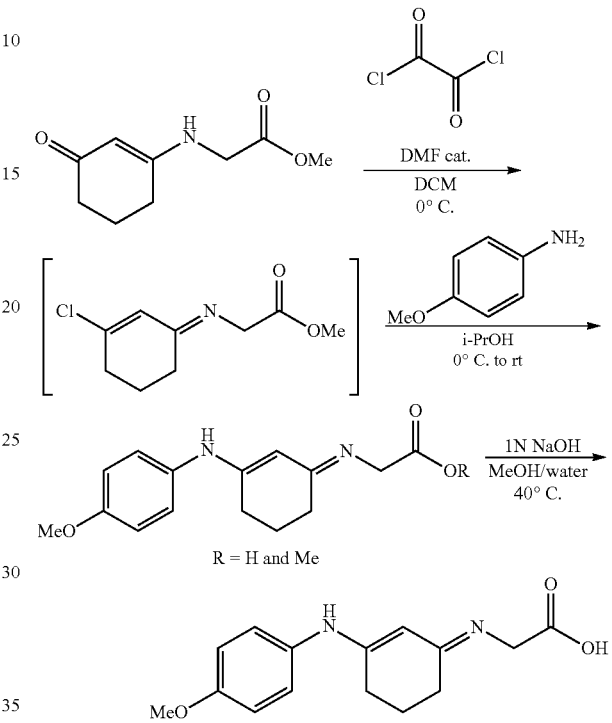

To a stirred solution of methyl 2-((3-oxocyclohex-1-en-1-yl)amino)acetate (255 mg, 1.39 mm ol) in anhydrous DCM (20 ml) at 0° C. and under nitrogen atmosphere were slowly added oxalyl chloride (177 µl, 2.09 mmol) and anhydrous DMF (3 drops). After 1 h, the reaction mixture was concentrated, cooled-down to 0° C., dissolved in isopropanol (15 ml), and a solution of 4-methoxyaniline (171 mg, 1.39 mmol) in isopropanol (5 ml) was added. The reaction mixture was stirred at 0° C. for 15 min, at RT for 3 h, concentrated, and partitioned between AcOEt and water+some saturated NaHCO₃. After separation, the organic layer was successively washed with saturated NaHCO₃, water (×2) and brine. The desired product remained in the aqueous phase. The aqueous layer (pH~9) was extracted with dichloromethane (×9), and the combined organic layer (only DCM) was concentrated. The aqueous layer was concentrated, suspended in MeOH, filtered, combined with the crude residue (from DCM), and concentrated. The crude residue was purified by Biotage (reverse phase C18-Snap 30 g cartridge, eluted with MeOH/water: 5/95 to 95/05 over 50 CV, 254 nm for the wavelength collection). Hydrolysis of the methyl ester occurred partially during the purification. The desired fractions were combined, half-concentrated at 40° C., treated with 1N NaOH (10 ml), concentrated at 40° C., suspended in MeOH, filtered, concentrated, and the crude residue was purified by Biotage (reverse phase C18-Snap 30 g cartridge, eluted with MeOH/water: 5/95 to 95/05 over 50 CV, 320 nm for the wavelength collection). The desired fractions were combined, concentrated, and dried under high vacuum to afford the desired product (114 mg, 0.416 mmol, 30% yield over three steps) as a beige/light brown powder. Characterization: $^1$H RMN (400 MHz, CDCl$_3$): δ (ppm)=mixture of tautomers and/or isomers, one H is missing, 7.14-6.70 (m, 4H), 5.80-5.00 (2 m, 1H), 3.86-3.30 (m, 6H), 2.80-2.10 (m, 4H), 1.93-1.54 (m, 2H). MS (m/z): 275.05 [M+H]$^+$ HPLC: >98% UV: λ$_{max}$ ~318 nm (MeOH/water with both 0.1% formic acid); Range from 280 to 380 nm.

Example 12

Synthetic Scheme for the Preparation of Methyl 2-((5,5-dimethyl-3-oxocyclohex-1-en-1-yl)amino) acetate and 3-methoxy-5,5-dimethylcyclohex-2-enone Intermediates

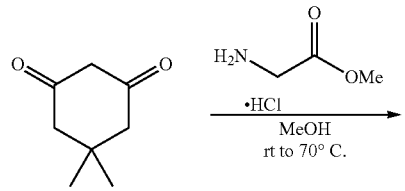

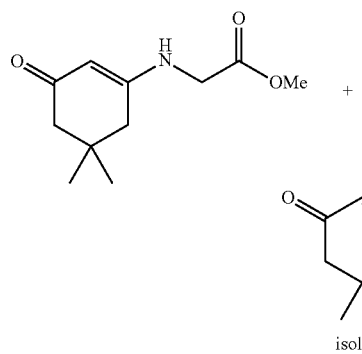

A stirred solution of dimedone (5 g, 35.67 mmol) and methyl glycine ester hydrochloride (4.926 g, 39.24 mmol) in methanol (50 ml) under nitrogen atmosphere was heated at 60-65° C. overnight, then was added more methyl glycine ester hydrochloride (4.926 g, 39.24 mmol). The reaction mixture was heated at 70° C. for few hours, concentrated, diluted with water, kept in the freezer over weekend, then RT, and diluted with AcOEt. After separation, the organic layer was successively washed with water, a saturated aqueous solution of sodium bicarbonate and brine. The aqueous layer was extracted once with AcOEt, and washed with water and brine afterwards. The combined organic layer was dried over anhydrous magnesium sulfate, filtered, and concentrated. The crude product (3-methoxy-5,5-dimethylcyclohex-2-enone, 4.581 g) was used in the next step without any further purification. Characterization: $^1$H NMR (400 MHz, DMSO-d$_6$): δ(ppm)=5.31 (s, 1H), 3.67 (s, 3H), 2.28 (s, 2H), 2.11 (s, 2H), 0.97 (s, 6H). MS (m/z): 154.93 [M+H]$^+$ and 211.97 (traces).

Example 13

Synthetic Scheme for the Preparation of (R)-ethyl 6,6-dimethyl-8-oxo-3,4,5,6,7,8-hexahydro-2H-benzo[b][1,4]thiazine-3-carboxylate Intermediate

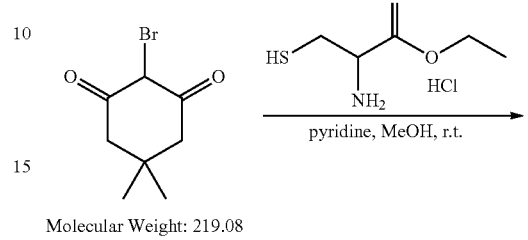

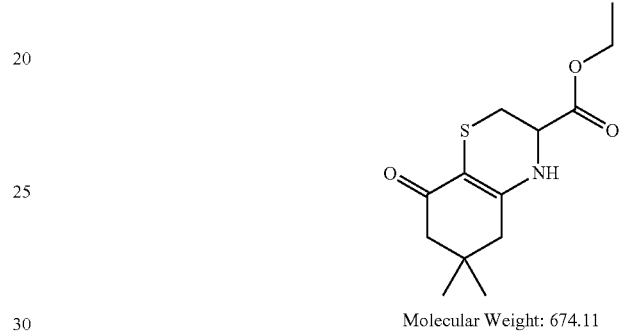

In a 500 mL round bottom flask was added L-cysteine ethyl ester HCl (10.47 g, 56.38 mmol) to a solution of 2-bromo-5,5-dimethyl-cyclohexane-1,3-dione (11.23 g, 11.23 mmol) and pyridine (12.43 mL, 153.7 mmol) in MeOH (170 mL). The solution was stirred at RT for 2.5 days and was concentrated. EA (100 mL), water (100 mL) and HCl 1N (75 mL) were added. The layers were then separated. Extraction was performed with EA (2×100 mL), brine (50 mL), the solution was dried over Na$_2$SO$_4$ and then concentrated.

Example 14

Synthetic Scheme for the Preparation of (R)-ethyl 8-chloro-6,6-dimethyl-3,5,6,7-tetrahydro-2H-benzo[b][1,4]thiazine-3-carboxylate Intermediate

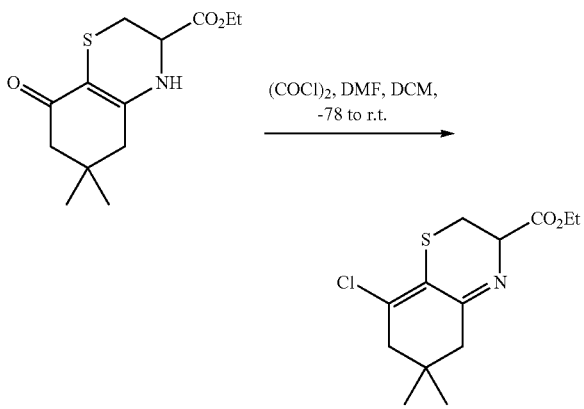

In a 100 mL round bottom flask was added (COCl)$_2$ (4.11 ml, 48.59 mmol) to a solution of (R)-ethyl 6,6-dimethyl-8-oxo-3,4,5,6,7,8-hexahydro-2H-benzo[b][1,4]thiazine-3-carboxylate (11.9 g, 44.17 mmol) in DCM (100 mL). After cooling to −78° C., DMF (2 drops) was added to the solution at −78° C. After 1 h at −78° C., the solution was warm to 0° C. over 1 h and stirred at 0° C. for 2 h. Water was added (100 mL) and the layers were separated. Extraction was performed with DCM (2×50 mL), NaHCO$_3$ (50 mL), brine (50 mL), the solution was dried over Na$_2$SO$_4$ and was concentrated. The residue was purified via Biotage (0 to 30% of EA in Hex over 30 CV; 100 g column).

Example 15

Synthetic scheme for the preparation of (R)-ethyl 8-((4-methoxyphenyl)amino)-6,6-dimethyl-3,5,6,7-tetrahydro-2H-benzo[b][1,4]thiazine-3-carboxylate Intermediate

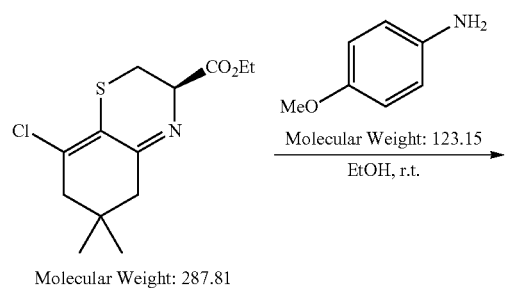

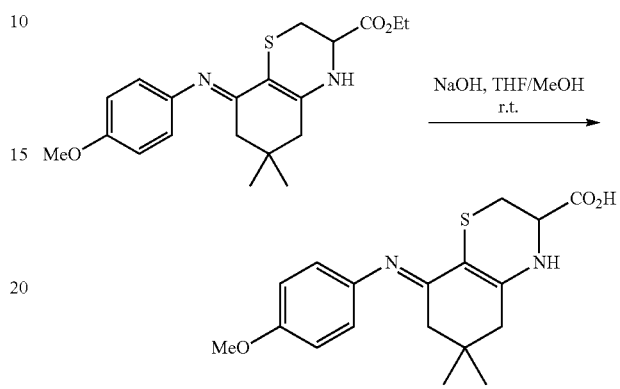

In a 250 mL round bottom flask was added p-anisidine (673 mg, 5.47 mmol) to a solution of (R)-ethyl 8-chloro-6,6-dimethyl-3,5,6,7-tetrahydro-2H-benzo[b][1,4]thiazine-3-carboxylate (1.5 g, 5.21 mmol) in EtOH (50 mL). The solution was stirred at RT for 20 h and concentrated. Addition of DCM (100 ml), water (100 mL) and NaHCO$_3$ (50 mL), separation of layers. Extracted with DCM (2×100 mL), dry over Na$_2$SO$_4$ and concentrated. The residue was purified via Biotage (0% to 5% of MeOH in DCM over 20 CV; 100 g column).

Example 16

Synthetic Scheme for the Preparation of (R)-8-((4-methoxyphenyl)amino)-6,6-dimethyl-3,5,6,7-tetrahydro-2H-benzo[b][1,4]thiazine-3-carboxylic acid Intermediate In a 250 mL round bottom flask was added NaOH 1M (10 mL, 10 mmol) to a solution of (R,E)-ethyl 8-((4-methoxyphenyl)imino)-6,6-dimethyl-3,4,5,6,7,8-hexahydro-2H-benzo[b][1,4]thiazine-3-carboxylate (0.5 g, 1.73 mmol) in a mixture of MeOH (20 mL)/THF (20 mL). The solution was stirred at RT for 1 h and concentrated. Addition of water (40 mL) and HCl 1M (~30 mL) to pH 7, concentrated. Azeotroped with EtOH (2×40 mL). Triturated in EtOH (30 mL) for 10 min, filtered, washed with EtOH (2×10 mL). A white solid, salt was discarded. The filtrate was concentrated. The residue was purified via Biotage (20 to 95% of MeOH in H$_2$O over 60 CV; 30 g KP-C18-HS column).

Example 17

Synthetic Scheme for the Preparation of 2-((3-oxocyclohex-1-en-1-yl)amino)acetic acid Intermediate

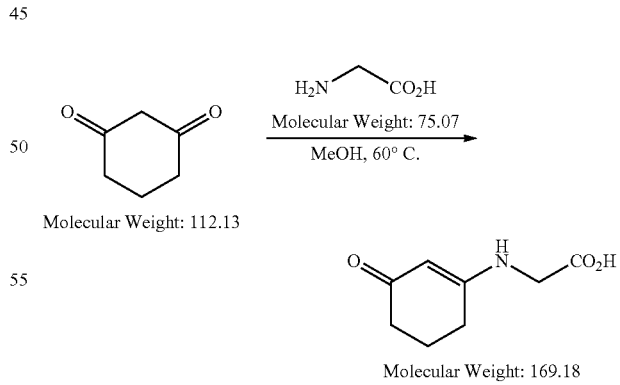

In a 500 ml round bottom flask was added glycine (2.28 g, 30.41 mmol) to a suspension of 1,3-cyclohexanedione (3.10 g, 27.64 mmol) in MeOH (200 mL). The suspension was heated at 60° C. for 19 h. After cooling down to RT, the suspension was concentrated and triturated in MeOH (40 mL) for 1 h, filtered, washed with MeOH (2×10 mL) and dried under vacuum for 4 h resulting in 3.56 g of a light yellow solid, soluble in water, insoluble in acetone, MeOH and slightly soluble in DMSO.

Example 18

Synthetic Scheme for the Preparation of 3-((4-methoxyphenyl)amino)cyclohex-2-enone Intermediate

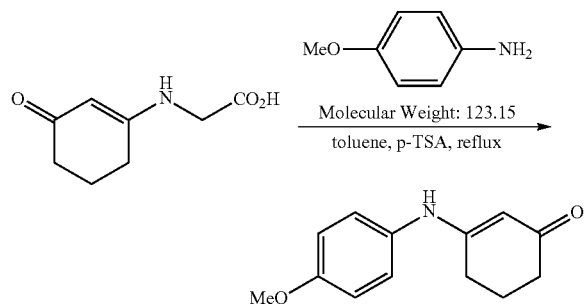

In a 500 mL round bottom flask was added p-anisidine (800 mg, 6.50 mmol) to a suspension of 2-((3-oxocyclohex-1-en-1-yl)amino)acetic acid (1.00 g, 5.91 mmol) in Toluene (100 mL). The suspension was heated at reflux with a dean stark apparatus for 19 h. After cooling down to RT, the suspension was filtered, washed with toluene (2×10 mL) and dried under vacuum for 4 h.

Example 19

In a 500 mL round bottom flask was added p-Anisidine (800 mg, 6.50 mmol) to a suspension of 2-((3-oxocyclohex-1-en-1-yl)amino)acetic acid (1.00 g, 5.91 mmol) and p-TSA.H2O (1.12 g, 5.91 mmol). The suspension was heated at reflux for 1 h. After cooling down to RT, DCM (50 mL), water (100 mL) and NH₄Cl (25 mL) were added. The resulting layers were separated. An extraction was performed with DCM (2×50 mL). The extracted portion was dried over Na₂SO₄ and concentrated. The residue was purified via Biotage (0 to 10% of MeOH in DCM over 20 CV; 25 g column).

Example 20

Synthetic Scheme for the Preparation of (R)-ethyl 6,6-dimethyl-8-oxo-3,4,5,6,7,8-hexahydro-2H-benzo[b][1,4]thiazine-3-carboxylate

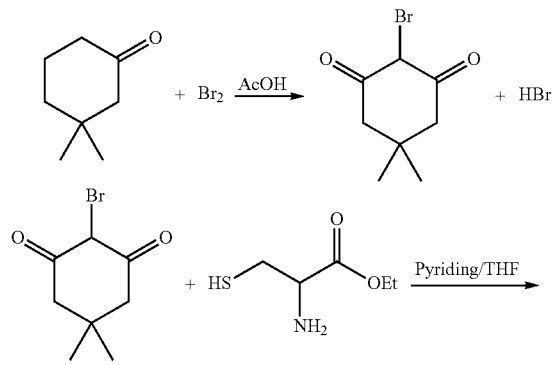

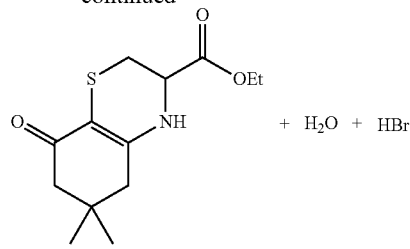

A mixture of dimedone (43.82 g, 1.0 equiv) in 392 mL of AcOH (14 vol) was added drop-wise with bromine (31.96 g, 1.0 equiv) at 20-40° C. Solid precipitated during the adding of bromine. After addition, the resulting suspension was kept at ~30° C. for at another ~4 hours until no dimedone remaining. Filter the suspension by suction, the cake was washed twice with 140 mL of MTBE (2×5 vol), then the cake was collected and dried under 50° C. in the vacuum oven for ~8 hours to give 35.1 g of 2-bromo-5,5-dimethyl-cyclohexane-1,3-dione as white solid. The isolated yield was 80.1%, the purity was 97.4%. To the stirred solution of 2-bromo-5,5-dimethyl-cyclohexane-1,3-dione (43.82 g, 1.0 equiv) and L-cysteine ethyl ester (32.83 g, 1.1 equiv) in 350 mL of THF (8 vol), was added with pyridine (31.64 g, 2.0 equiv) in one portion. After addition, the reaction mixture was refluxed (65~70° C.) under N₂ for ~4 hours. The reaction mixture cooled down and concentrated to dryness. The residue was diluted with methanol (131 mL, 3 vol) and the solution was poured into cold water (394 mL, 9 vol) while stirring. The resulting suspension was kept at 20~30° C. for another 1 hour. The suspension was filtered by suction, the cake was collected and re-dissolved in 53 mL of EA (53 mL) at 70~80° C. The solution was cooled down to 0~10° C. and kept at this temperature for another 1 hour. The suspension was filtered by suction, the cake was washed with 10 mL of cold EA (0.2 vol). The cake was collected and dried below 45° C. in the vacuum oven for at least 4 hours to give (R)-ethyl 6,6-dimethyl-8-oxo-3,4,5,6,7,8-hexahydro-2H-benzo[b][1,4]thiazine-3-carboxylate.

Example 21

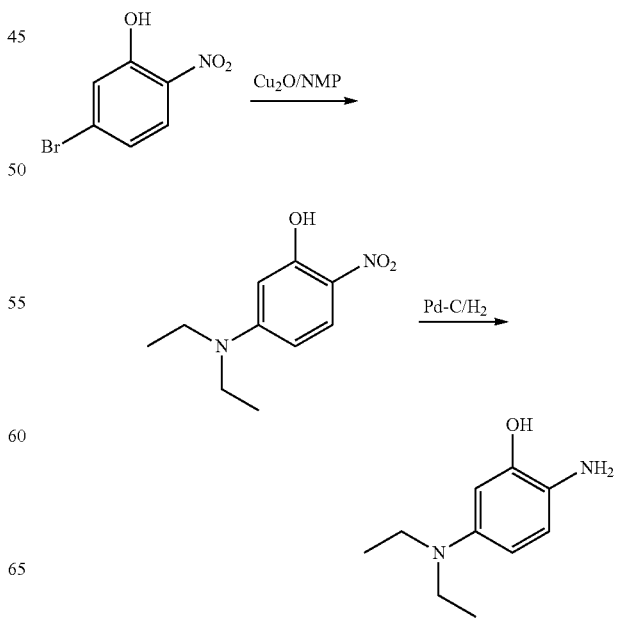

To a solution of 5-bromo-2-nitrophenol in diethylamine was added copper dioxide and N-methypyridine (1 eq) the mixture was heated at 110 C for 20 h; workup and column purification gave 5-(diethylamino)-2-nitrophenol in 30% yield. Then reduction of 5-(diethylamino)-2-nitrophenol was done using hydrogen on Pd/C in ethanol to give quantitative yield of 2-amino-5-(diethylamino)phenol.

Example 22

Synthesis Scheme for the Compound of Formula IE$_2$

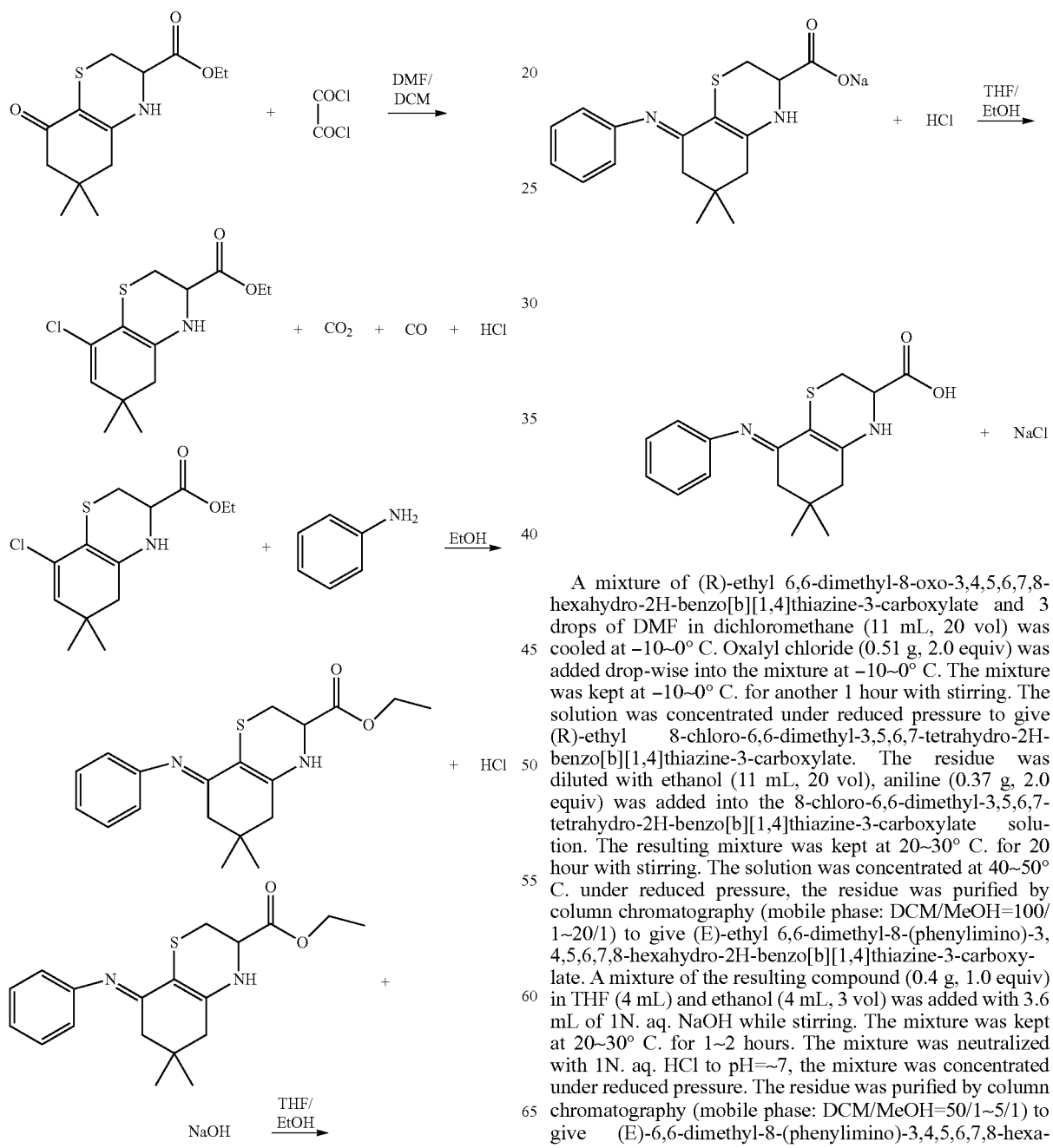

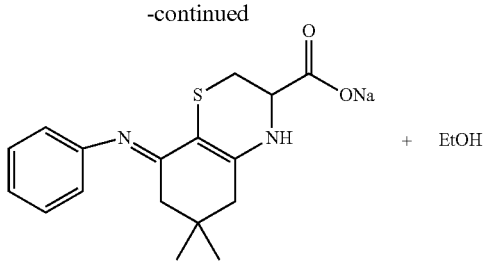

A mixture of (R)-ethyl 6,6-dimethyl-8-oxo-3,4,5,6,7,8-hexahydro-2H-benzo[b][1,4]thiazine-3-carboxylate and 3 drops of DMF in dichloromethane (11 mL, 20 vol) was cooled at −10~0° C. Oxalyl chloride (0.51 g, 2.0 equiv) was added drop-wise into the mixture at −10~0° C. The mixture was kept at −10~0° C. for another 1 hour with stirring. The solution was concentrated under reduced pressure to give (R)-ethyl 8-chloro-6,6-dimethyl-3,5,6,7-tetrahydro-2H-benzo[b][1,4]thiazine-3-carboxylate. The residue was diluted with ethanol (11 mL, 20 vol), aniline (0.37 g, 2.0 equiv) was added into the 8-chloro-6,6-dimethyl-3,5,6,7-tetrahydro-2H-benzo[b][1,4]thiazine-3-carboxylate solution. The resulting mixture was kept at 20~30° C. for 20 hour with stirring. The solution was concentrated at 40~50° C. under reduced pressure, the residue was purified by column chromatography (mobile phase: DCM/MeOH=100/1~20/1) to give (E)-ethyl 6,6-dimethyl-8-(phenylimino)-3,4,5,6,7,8-hexahydro-2H-benzo[b][1,4]thiazine-3-carboxylate. A mixture of the resulting compound (0.4 g, 1.0 equiv) in THF (4 mL) and ethanol (4 mL, 3 vol) was added with 3.6 mL of 1N. aq. NaOH while stirring. The mixture was kept at 20~30° C. for 1~2 hours. The mixture was neutralized with 1N. aq. HCl to pH=~7, the mixture was concentrated under reduced pressure. The residue was purified by column chromatography (mobile phase: DCM/MeOH=50/1~5/1) to give (E)-6,6-dimethyl-8-(phenylimino)-3,4,5,6,7,8-hexahydro-2H-benzo[b][1,4]thiazine-3-carboxylic acid.

Example 23

Synthesis Scheme for the Compound of Formula IF$_1$

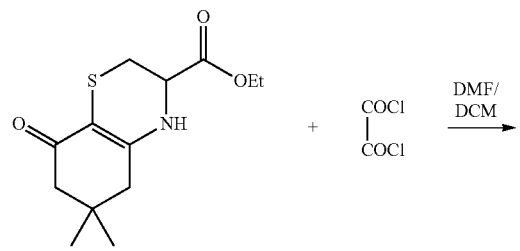

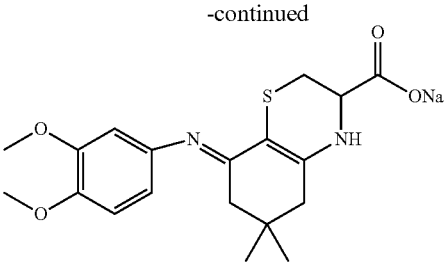

+ EtOH

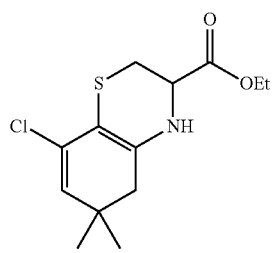

+ CO$_2$ + CO + HCl

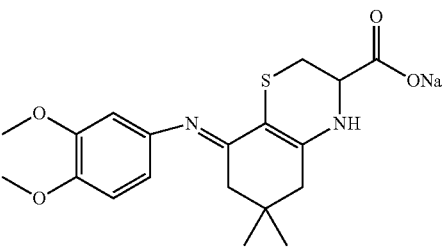

+

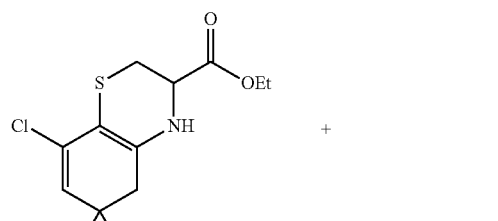

HCl $\xrightarrow{\text{THF/EtOH}}$

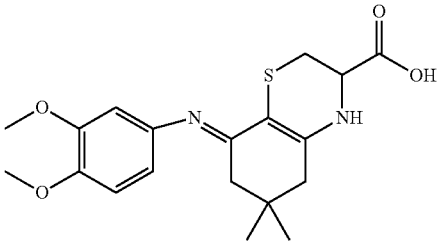

+ NaCl

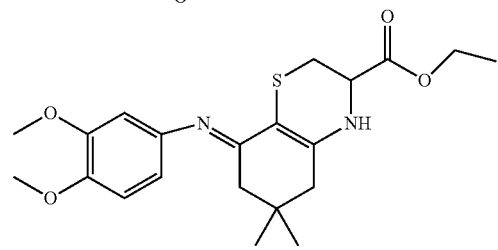

+ HCl

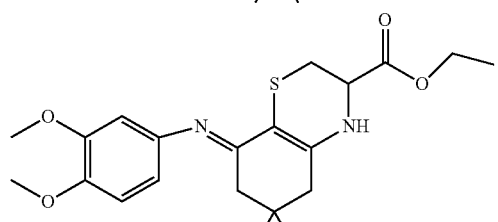

+

NaOH $\xrightarrow{\text{THF/EtOH}}$

A mixture of (R)-ethyl 6,6-dimethyl-8-oxo-3,4,5,6,7,8-hexahydro-2H-benzo[b][1,4]thiazine-3-carboxylate (1.5 g, 1.0 equiv) and 3 drops of DMF in dichloromethane (15 mL, 10 vol) was cooled at −10∼0° C. Oxalyl chloride (1.4 g, 2.0 equiv) was added drop-wise into the mixture at −10∼0° C., the mixture was kept at −10∼0° C. for another 1 hour with stirring. The solution was concentrated at NMT 40° C. under reduced pressure to give (R)-ethyl 8-chloro-6,6-dimethyl-3,5,6,7-tetrahydro-2H-benzo[b][1,4]thiazine-3-carboxylate. The residue was diluted with ethanol (15 mL, 10 vol), EK-B7 (1.7 g, 2.0 equiv) was added into the (R)-ethyl 8-chloro-6,6-dimethyl-3,5,6,7-tetrahydro-2H-benzo[b][1,4]thiazine-3-carboxylate solution, the resulting mixture was kept at 20∼30° C. for 20 hour with stirring. The solution was concentrated at 40∼50° C. under reduced pressure, the residue was purified by column chromatography (mobile phase: DCM/MeOH=100/1∼20/1) to give (E)-ethyl 8-((3,4-dimethoxyphenyl)imino)-6,6-dimethyl-3,4,5,6,7,8-hexahydro-2H-benzo[b][1,4]thiazine-3-carboxylate. A mixture of (E)-ethyl 8-((3,4-dimethoxyphenyl)imino)-6,6-dimethyl-3,4,5,6,7,8-hexahydro-2H-benzo[b][1,4]thiazine-3-carboxylate (1.0 g, 1.0 equiv) in THF (5 mL) and ethanol (5 mL, 5 vol) was added with 1N. aq. NaOH, the mixture was kept at 20∼30° C. for 1∼2 hours. The mixture was neutralized with 1N. aq. HCl to pH=∼7, and concentrated under reduced pressure. The residue was purified by column chromatography (mobile phase: DCM/MeOH=50/1∼5/1) to give compound IF$_1$.

Example 24

Synthesis Scheme for the Compound of Formula ID$_2$

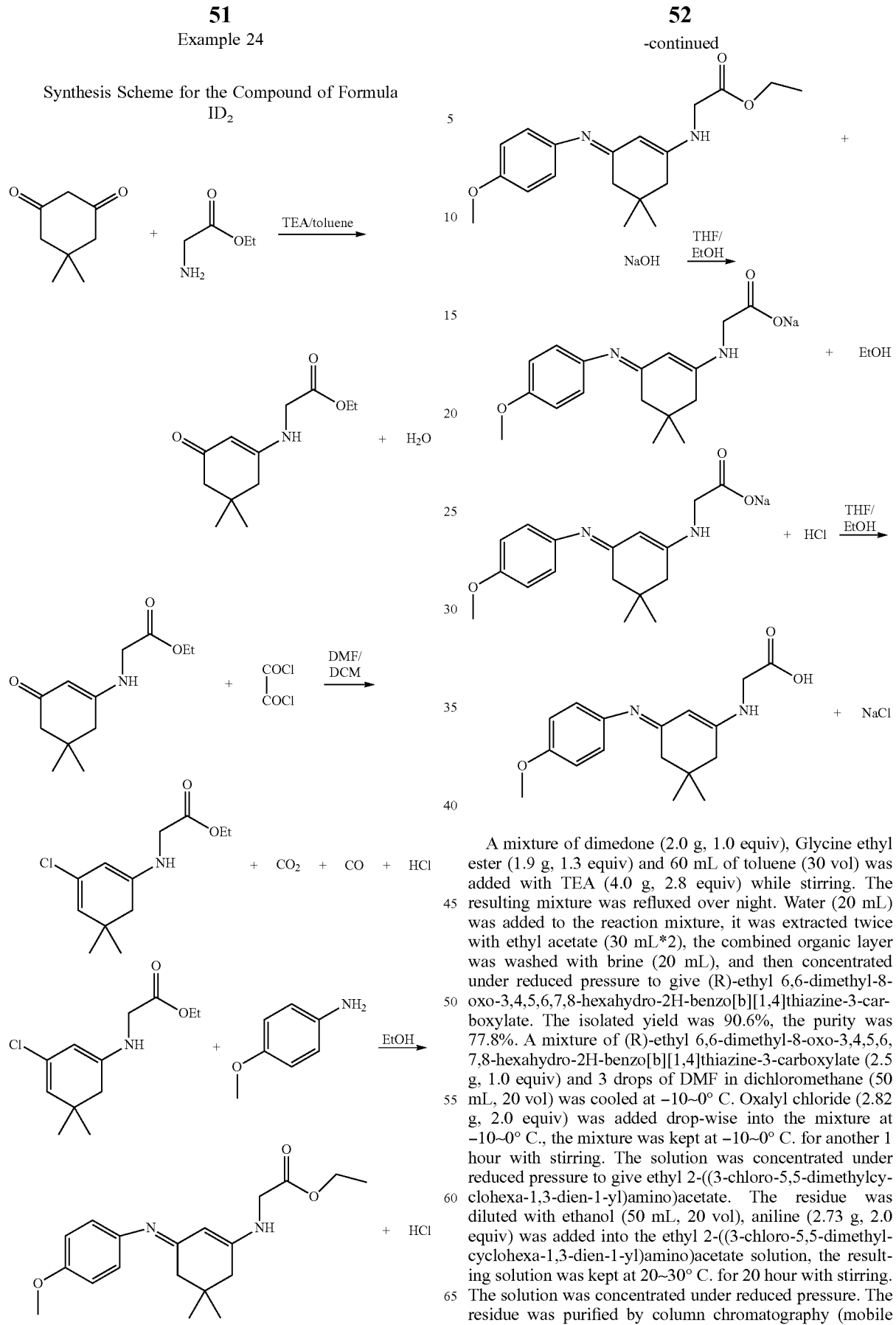

A mixture of dimedone (2.0 g, 1.0 equiv), Glycine ethyl ester (1.9 g, 1.3 equiv) and 60 mL of toluene (30 vol) was added with TEA (4.0 g, 2.8 equiv) while stirring. The resulting mixture was refluxed over night. Water (20 mL) was added to the reaction mixture, it was extracted twice with ethyl acetate (30 mL*2), the combined organic layer was washed with brine (20 mL), and then concentrated under reduced pressure to give (R)-ethyl 6,6-dimethyl-8-oxo-3,4,5,6,7,8-hexahydro-2H-benzo[b][1,4]thiazine-3-carboxylate. The isolated yield was 90.6%, the purity was 77.8%. A mixture of (R)-ethyl 6,6-dimethyl-8-oxo-3,4,5,6,7,8-hexahydro-2H-benzo[b][1,4]thiazine-3-carboxylate (2.5 g, 1.0 equiv) and 3 drops of DMF in dichloromethane (50 mL, 20 vol) was cooled at −10~0° C. Oxalyl chloride (2.82 g, 2.0 equiv) was added drop-wise into the mixture at −10~0° C., the mixture was kept at −10~0° C. for another 1 hour with stirring. The solution was concentrated under reduced pressure to give ethyl 2-((3-chloro-5,5-dimethylcyclohexa-1,3-dien-1-yl)amino)acetate. The residue was diluted with ethanol (50 mL, 20 vol), aniline (2.73 g, 2.0 equiv) was added into the ethyl 2-((3-chloro-5,5-dimethylcyclohexa-1,3-dien-1-yl)amino)acetate solution, the resulting solution was kept at 20~30° C. for 20 hour with stirring. The solution was concentrated under reduced pressure. The residue was purified by column chromatography (mobile phase: DCM/MeOH=100/1~20/1) to give (E)-ethyl 2-((3-

((4-methoxyphenyl)imino)-5,5-dimethylcyclohex-1-en-1-yl)amino)acetate. A mixture of (E)-ethyl 2-((3-((4-methoxyphenyl)imino)-5,5-dimethylcyclohex-1-en-1-yl)amino)acetate (1.2 g, 1.0 equiv) in THF (12 mL) and ethanol (12 mL) was added with 18 mL of 1N. aq. NaOH while stirring, the mixture was kept at 20~30° C. for 1~2 hours. The mixture was neutralized with 1N. aq. HCl to pH=~7, and concentrated at 40~50° C. under reduced pressure. The residue was purified by column chromatography (mobile phase: DCM/MeOH=50/1~5/1) to give compound $ID_2$.

Example 25

Synthesis Scheme for the Compound of Formula $ID_3$

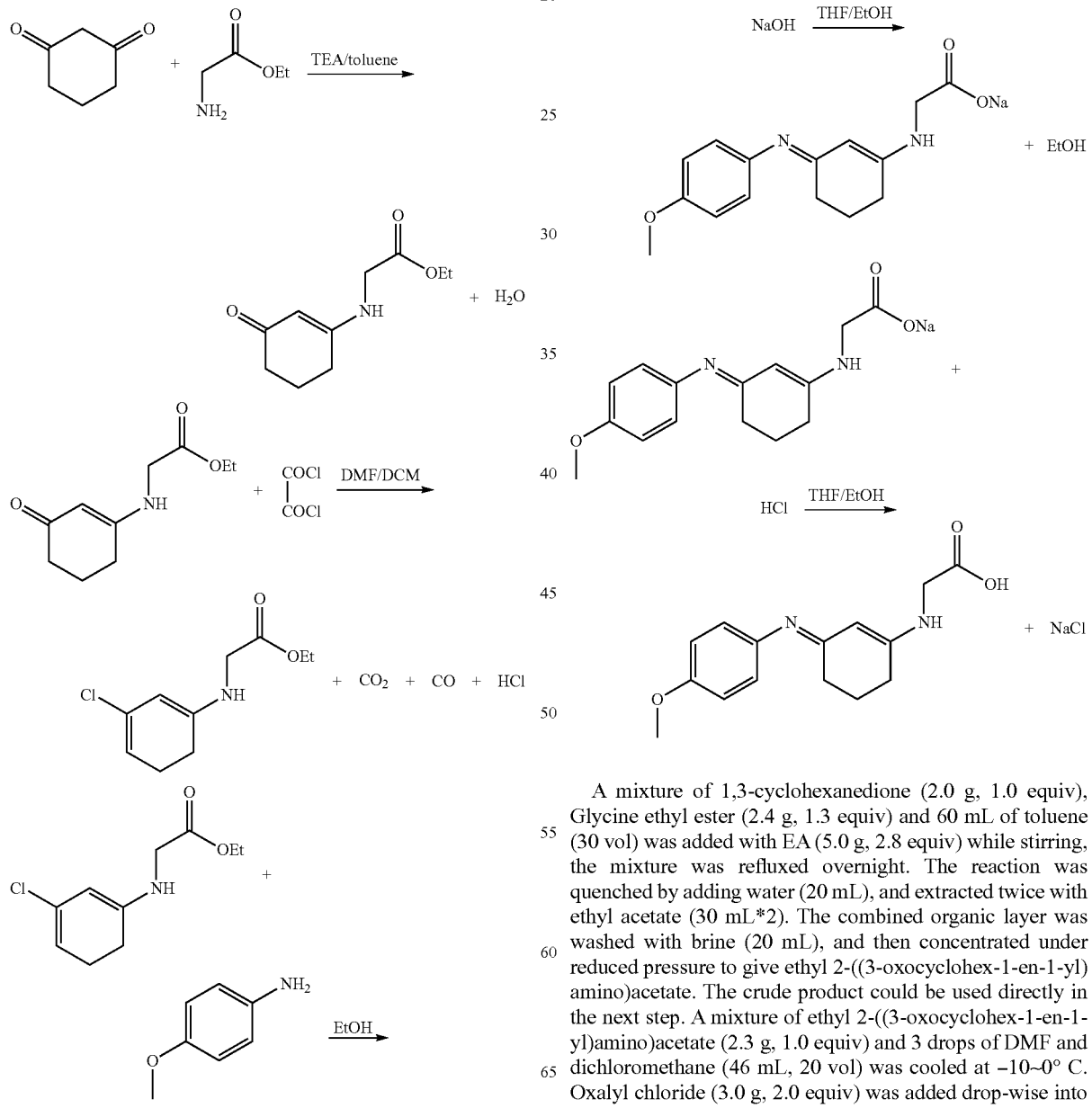

A mixture of 1,3-cyclohexanedione (2.0 g, 1.0 equiv), Glycine ethyl ester (2.4 g, 1.3 equiv) and 60 mL of toluene (30 vol) was added with EA (5.0 g, 2.8 equiv) while stirring, the mixture was refluxed overnight. The reaction was quenched by adding water (20 mL), and extracted twice with ethyl acetate (30 mL*2). The combined organic layer was washed with brine (20 mL), and then concentrated under reduced pressure to give ethyl 2-((3-oxocyclohex-1-en-1-yl)amino)acetate. The crude product could be used directly in the next step. A mixture of ethyl 2-((3-oxocyclohex-1-en-1-yl)amino)acetate (2.3 g, 1.0 equiv) and 3 drops of DMF and dichloromethane (46 mL, 20 vol) was cooled at −10~0° C. Oxalyl chloride (3.0 g, 2.0 equiv) was added drop-wise into the mixture at −10~0° C., the mixture was kept at −10~0° C.

for another 1 hour with stirring. The solution was concentrated under reduced pressure to give ethyl 2-((3-chlorocyclohexa-1,3-dien-1-yl)amino)acetate. The residue above was diluted with ethanol (46 mL, 20 vol), 4-methoxyaniline (2.9 g, 2.0 equiv) was added into the ethyl 2-((3-chlorocyclohexa-1,3-dien-1-yl)amino)acetate solution, the resulting mixture was kept at 20~30° C. for 20 hours with stirring. The solution was concentrated under reduced pressure. The residue was purified by column chromatography (mobile phase: DCM/MeOH=100/1~20/1) to give 1.7 g of (E)-ethyl 2-((3-((4-methoxyphenyl)imino)cyclohex-1-en-1-yl)amino)acetate. A mixture of (E)-ethyl 2-((3-((4-methoxyphenyl)imino)cyclohex-1-en-1-yl)amino)acetate (1.7 g, 1.0 equiv) in THF (17 mL) and ethanol (17 mL) was added with 28 mL of 1N. aq. NaOH while stirring, the mixture was kept at 20~30° C. for 1~2 hours. The mixture was neutralized with 1N. aq. HCl to pH=~7, concentrated under reduced pressure. The residue was purified by column chromatography (mobile phase: DCM/MeOH=50/1~5/1) to give compound ID$_3$.

Example 26

Synthesis Scheme for the Compound of Formula IE$_1$

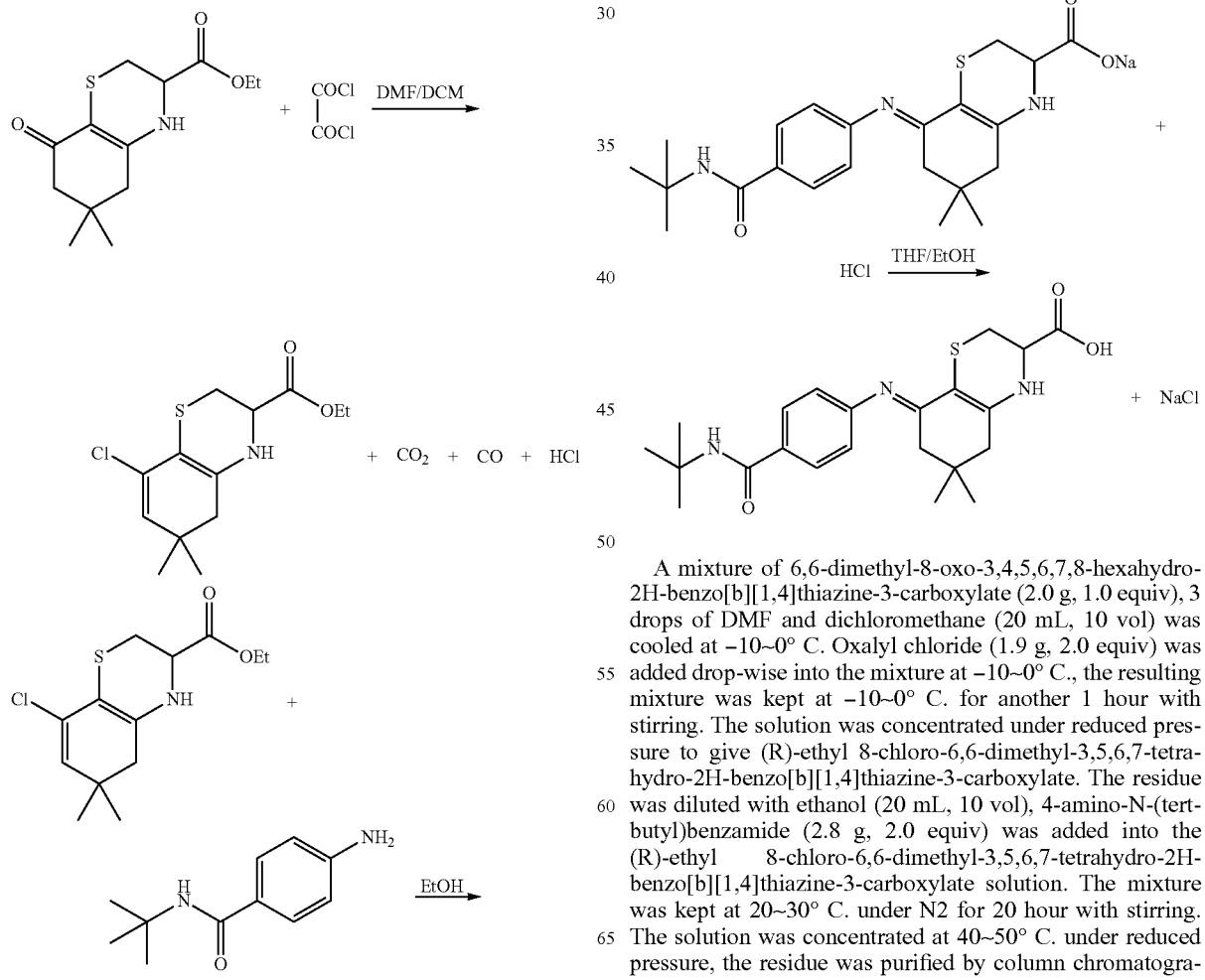

A mixture of 6,6-dimethyl-8-oxo-3,4,5,6,7,8-hexahydro-2H-benzo[b][1,4]thiazine-3-carboxylate (2.0 g, 1.0 equiv), 3 drops of DMF and dichloromethane (20 mL, 10 vol) was cooled at −10~0° C. Oxalyl chloride (1.9 g, 2.0 equiv) was added drop-wise into the mixture at −10~0° C., the resulting mixture was kept at −10~0° C. for another 1 hour with stirring. The solution was concentrated under reduced pressure to give (R)-ethyl 8-chloro-6,6-dimethyl-3,5,6,7-tetrahydro-2H-benzo[b][1,4]thiazine-3-carboxylate. The residue was diluted with ethanol (20 mL, 10 vol), 4-amino-N-(tert-butyl)benzamide (2.8 g, 2.0 equiv) was added into the (R)-ethyl 8-chloro-6,6-dimethyl-3,5,6,7-tetrahydro-2H-benzo[b][1,4]thiazine-3-carboxylate solution. The mixture was kept at 20~30° C. under N2 for 20 hour with stirring. The solution was concentrated at 40~50° C. under reduced pressure, the residue was purified by column chromatography (mobile phase: DCM/MeOH=100/1~20/1) to give (E)- ethyl 8-((4-(tert-butylcarbamoyl)phenyl)imino)-6,6-dimethyl-3,4,5,6,7,8-hexahydro-2H-benzo[b][1,4]thiazine-3-carboxylate. To a stirred solution of (E)-ethyl 8-((4-(tert-butylcarbamoyl)phenyl)imino)-6,6-dimethyl-3,4,5,6,7,8-hexahydro-2H-benzo[b][1,4]thiazine-3-carboxylate (0.8 g, 1.0 equiv) in THF (4 mL) and ethanol (4 mL, 3 vol) was added with 1N. aq. NaOH at 20~30° C., the resulting solution was kept at this temperature for another 1~2 hours. The mixture was neutralized with 1N. aq. HCl to pH=~7, the resulting solution was concentrated under reduced pressure. The residue was purified by column chromatography (mobile phase: DCM/MeOH=50/1~5/1) to give compound $IE_1$.

Example 27

Synthesis Scheme for the Compound of Formula $IA_2$

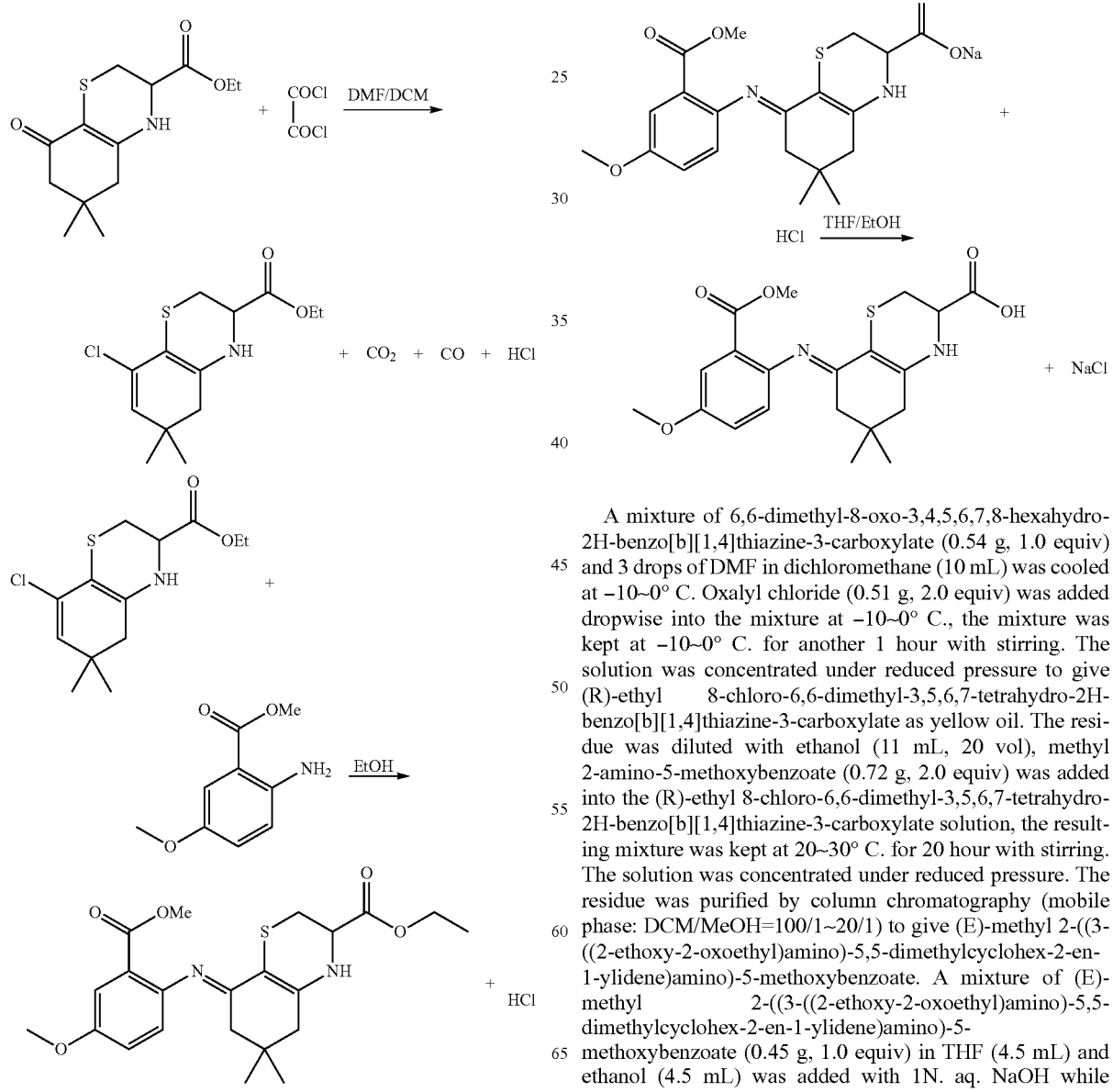

A mixture of 6,6-dimethyl-8-oxo-3,4,5,6,7,8-hexahydro-2H-benzo[b][1,4]thiazine-3-carboxylate (0.54 g, 1.0 equiv) and 3 drops of DMF in dichloromethane (10 mL) was cooled at −10~0° C. Oxalyl chloride (0.51 g, 2.0 equiv) was added dropwise into the mixture at −10~0° C., the mixture was kept at −10~0° C. for another 1 hour with stirring. The solution was concentrated under reduced pressure to give (R)-ethyl 8-chloro-6,6-dimethyl-3,5,6,7-tetrahydro-2H-benzo[b][1,4]thiazine-3-carboxylate as yellow oil. The residue was diluted with ethanol (11 mL, 20 vol), methyl 2-amino-5-methoxybenzoate (0.72 g, 2.0 equiv) was added into the (R)-ethyl 8-chloro-6,6-dimethyl-3,5,6,7-tetrahydro-2H-benzo[b][1,4]thiazine-3-carboxylate solution, the resulting mixture was kept at 20~30° C. for 20 hour with stirring. The solution was concentrated under reduced pressure. The residue was purified by column chromatography (mobile phase: DCM/MeOH=100/1~20/1) to give (E)-methyl 2-((3-((2-ethoxy-2-oxoethyl)amino)-5,5-dimethylcyclohex-2-en-1-ylidene)amino)-5-methoxybenzoate. A mixture of (E)-methyl 2-((3-((2-ethoxy-2-oxoethyl)amino)-5,5-dimethylcyclohex-2-en-1-ylidene)amino)-5-methoxybenzoate (0.45 g, 1.0 equiv) in THF (4.5 mL) and ethanol (4.5 mL) was added with 1N. aq. NaOH while stirring, the mixture was kept at 20~30° C. for 1~2 hours.

The mixture was neutralized with 1N. aq. HCl to pH=~7, and concentrated under reduced pressure. The residue was purified by column chromatography (mobile phase: DCM/MeOH=50/1~5/1) to give compound $IA_2$.

Example 28

Synthesis Scheme for the Compound of Formula $IE_4$

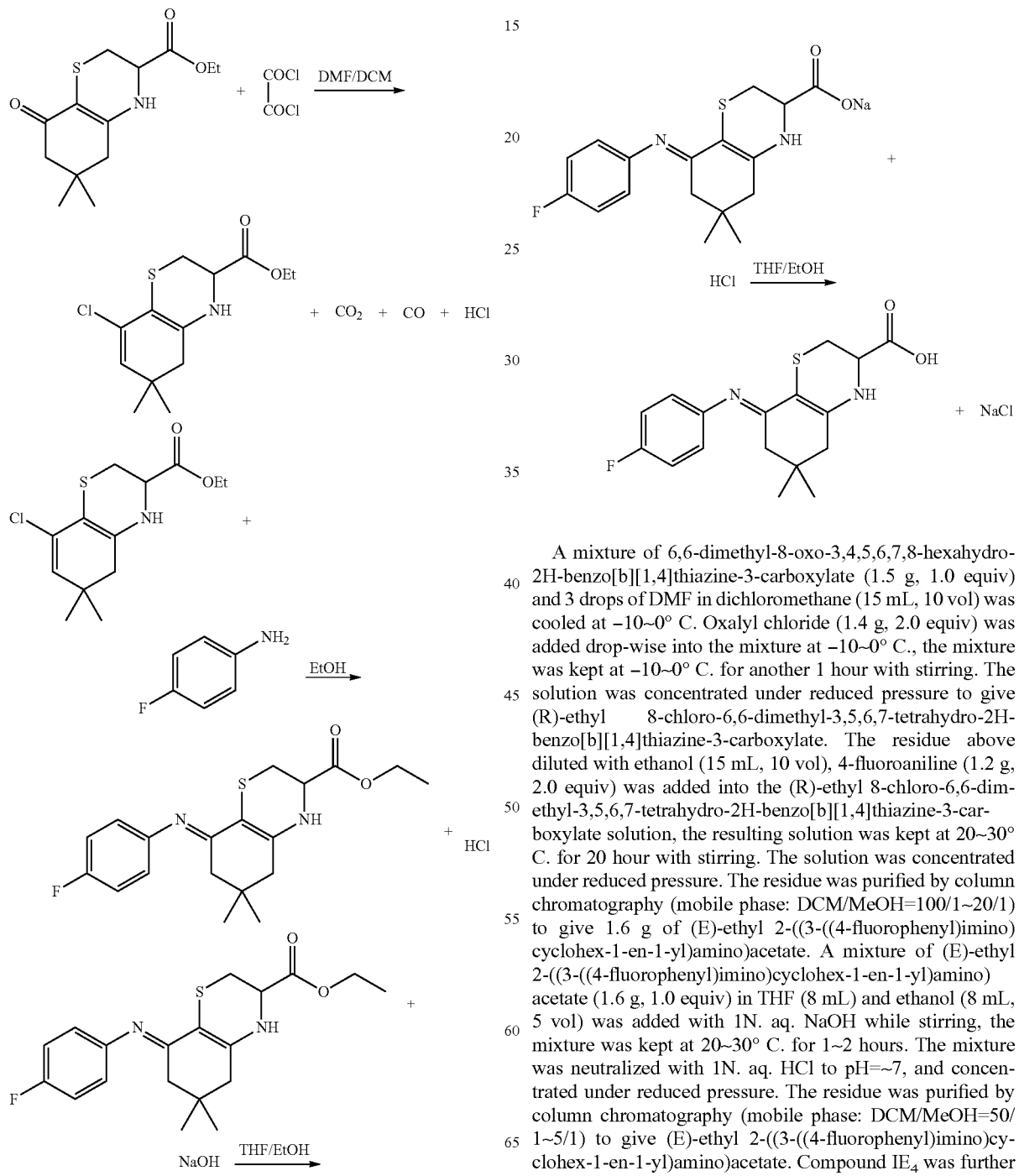

A mixture of 6,6-dimethyl-8-oxo-3,4,5,6,7,8-hexahydro-2H-benzo[b][1,4]thiazine-3-carboxylate (1.5 g, 1.0 equiv) and 3 drops of DMF in dichloromethane (15 mL, 10 vol) was cooled at −10~0° C. Oxalyl chloride (1.4 g, 2.0 equiv) was added drop-wise into the mixture at −10~0° C., the mixture was kept at −10~0° C. for another 1 hour with stirring. The solution was concentrated under reduced pressure to give (R)-ethyl 8-chloro-6,6-dimethyl-3,5,6,7-tetrahydro-2H-benzo[b][1,4]thiazine-3-carboxylate. The residue above diluted with ethanol (15 mL, 10 vol), 4-fluoroaniline (1.2 g, 2.0 equiv) was added into the (R)-ethyl 8-chloro-6,6-dimethyl-3,5,6,7-tetrahydro-2H-benzo[b][1,4]thiazine-3-carboxylate solution, the resulting solution was kept at 20~30° C. for 20 hour with stirring. The solution was concentrated under reduced pressure. The residue was purified by column chromatography (mobile phase: DCM/MeOH=100/1~20/1) to give 1.6 g of (E)-ethyl 2-((3-((4-fluorophenyl)imino)cyclohex-1-en-1-yl)amino)acetate. A mixture of (E)-ethyl 2-((3-((4-fluorophenyl)imino)cyclohex-1-en-1-yl)amino)acetate (1.6 g, 1.0 equiv) in THF (8 mL) and ethanol (8 mL, 5 vol) was added with 1N. aq. NaOH while stirring, the mixture was kept at 20~30° C. for 1~2 hours. The mixture was neutralized with 1N. aq. HCl to pH=~7, and concentrated under reduced pressure. The residue was purified by column chromatography (mobile phase: DCM/MeOH=50/1~5/1) to give (E)-ethyl 2-((3-((4-fluorophenyl)imino)cyclohex-1-en-1-yl)amino)acetate. Compound $IE_4$ was further treated by reslurrying with 5 mL of MTBE to compound $IE_4$.

Example 29

Synthesis Scheme for the Compound of Formula IA$_1$

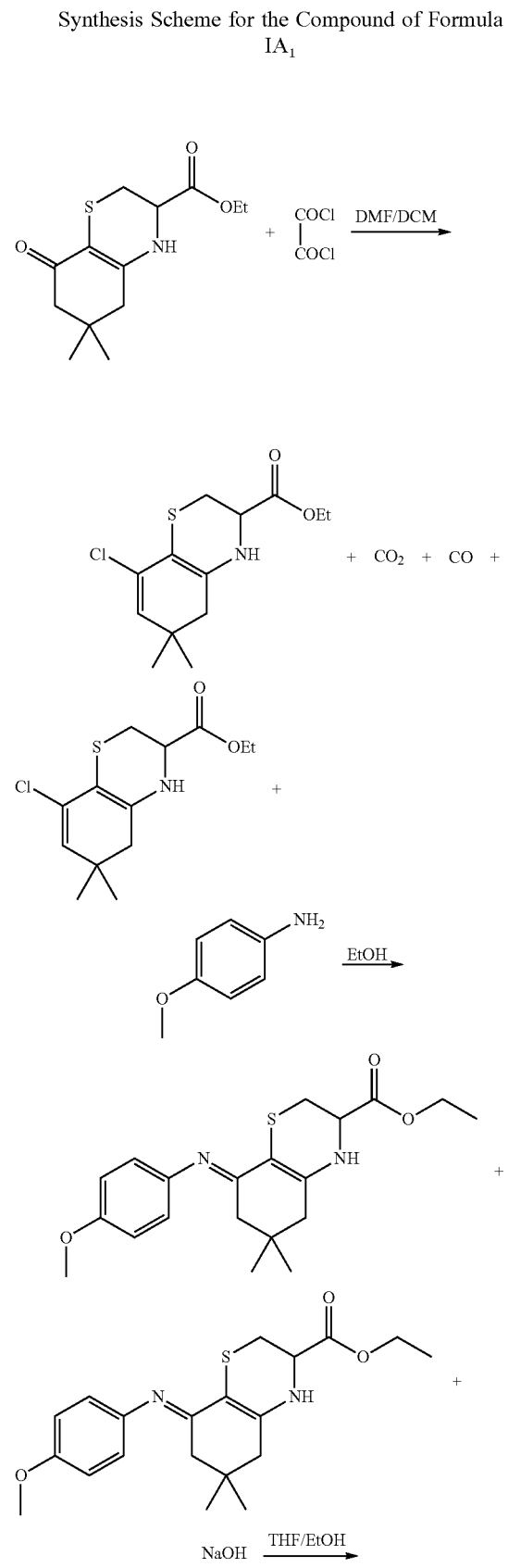

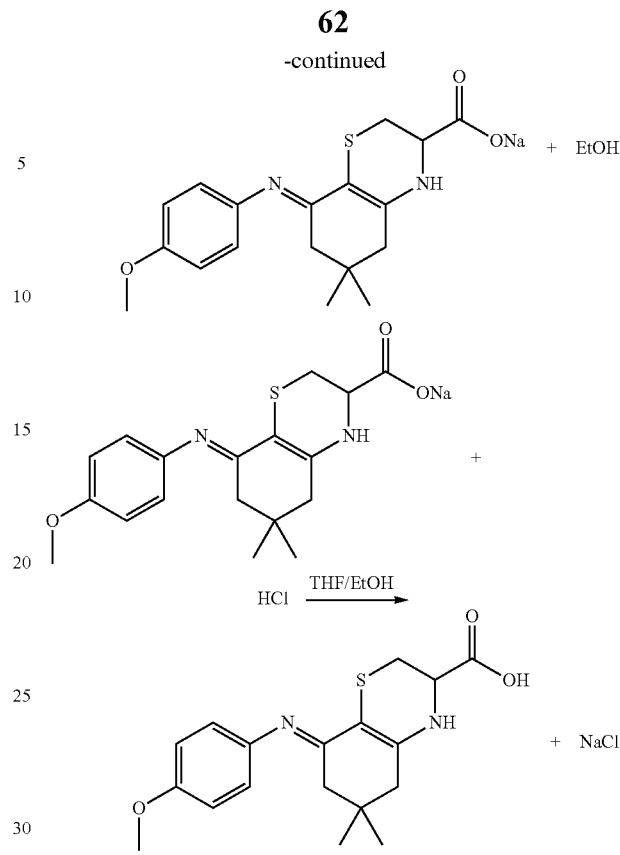

A mixture of 6,6-dimethyl-8-oxo-3,4,5,6,7,8-hexahydro-2H-benzo[b][1,4]thiazine-3-carboxylate (260 g, 1.0 equiv) and 3 drops of DMF in dichloromethane (135 mL, 10 vol) was cooled at −10~0° C. Oxalyl chloride (12.69 g, 2.0 equiv) was added drop-wise into the mixture at −10~0° C., the mixture was kept at −10~0° C. for another 1 hour with stirring. The solution was concentrated under reduced pressure to give (R)-ethyl 8-chloro-6,6-dimethyl-3,5,6,7-tetrahydro-2H-benzo[b][1,4]thiazine-3-carboxylate. The residue above was diluted with ethanol (67 mL, 5 vol), 4-methoxyaniline (12.31 g, 2.0 equiv) into the (R)-ethyl 8-chloro-6,6-dimethyl-3,5,6,7-tetrahydro-2H-benzo[b][1,4]thiazine-3-carboxylate solution, the resulting mixture was kept at 20~30° C. for 20 hour with stirring. The solution was concentrated under reduced pressure, the residue was purified by column chromatography (mobile phase: DCM/MeOH=100/1~20/1) to give (E)-ethyl 2-((3-((4-methoxyphenyl)imino)cyclohex-1-en-1-yl)amino)acetate. A mixture of (E)-ethyl 2-((3-((4-methoxyphenyl)imino)cyclohex-1-en-1-yl)amino)acetate (15.0 g, 1.0 equiv) in THF (60 mL) and ethanol (60 mL, 3 vol) was added with 120 mL of 1N. aq. NaOH while stirring, the mixture was kept at 20~30° C. for 1~2 hours. The mixture was neutralized with 1N. aq. HCl to pH=~7, and concentrated under reduced pressure. The residue was purified by column chromatography (mobile phase: DCM/MeOH=50/1~5/1) to give compound IA$_1$. The solid and active charcoal (0.86 g, 10 wt %) in 45 mL of methanol was refluxed under N2 for 2 hours. The suspension was filtered by suction to remove active charcoal, the filtrate was concentrated to dryness. The residue was treated by reslurrying with 45 mL of MTBE for ~2 hours. The suspension was filtered by suction, the cake was collected and dried at 30° C. under vacuum for at least 4 hours to give compound IA$_1$.

Example 30

Suggested Synthesis Scheme for the Compound of Formula IA₃

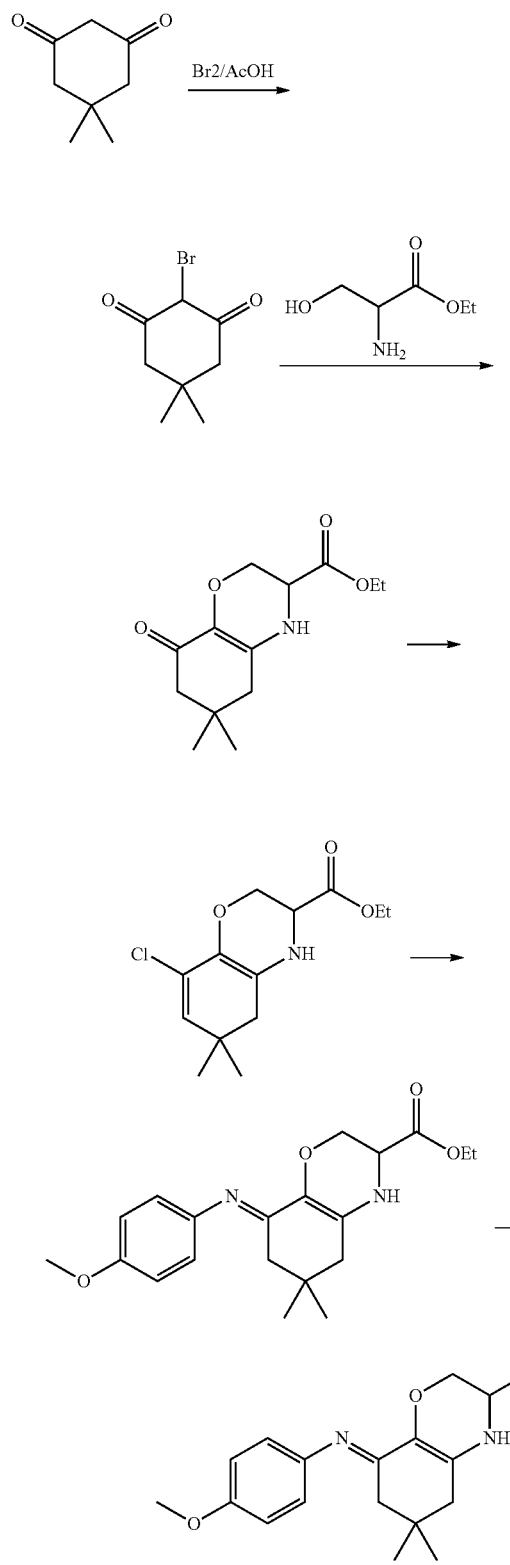

Suggested Synthesis Scheme for the Compound of Formula IA₄

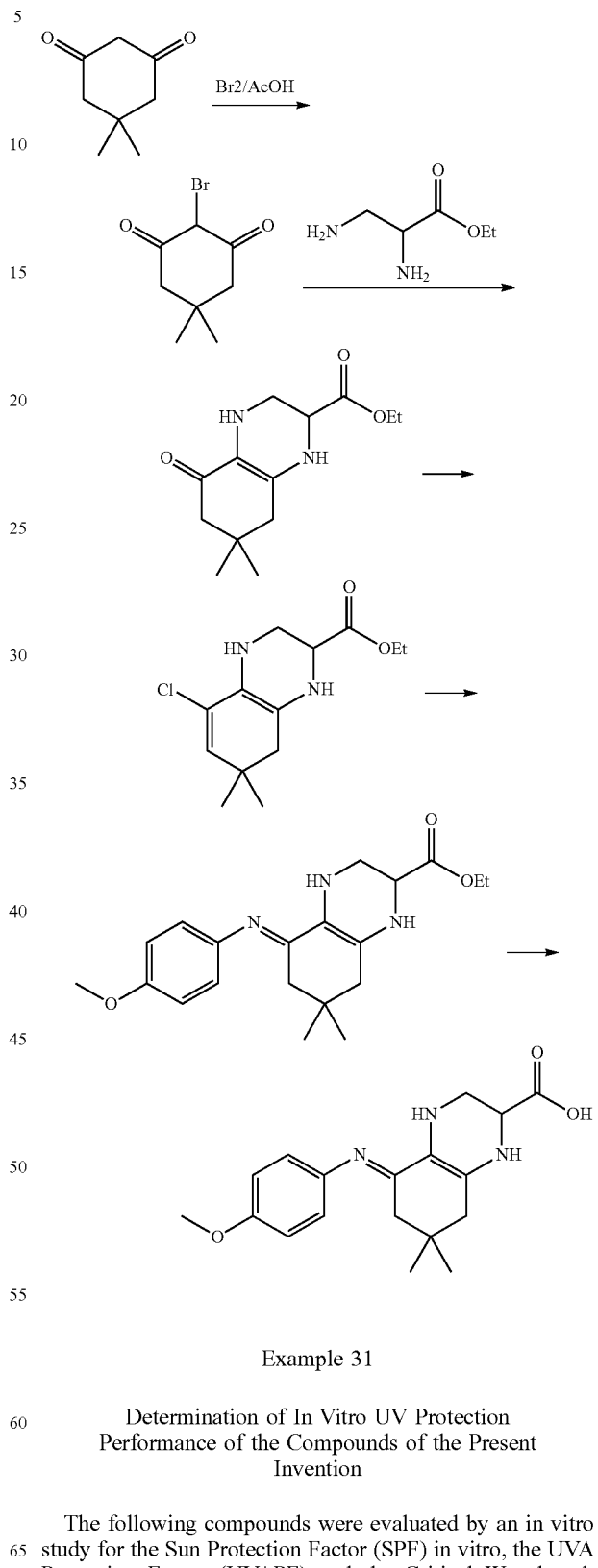

Example 31

Determination of In Vitro UV Protection Performance of the Compounds of the Present Invention The following compounds were evaluated by an in vitro study for the Sun Protection Factor (SPF) in vitro, the UVA Protection Factor (UVAPF) and the Critical Wavelength value using the Colipa UVA in vitro Method.

Compound IE₁

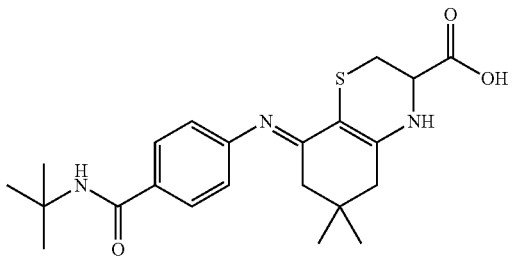

(R,E)-8-(4-tert-butylcarbamoyl)phenylimino)-6,6-dimethyl-
3,4,5,6,7,8-hexahydro-2H-benzo[b][1,4]thiazine-3-carboxylic acid Compound IF₁

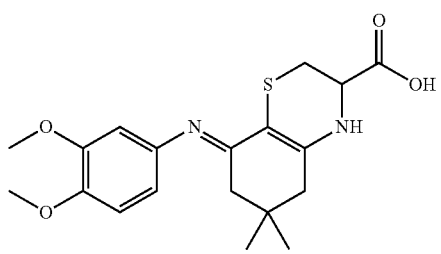

(R,E)-8-(3,4-dimethoxyphenylimino)-6,6-dimethyl-
3,4,5,6,7,8-hexahydro-2H-benzo[b][1,4]thiazine-3-carboxylic acid Compound IA₂

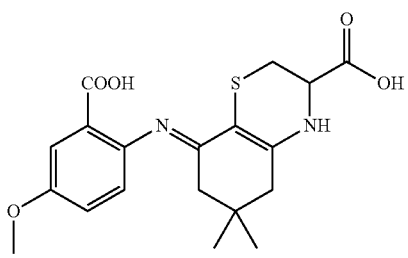

(R,E)-8-(2-carboxy-4-methoxyphenylimino)-6,6-dimethyl-
3,4,5,6,7,8-hexahydro-2H-benzo[b][1,4]thiazine-3-carboxylic acid Compound IE₄

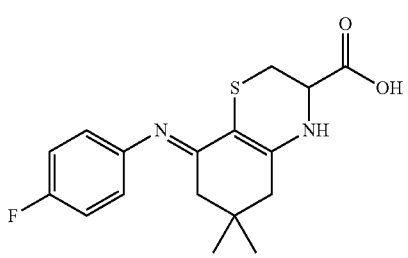

(R,E)-8-(4-fluorophenylimino)-6,6-dimethyl-3,4,5,6,7,8-
hexahydro-2H-benzo[b][1,4]thiazine-3-carboxylic acid -continued Compound IA₁

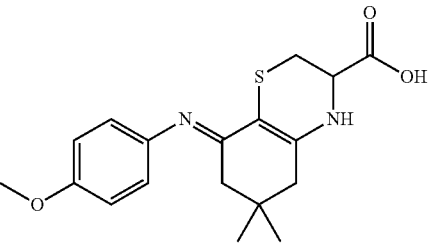

(R,E)-8-(4-methoxyphenylimino)-6,6-dimethyl-3,4,5,6,7,8-
hexahydro-2H-benzo[b][1,4]thiazine-3-carboxylic For determining the SPF in vitro value, the protection performance of the compounds against erythemally-effective UV radiation, largely confined to the UVB (290-320 nm) and short-wavelength UVA (320-340) region was calculated from the measured in vitro transmittance. The in vitro UVAPF, the UVA protection (320-400 nm) was calculated from the measured in vitro transmittance after irradiation. The Critical Wavelength Value was defined as the wavelength at which the integral of the spectral absorbance curve reached 90% of the integral over the UV spectrum from 290 to 400 nm. It has been settled that this value must be equal or over 370 nm so as to classify the product as broad-spectrum. The study consisted in a comparative assay of non-treated plates against plates treated with each of the compounds and was based on the evaluation of UV-transmittance through a thin film of sunscreen sample spread on a roughened substrate, before an after exposure to a controlled dose of UV radiation from a UV source. A Kontron 933 spectrophotomer equipped with a UV source, an integrating sphere and a monochromatic light able to deliver a flow of energy between 290 and 400 nm was used. The transmittance values were measured at 1 nm intervals. A 10-4 precision laboratory balance was used to control deposited product weight. The irradiation was provided by Sunset Atlas CPS+ with standard filter. Temperature regulation of the equipment was done in the range of 25-35° C. A pre-irradiation dose of 4 times 200 J/m²-eff (800 J/m²-eff) was delivered. The substrate was the material to which the sunscreen product was applied. Polymethylmethacrylate (PMMA) plates were used and were roughened on one side to a three-dimensional surface topography of 5 micrometers. Each compound was weighted and applied evenly to the PMMA plate with a 2-phase spreading to achieve a 0.75 mg/cm² weight/surface ratio. Spreading was performed with a light spreading move for approximately 30 seconds followed by spreading with greater pressure for approximately 30 seconds. The resulting sample was left to equilibrate for 15 minutes in the dark at room temperature to ensure a self-leveling if the formula. To account for lack of photostability, a pre-irradiation was necessary. The pre-irradiation dose was 4 minimal erythema dose (MEDs), equivalent to 800 J/m²-eff. Five measurements of spectral irradiance transmitted for each wavelength through the PMMA plate covered with the sunscreen product were obtained after pre-irradiation of the sunscreen product [P1( ), P2( ), P3( ), P4( ) and P5( )]. For each compound, mean absorbance values were determined from at least three individual PMMA plates. To validate the accuracy of the results, a control product with an established SPF of 18-20, Lot 11T0313 was tested simultaneously with the compounds.

SPF in vitro was calculated for each plate using the following equation (Colipa 2011):

$$SPF_{in\ vitro} = \frac{\int_{\lambda=290\,nm}^{\lambda=400\,nm} E(\lambda)*I(\lambda)*d\lambda}{\int_{\lambda=290\,nm}^{\lambda=400\,nm} E(\lambda)*I/(\lambda)*10_0^{-A(\lambda)}*d\lambda}$$

Where:
E( )=Erythema action spectrum (CEI-1987)
I( )=Spectral irradiance of the UV source
$A_0$( )=Mean monochromatic absorbance measurements per plate of the test compound layer before UV exposure, at each wavelength
d=Wavelength step (1 nm)
Calculation of the UVAPF for Each Plate after UV Irradiation (Colipa 2011)

$$UVAPF = \frac{\int_{\lambda=320\,nm}^{\lambda=400\,nm} P(\lambda)*I(\lambda)*d\lambda}{\int_{\lambda=320\,nm}^{\lambda=400\,nm} P(\lambda)*I(\lambda)*10^{-A(\lambda)*C}*d\lambda}$$

Where:
P( )=PPD action spectrum
I( )=Spectral irradiance of the UV source
A( )=Mean monochromatic absorbance measurements per plate of the test compound layer after UV exposure, at each wavelength
C=Coefficient of adjustment
d=Wavelength step (1 nm)
Calculation of the Critical Wavelength (FDA 2011)

$$\int_{290}^{\lambda c} lg[1/T(\lambda)]d\lambda = 0.9 \cdot \int_{290}^{400} lg[1/T(\lambda)]d\lambda$$

Where:
A( )=Mean monochromatic absorbance measurements per plate of the compound layer after UV exposure, at each wavelength
d=Wavelength step (1 nm)
An excel spreadsheet provided by the Colipa method for in vitro Determination of UVA Protection was used. This software provided the following results:
Statistical validity of carried out measurements (wavelength by wavelength);
Superimposed test curves expressed in Optical Density and in Transmission;
Each calculation was expressed as a statistical evaluation of at least 4 measurements and provided average value and results dispersion.

The raw data obtained from this study are presented in FIGS. 2-6. FIG. 2 presents the data obtained with compound $IF_1$. FIG. 3 presents the data obtained with compound $IA_1$. FIG. 4 presents the data obtained with compound $IA_2$. FIG. 5 presents the data obtained with compound $IE_4$. FIG. 6 presents the data obtained with compound $IE_1$. A summary of the results for each of the compound is presented in Table 2 below:

TABLE 2

Summary of the SPF in vitro, UVAPF and Critical Wavelength results for the tested compounds

| Test compounds | SPF in vitro | UVAPF | Critical Wavelength λc value |
|---|---|---|---|
| $IF_1$ | 2.1 | 4.1 | 390 |
| $IA_1$ | 2.4 | 8.7 | 390 |
| $IA_2$ | 5.1 | 8.1 | 392 |
| $IE_4$ | 4.5 | 8.6 | 390 |
| $IE_1$ | 3.4 | 13.5 | 391 |
| Control PMMA SPF 18-20 | 21.1 | 4.7 | 359 |

Figure 7:
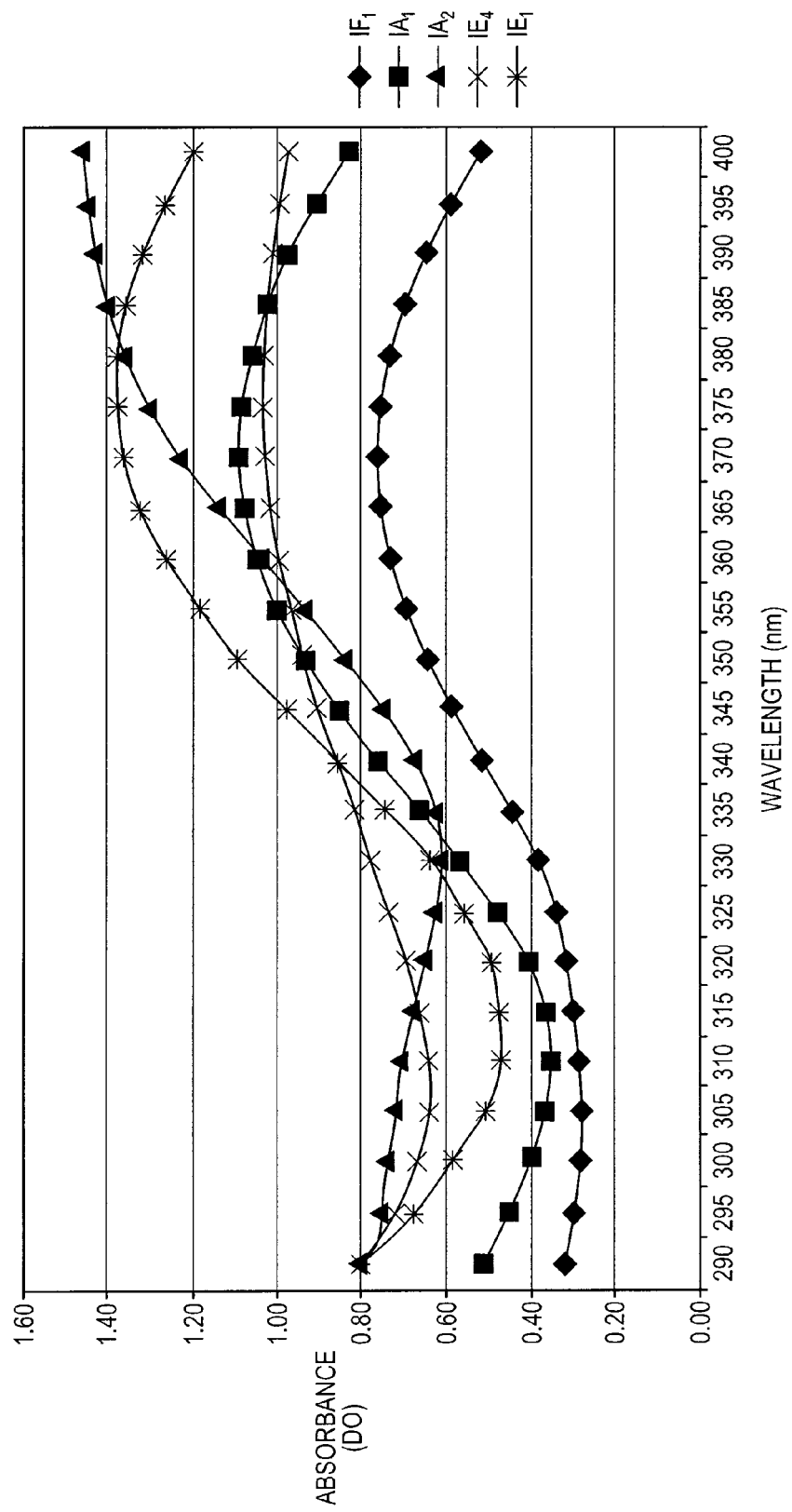
FIG. 7 is a graph showing the absorbance of compounds $IF_1$, $IA_1$, $IA_2$, $IE_4$ and $IE_1$ at the indicated wavelengths.

UVAPF in vitro measurements showed good protection against UVA rays for compounds $IE_1$, $IA_2$, $IE_4$ and $IA_1$. The critical wavelength λc value of each compound provides a broad spectrum protection to UVA and UVB rays as recommended by the FDA. FIG. 7 shows the absorbance of the tested compounds at the indicated wavelengths.

Example 32

Determination of UV Absorption Properties for Some of the Compounds

Compounds $IE_1$, $IF_1$, $IA_2$, $IE_4$, $IA_1$, $IE_2$, $ID_2$ and $ID_3$ were evaluated for their UV absorption properties. Samples were prepared as follows: 20 mg of each of the compounds were dissolved into 1 ml of methanol to yield 20 g/L solutions. The solutions were then applied onto two glass slides each. For each compound, one of the slides was aged for 20 hours under UV (Xenon instrument). Samples were then analyzed using a UVA-UVB spectrophotometer in transmission T (%) mode and compared to the non-aged slides. Absorption (A) was calculated using the following formula: $A_{sample} = (T_{slide} - T_{slide+sample})/T_{slide} \times 100$
Table 3 below shows the UVA and UVB absorption data obtained for the tested compounds.

| Tested compounds | | Plate alone UVA % | Plate alone UVB % | Plate + tested compound UVA % | Plate + tested compound UVB % | Tested compound UVA % | Tested compound UVB % |
|---|---|---|---|---|---|---|---|
| | Plate | 89.26 | 45.27 | | | | |
| $IE_1$ | no ageing | | | 1.00 | 0.73 | 98.9 | 98.4 |
| | ageing for 20 hours | | | 1.63 | 1.02 | 98.2 | 97.7 |
| $IF_1$ | no ageing | | | 0.24 | 0.31 | 99.7 | 99.3 |
| | ageing for 20 hours | | | 0.37 | 0.39 | 99.6 | 99.1 |

-continued

| Tested compounds | | Plate alone UVA % | Plate alone UVB % | Plate + tested compound UVA % | Plate + tested compound UVB % | Tested compound UVA % | Tested compound UVB % |
|---|---|---|---|---|---|---|---|
| IA$_2$ | no ageing | | | 4.56 | 4.04 | 94.9 | 91.1 |
| | ageing for 20 hours | | | 12.80 | 4.98 | 85.7 | 89.0 |
| IE$_4$ | no ageing | | | 0.49 | 0.46 | 99.5 | 99.0 |
| | ageing for 20 hours | | | 1.46 | 0.81 | 98.4 | 98.2 |
| IA$_1$ | no ageing | | | 0.99 | 1.88 | 98.9 | 95.8 |
| | ageing for 20 hours | | | 4.33 | 0.64 | 95.1 | 98.6 |
| IE$_2$ | no ageing | | | 3.51 | 2.12 | 96.1 | 95.3 |
| | ageing for 20 hours | | | 4.43 | 1.97 | 95.0 | 95.6 |
| ID$_2$ | no ageing | | | 0.44 | 0.34 | 99.5 | 99.2 |
| | ageing for 20 hours | | | 1.00 | 0.46 | 98.9 | 99.0 |
| ID$_3$ | no ageing | | | 0.47 | 0.33 | 99.5 | 99.3 |
| | ageing for 20 hours | | | 1.28 | 0.62 | 98.6 | 98.6 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All documents mentioned in the specification are herein incorporated by reference.

REFERENCES

1. Cardozo et al. 2007. Metabolites from algae with economical impact. Comparative Biochemistry and Physiology Part C: Toxicology & Pharmacology, Volume 146, Issues 1-2: 60-78.
2. Bandaranayake W M. 1998. Mycosporines: are they nature's sunscreens? Natural Product Reports. 15(2):159-72.
3. Garcia-Pichel et al., 1992. Evidence for an ultraviolet sunscreen role of the extracellular pigment scytonemin in the terrestrial *cyanobacterium Chlorogloeopsis* sp. Photochem Photobiol. 56(1):17-23.
4. Garcia-Pichel et al., 1993. Evidence Regarding the UV Sunscreen Role of a Mycosporine-Like Compound in the *Cyanobacterium Gloeocapsa* sp. Applied Environ. Microbiol. 59(1):170-176.
5. Ehling-Schilz et al., 1997. UV-B-induced synthesis of photoprotective pigments and extracellular polysaccharides in the terrestrial cyanobacterium Nostoc commune. J. Bacteriol. 179(6): 1940-5.
6. Carreto et al., 2011. Review: Mycosporine-Like Amino Acids: Relevant Secondary Metabolites. Chemical and Ecological Aspects. Mar. Drugs. 9(3), 387-446.
7. Yoshiki et al., 2009. Production of new antioxidant compound from mycosporine-like amino acid, porphyra-334 by heat treatment. Food Chem. 113, 1127-1132.

The invention claimed is:
1. A compound having the Formula I:

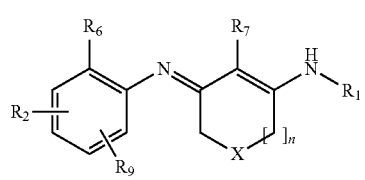

Formula I wherein,
R$_1$ and R$_7$ form a 1,4-thiazine ring;
R$_2$ is selected from the group consisting of hydrogen, halo, unsubstituted alkyl, substituted alkyl, unsubstituted alkene, substituted alkenes, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, hydroxyl, halogen, phenyl, benzyl, carboxylic acid, and ester;
R$_9$ is selected from the group consisting of hydrogen, halo, unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, hydroxyl, halogen, phenyl, benzyl, carboxylic acid, and ester;
R$_6$ is selected from the group consisting of hydrogen, unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, alkynyl, hydroxyl, sulfo, halogen, phosphono, ester, carboxylic acid, phenyl, alkyl fatty acid chain, and polyether;

$R_7$ is sulfo;

X is selected from the group consisting of carbon, nitrogen, and oxygen; and n is 1; or an acceptable salt thereof;

wherein the substituted alkyl, substituted alkene, substituted alkyne, substituted aryl, substituted heterocycle, substituted cycloalkyl, or substituted alkoxy are substituted with one or more independently selected groups consisting of halogen, alkyl, alkenyl, alkynyl, hydroxyl, alkoxyl, amino, nitro, thiol, thioether, imine, cyano, amido, phosphonato, phosphine, carboxyl, thiocarbonyl, sulfonyl, sulfonamide, ketone, aldehyde, ester, acetyl, acetoxy, carbamoyl, oxygen (=O), haloalkyl, substituted am inoacyl, substituted am inoalkyl, carbocyclic cycloalkyl, monocyclic cycloalkyl, fused polycyclic cycloalkyl, non-fused polycyclic cycloalkyl, heterocycloalkyl, monocyclic heterocycloalkyl, fused polycyclic heterocycloalkyl, non-fused polycyclic heterocycloalkyl, carbocyclic polycyclic aryl, heterocyclic polycyclic aryl, monocyclic polycyclic aryl, fused polycyclic aryl, non-fused polycyclic aryl, primary amino, secondary amino, tertiary amino, o-lower alkyl, o-aryl, aryl, aryl-lower alkyl, —$CO_2CH_3$, —$CONH_2$, —$OCH_2CONH_2$, —$NH_2$, —$SO_2NH_2$, —$OCHF_2$, —$CF_3$, and —$OCF_3$; wherein the independently selected substitution group is optionally substituted by a bridge selected from —O—$CH_2$—O— or —O-lower alkyl-O— or a fused-ring structure selected from a fused polycyclic cycloalkyl, fused polycyclic heterocycloalkyl, or fused polycyclic aryl.

2. The compound of claim 1, wherein $R_1$ is selected from the group consisting of unsubstituted alkyl; or alkyl substituted with one or more groups independently selected from trifluoromethyl, cyclopropyl, cyclobutyl, cyclopentyl, cyclohexyl, pyrrolidinyl, piperidinyl, piperazinyl, morpholinyl, thiazinyl, phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, and benzofuranyl; wherein the independently selected substitution group is optionally substituted by a bridge selected from —O—$CH_2$—O— or —O-lower alkyl-O— or a fused-ring structure selected from a fused polycyclic cycloalkyl, fused polycyclic heterocycloalkyl, or fused polycyclic aryl.

3. The compound of claim 1, wherein $R_2$ is selected from the group consisting of alkoxy, —$OCH_3$, halogen, fluorine, alkanoyl, —$CONC(CH_3)_3$, amine, and —$N(CH_2CH_3)_2$.

4. The compound of claim 1, having Formula IA:

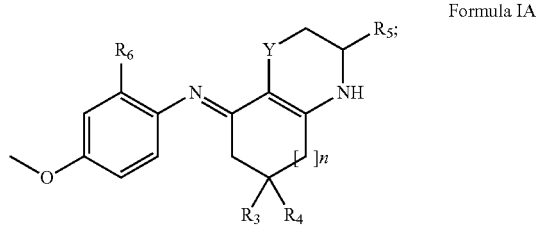

Formula IA wherein, $R_3$ and $R_4$ are each independently selected from the group consisting of hydrogen, unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo, phosphono, ester, carboxylic acid, hydroxyl, and phenyl;

$R_5$ is selected from the group consisting of unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo group, a phosphono group, ester group, carboxylic acid group, hydroxyl, and phenyl group; and Y is sulfur.

5. The compound of claim 4, wherein:

$R_3$ is selected from the group consisting of —$CH_3$ and hydrogen;

$R_4$ is selected from the group consisting of —$CH_3$ and hydrogen;

$R_5$ is —COOH; or $R_6$ is selected from the group consisting of hydrogen and —COOH.

6. The compound of claim 1, selected from the group consisting of:

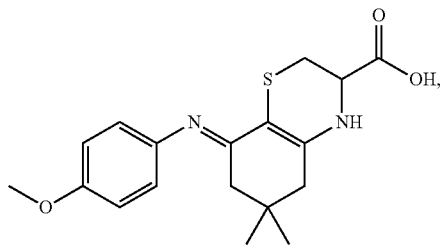

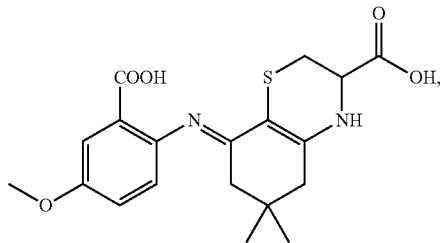

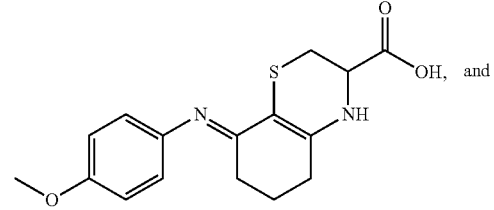

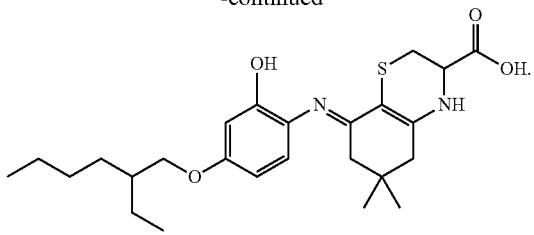

7. The compound of claim 1, having the Formula IB:

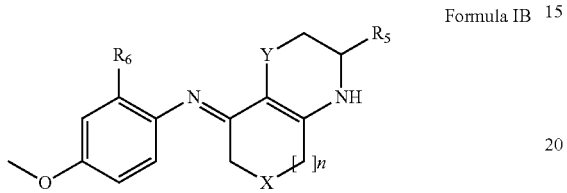

Formula IB wherein,
  R₅ is selected from the group consisting of unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo, phosphono, ester, carboxylic acid, hydroxyl, and phenyl; and
  Y is sulfur.

8. The compound of claim 7, wherein:

R₅ is selected from the group consisting of carboxyl and —COOH;
R₆ is hydrogen; or
X is selected from the group consisting of O and N.

9. The compound of claim 7, selected from the group consisting of:

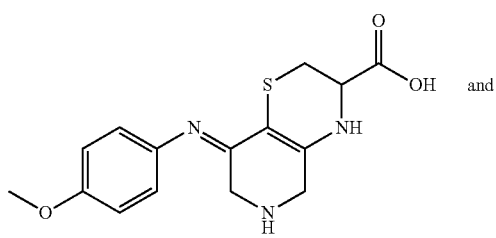 and

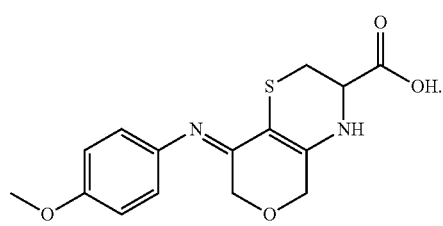

10. The compound of claim 1, having the Formula IE:

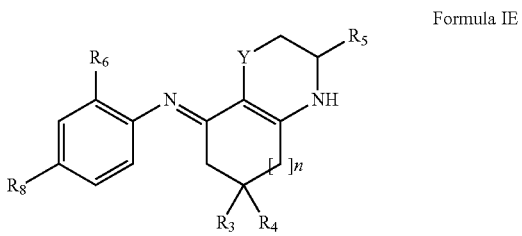

Formula IE wherein,
  R₃ and R₄ are each independently selected from the group consisting of hydrogen, unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo, phosphono, ester, carboxylic acid group, hydroxyl, and phenyl;
  R₅ is selected from the group consisting of unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo, phosphono, ester, carboxylic acid, hydroxyl, and phenyl;
  R₈ is selected from the group consisting of hydrogen, unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, alkynyl, hydroxyl, sulfo, halogen, phosphono, ester, carboxylic acid, phenyl, amine, alkyl fatty acid chain, and polyether; and
  Y is sulfur.

11. The compound of claim 10, wherein:
R₃ and R₄ are each selected from the group consisting of alkyl and —CH₃;
R₅ is selected from the group consisting of carboxyl and —COOH;
R₆ is selected from the group consisting of hydrogen and hydroxyl; or
R₈ is selected from the group consisting of alkanoyl, hydrogen, halogen, and amine.

12. The compound of claim 10, selected from the group consisting of:

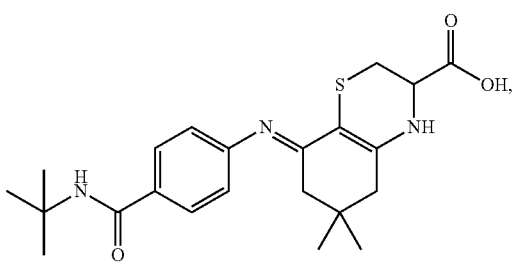

-continued

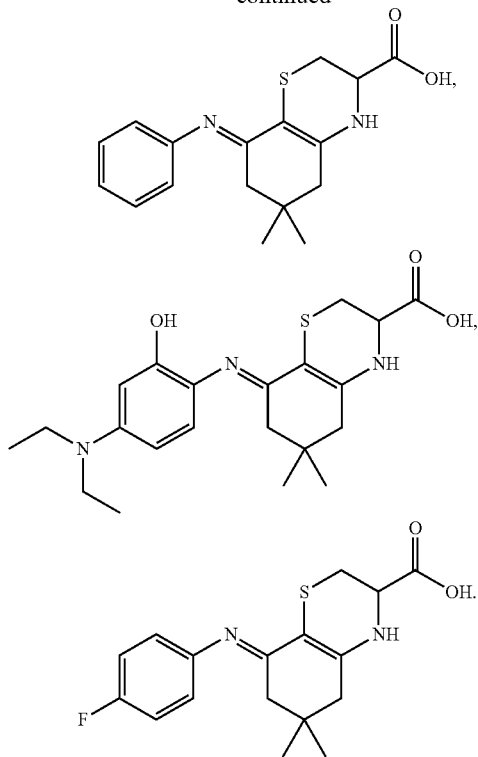
and

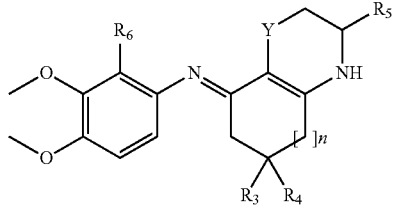

13. The compound of claim 1, having formula IF:

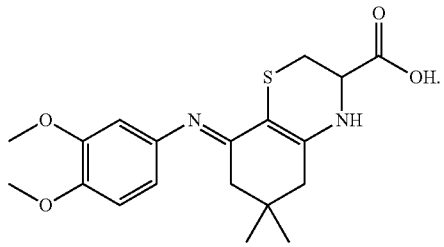 [SMILES: COc1ccc(/N=C2\CC(C)(C)CC3=C2SCC(C(=O)O)N3)cc1OC]

Formula IF wherein,

R$_3$ and R$_4$ are each independently selected from the group consisting of hydrogen, unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo, phosphono, ester, carboxylic acid, and phenyl;

R$_5$ is selected from the group consisting of unsubstituted alkyl, substituted alkyl, unsubstituted alkene, substituted alkene, unsubstituted alkyne, substituted alkyne, unsubstituted aryl, substituted aryl, unsubstituted heterocycle, substituted heterocycle, unsubstituted cycloalkyl, substituted cycloalkyl, unsubstituted alkoxy, substituted alkoxy, alkanoyl, sulfo, phosphono, ester, carboxylic acid, hydroxyl, and phenyl; and Y is sulfur.

14. The compound of claim 13, wherein
R$_5$ is carboxyl;
R$_3$ and R$_4$ are each selected from the group consisting of alkyl and —CH$_3$; or
R$_6$ is hydrogen.

15. The compound of claim 13, being:

16. The compound of claim 1, wherein:
the compound absorbs ultraviolet (UV) radiation;
the compound absorbs UVA radiation;
the compound absorbs UVB radiation;
the compound has a Critical Wavelength value of at least 370 nm;
the compound has a Critical Wavelength value of at least 390 nm; or
the compound accommodating free radicals.

17. The compound of claim 1, wherein the substituted alkyl, substituted alkene, substituted alkyne, substituted aryl, substituted heterocycle, substituted cycloalkyl, or substituted alkoxy are substituted with one or more independently selected groups consisting of trifluoromethyl, cyclopropyl, cyclobutyl, cyclopentyl, cyclohexyl, pyrrolidinyl, piperidinyl, piperazinyl, morpholinyl, thiazinyl, phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, and benzofuranyl; wherein the independently selected substitution group is optionally substituted by a bridge selected from —O—CH$_2$—O— or —O-lower alkyl-O— or a fused-ring structure selected from a fused polycyclic cycloalkyl, fused polycyclic heterocycloalkyl, or fused polycyclic aryl.

\* \* \* \* \*